United States Patent
Briner et al.

(10) Patent No.: US 6,881,733 B1
(45) Date of Patent: Apr. 19, 2005

(54) SEROTONERGIC BENZOFURANS

(75) Inventors: Karin Briner, Indianapolis, IN (US); Joseph Paul Burkhart, Plainfield, IN (US); Timothy Paul Burkholder, Carmel, IN (US); Brian Eugene Cunningham, Martinsville, IN (US); Matthew Joseph Fisher, Mooresville, IN (US); William Harlan Gritton, Zionsville, IN (US); Cynthia Darshini Jesudason, Indianapolis, IN (US); Shawn Christopher Miller, Noblesville, IN (US); Jeffrey Thomas Mullaney, Indianapolis, IN (US); Matthew Robert Reinhard, Indianapolis, IN (US); Roger Ryan Rothhaar, Reelsville, IN (US); Freddie Craig Stevens, Indianapolis, IN (US); Leonard Larry Winneroski, Greenwood, IN (US); Yanping Xu, Fishers, IN (US); Yao-Chang Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 174 days.

(21) Appl. No.: 10/031,414

(22) PCT Filed: Jul. 21, 2000

(86) PCT No.: PCT/US00/19544

§ 371 (c)(1),
(2), (4) Date: May 29, 2002

(87) PCT Pub. No.: WO01/09122

PCT Pub. Date: Feb. 8, 2001

Related U.S. Application Data

(60) Provisional application No. 60/146,181, filed on Jul. 29, 1999, and provisional application No. 60/172,601, filed on Dec. 20, 1999.

(51) Int. Cl.[7] .................. C07D 413/04; A61K 31/4525; A61K 31/4025; A61K 31/55; A61P 25/24

(52) U.S. Cl. .................. 514/217.03; 514/320; 514/337; 514/422; 540/596; 546/196; 546/284.1; 548/525

(58) Field of Search ............... 514/217.03, 320, 514/337, 422; 540/596; 546/196, 284.1; 548/525

(56) References Cited

FOREIGN PATENT DOCUMENTS

| EP | 0 189 612 A | 8/1986 |
|---|---|---|
| EP | 0 006 524 A | 1/1990 |
| EP | 0 398 413 A | 11/1990 |
| EP | 0 982 304 A | 3/2000 |
| EP | 982304 A1 * | 3/2000 |
| WO | WO 00 00196 A | 1/2000 |
| WO | WO 00 00203 A | 1/2000 |

OTHER PUBLICATIONS

Robichaud, A.J. et al, Ann. Reports Med. Chem., 38, 2000, 11–20.*
Martin, J.R. et al, J. Pharm. Exp. Therp., 286, pp. 913–924.*
Patent Abstracts of Japan: vol. 016 No. 071 (c–0913) (Feb. 21, 1992) & JP 03 264683 A (Dai Ichi Seiyaku Co Ltd), (Nov. 25, 1991) abstract.
McGarry D.G. et al.: Benzofuran based PDE4 Inhibitors: Bioorganic & Medicinal Chemistry., vol. 7, No. 6, 1999 pp. 1131–1139, XP000978427 Elsevier Science Ltd., GB ISSN: 0968-896.

* cited by examiner

*Primary Examiner*—Richard L. Raymond
*Assistant Examiner*—Thomas McKenzie
(74) *Attorney, Agent, or Firm*—Robert Craig Tucker

(57) ABSTRACT

The present invention provides serotonergic benzofurans of Formula (I): where A, R, $R^1$, $R^2$, $R^3$, and $R^4$ are as described in the specification.

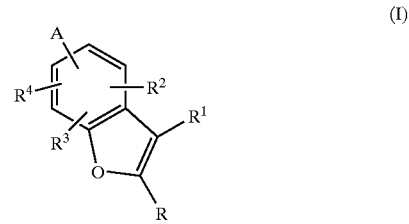

(I)

18 Claims, No Drawings

SEROTONERGIC BENZOFURANS

This application claims priority to U.S. Provisional applications No. 60/146,181 filed Jul. 29, 1999 and No. 60/172,601 filed Dec. 20, 1999.

The neurotransmitter serotonin (5-hydroxytryptamine, 5-HT) has a rich pharmacology arising from a heterogeneous population of at least seven receptor classes. The serotonin $5\text{-HT}_2$ class is further subdivided into at least three subtypes, designated $5\text{-HT}_{2a}$, $5\text{-HT}_{2b}$, and $5\text{-HT}_{2c}$. The $5\text{-HT}_{2c}$ receptor has been isolated and characterized (Julius, et al., U.S. Pat. No. 4,985,352), and transgenic mice lacking the $5\text{-HT}_{2c}$ receptor have been reported to exhibit seizures and an eating disorder resulting in increased consumption of food (Julius, et al., U.S. Pat. No. 5,698,766). Compounds selective for the $5\text{-HT}_{2c}$ receptor would provide useful therapies for the treatment of seizure and eating disorders without the side effects associated with current therapies. The present invention provides new benzofurans useful as $5\text{-HT}_{2c}$ receptor agonists.

The present invention provides benzofurans of Formula I:

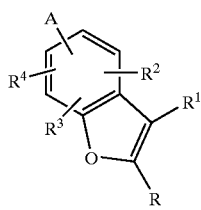

where:

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, trifluoromethyl, cyano, $C_1$–$C_4$ alkoxy, $C_1$–$C_4$ alkoxycarbonyl, $C_1$–$C_6$ alkyl, $C_1$–$C_6$ alkyl substituted with a substituent selected from the group consisting of $C_1$–$C_4$ alkoxy and hydroxy, or —C(O)NHR$^9$;

$R^9$ is $C_1$–$C_8$ alkyl where the alkyl chain is optionally substituted with a substituent selected from the group consisting of phenyl and pyridyl;

A is attached at either the 4- or 7-position of the benzofuran nucleus and is an amine of formula:

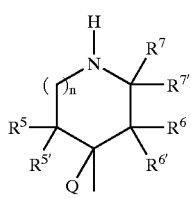

n is 0, 1, or 2;

$R^5$, $R^6$, and $R^7$ are independently hydrogen or $C_1$–$C_4$ alkyl;

Q is hydrogen;

$R^{5'}$ is hydrogen or methyl, provided that $R^{5'}$ may be methyl only when $R^5$ is other than hydrogen, or $R^{5'}$ and Q taken together with the carbon atoms to which they are attached form a double bond;

$R^{6'}$ is hydrogen or methyl, provided that $R^{6'}$ may be methyl only when $R^6$ is other than hydrogen, or $R^{6'}$ and Q taken together with the carbon atoms to which they are attached form a double bond;

$R^{7'}$ is hydrogen or methyl, provided that $R^{7'}$ may be methyl only when $R^7$ is other than hydrogen;

or pharmaceutically acceptable acid addition salts thereof subject to the following provisos:

a) when n is 1 or 2, at least one of $R^5$, $R^6$, and $R^7$, must be other than hydrogen; and b) no more than two of $R^5$, $R^{5'}$, $R^6$, $R^{6'}$, $R^7$, and $R^{7'}$ may be other than hydrogen.

This invention also provides a pharmaceutical formulation which comprises, in association with a pharmaceutically acceptable carrier, diluent or excipient, a compound of Formula I.

The present invention provides a method for increasing activation of the $5\text{-HT}_{2C}$ receptor in mammals comprising administering to a mammal in need of such activation a pharmaceutically effective amount of a compound of Formula I.

The present invention also provides a method for treating obesity in mammals comprising administering to a mammal in need of such treatment a pharmaceutically effective amount of a compound of Formula I.

A further embodiment of this invention is a method for increasing activation of the $5\text{-HT}_{2C}$ receptor for treating a variety of disorders which have been linked to decreased neurotransmission of serotonin in mammals. Included among these disorders are depression, obesity, bulimia, premenstrual syndrome or late luteal phase syndrome, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, anxiety, seizure disorders, and mutism. Any of these methods employ a compound of Formula I.

This invention also provides the use of a compound of Formula I for the manufacture of a medicament for the treatment of obesity. Additionally, this invention provides a pharmaceutical formulation adapted for the treatment of obesity containing a compound of Formula I. Furthermore, this invention includes a method for the treatment of obesity which comprises administering an effective amount of a compound of Formula I.

The general chemical terms used in the formulae above have their usual meanings. For example, the term "alkyl" includes such groups as methyl, ethyl, n-propyl, isopropyl, n-butyl, isobutyl, sec-butyl, tert-butyl, and the like. The term "alkoxy" includes methoxy, ethoxy, propoxy, isopropoxy, butoxy and the like. The term "acyl" includes such groups as formyl, acetyl, propionyl, butyryl, 2-methylpropionyl, and the like. The term "halo" includes fluoro, chloro, bromo and iodo.

The term "$C_1$–$C_6$ alkyl substituted with a substituent selected from the group consisting of $C_1$–$C_4$ alkoxy and hydroxy" means a branched or linear alkyl group substituted in the carbon chain with one or two substituents independently selected from hydroxy or $C_1$–$C_4$ alkoxy.

The term "$C_1$–$C_8$ alkyl where the alkyl chain is optionally substituted with a substituent selected from the group consisting of phenyl and pyridyl" means a branched or linear alkyl group which may be substituted in the carbon chain with a phenyl or pyridinyl ring.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyro-phosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid and fumaric acid.

The skilled artisan will appreciate that substituents on moiety "A" of certain compounds of the present invention give rise to cis- and trans-isomers. An example of this isomeric relationship is illustrated by the following benzofurylpiperidines:

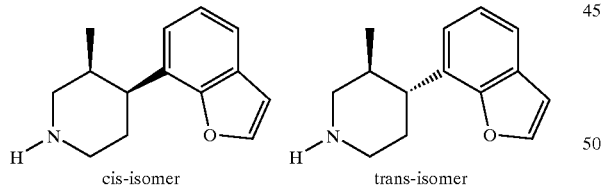

The compounds of the invention may exist as a mixture of cis- and trans-isomers or as the individual isomers. It is preferred that the compounds exist as the individual isomers. Compounds in the cis-configuration are especially preferred.

The skilled artisan will also appreciate that the compounds of the present invention have at least one chiral carbon, and may therefore exist as a racemate, as individual enantiomers or diastereomers, and as mixtures of individual enantiomers or diastereomers. Individual enantiomers of compounds of the invention are illustrated by the following structures where $R^6$ or $R^7$ are other than hydrogen:

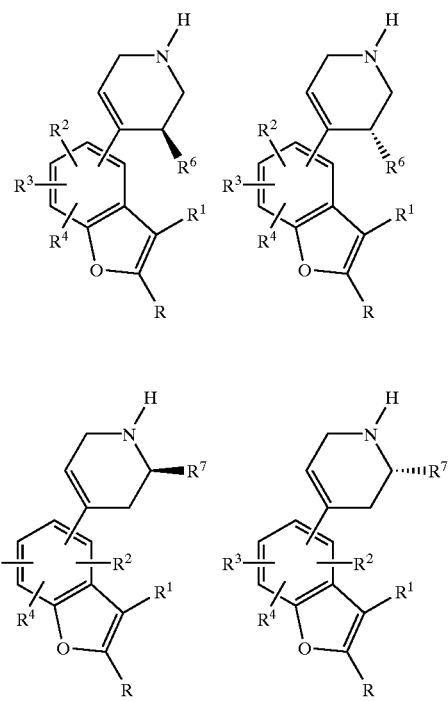

Individual diastereomers are illustrated by the following structures:

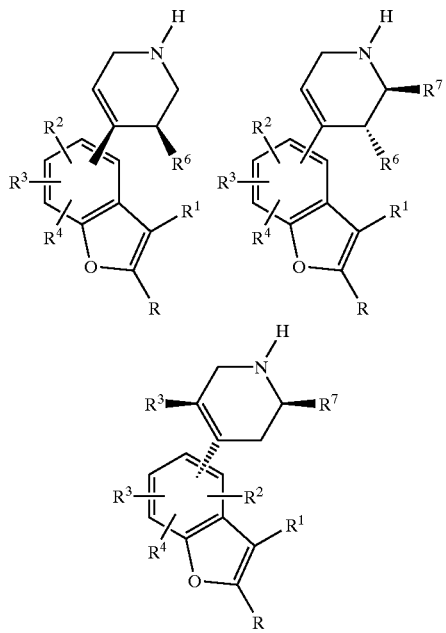

The enantiomers and diastereomers illustrated above are representative of other enantiomers and diastereomers created by other combinations of certain non-hydrogen substituents on the compounds of the invention, and are not intended to limit the scope of the present invention in any way. Furthermore, the skilled artisan will appreciate that certain substituents on the benzofuryl ring of the compounds of the invention introduce additional asymmetric centers into the molecule, creating additional optical isomers as described above.

While it is a preferred embodiment of the invention that the compounds of the invention exist, are formulated, and are used as single enantiomers or diastereomers, the present invention also contemplates the compounds of the invention existing in racemic form and as mixtures of the individual enantiomers and diastereomers. The methods and formulations of the invention also contemplate the use and formulation of the compounds of the invention in their racemic form and as mixtures of the individual enantiomers and diastereomers.

The individual enantiomers and diastereomers may be prepared by chiral chromatography of the racemic or enantiomerically or diastereomerically enriched free amine, or fractional crystallization of salts prepared from racemic or enantiomerically or diastereomerically enriched free amine and a chiral acid. Alternatively, the free amine may be reacted with a chiral auxiliary and the enantiomers or diastereomers separated by chromatography followed by removal of the chiral auxiliary to regenerate the free amine. Furthermore, separation of enantiomers or diastereomers may be performed at any convenient point in the synthesis of the compounds of the invention. The compounds of the invention may also be prepared by the use of chiral syntheses. A particularly useful method for the separation of enantiomers or diastereomers is the "Dutch Resolution" described in EP 0 838 448 A1 (See also: T. Vries, et al., *Angew. Chem. Int. Ed.*, 37, 2349–2354 (1998); 15 and B. Broxterman, et al., *Chim. Oggi.*, 16, 34–37 (1998)). Especially useful salts for resolution include 3-bromocamphor-8-sulfonic acid, mandelic acid, dibenzoyltartaric acid, di-(p-methylbenzoyl)tartaric acid, and di-(p-methoxybenzoyl) tartaric acid.

While all of the compounds of Formula I are useful 5-HT$_{2C}$ agonists, certain classes of the compounds are preferred. The following paragraphs describe such preferred classes:

aa) A is attached at the 7-position of the benzofuran ring;
ab) n is 0 or 1;
ac) n is 1;
ad) Q is hydrogen;
ae) Q and $R^{5'}$, taken together with the carbon atoms to which they are attached, form a double bond;
af) Q and $R^{6'}$, taken together with the carbon atoms to which they are attached, form a double bond;
ag) R is hydrogen;
ah) R is halo;
ai) R is $C_1$–$C_6$ alkyl;
aj) $R^1$ is hydrogen;
ak) $R^1$ is halo;
al) $R^1$ is trifluoromethyl;
am) $R^1$ is $C_1$–$C_6$ alkyl;
an) $R^2$ is hydrogen;
ao) $R^2$ is halo;
ap) $R^2$ is fluoro;
aq) $R^2$ is trifluoromethyl;
ar) $R^3$ is hydrogen;
as) $R^3$ is halo;
at) $R^3$ is fluoro;
au) $R^3$ is trifluoromethyl;
av) $R^4$ is hydrogen;
aw) $R^4$ is halo;
ax) $R^4$ is fluoro;
ay) $R^4$ is trifluoromethyl;
az) $R^5$ is hydrogen;
ba) $R^5$ is $C_1$–$C_4$ alkyl;
bb) $R^5$ is methyl;
bc) $R^{5'}$ is hydrogen;
bd) $R^{5'}$ is methyl;
be) $R^6$ is hydrogen;
bf) $R^6$ is $C_1$–$C_4$ alkyl;
bg) $R^6$ is methyl;
bh) $R^{6'}$ is hydrogen;
bi) $R^{6'}$ is methyl;
bj) $R^7$ is hydrogen;
bk) $R^7$ is $C_1$–$C_4$ alkyl;
bl) $R^7$ is methyl;
bm) $R^{7'}$ is hydrogen;
bn) $R^{7'}$ is methyl;
bo) The compound is a free base;
bp) The compound is a salt;
bq) The compound is the hydrochloride salt;
br) The compound is the fumarate salt;
bs) The compound is a racemate;
bt) The compound is a single enantiomer;
bu) The compound is a single diastereomer;
bv) A is attached at the 7-position of the benzofuryl moiety and only one of $R^2$, $R^3$, or $R^4$ is hydrogen;
bw) A is attached at the 7-position of the benzofuryl moiety and any two of $R^2$, $R^3$, or $R^4$ is hydrogen;
bx) A is attached at the 7-position of the benzofuryl moiety and all three of $R^2$, $R^3$, and $R^4$ are other than hydrogen;
by) One of $R^5$, $R^6$, and $R^7$ is other than hydrogen;
bz) Two of $R^5$, $R^{5'}$, $R^6$, $R^{6'}$, $R^7$, and $R^{7'}$ are other than hydrogen;
ca) n is 1 and A is monosubstituted in the three position;
cd) n is 1 and A is substituted in both the two and three positions.

It will be understood that the above classes may be combined to form additional preferred classes.

The present invention also provides a method for increasing activation of the 5-HT$_{2C}$ receptor in mammals by administering to a mammal in need of such activation a pharmaceutically effective amount of a compound of Formula I. The preferred mammal is human.

The compounds of the invention may be prepared beginning with an appropriately substituted benzofuran and a suitable ketone as illustrated in the following scheme, where X is bromo or iodo, Pg is a nitrogen protecting group; and the variables n, R, $R^1$, $R^2$, $R^3$, $R^4$, $R^5$, $R^{5'}$, $R^6$, $R^{6'}$, $R^7$, and $R^{7'}$ are as previously defined:

Synthetic Scheme I

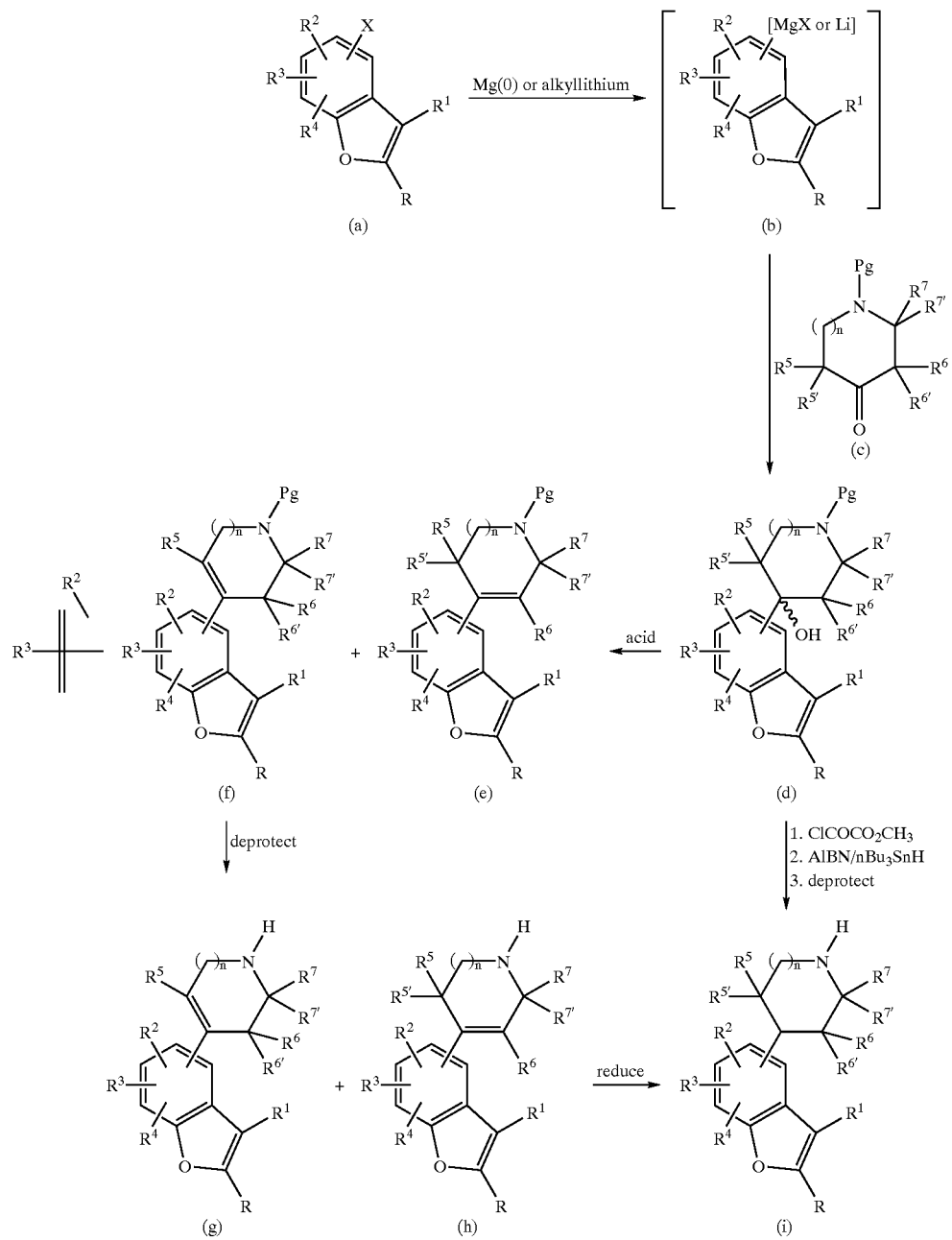

An appropriately substituted bromo- or iodobenzofuran (a) in an appropriate solvent, typically tetrahydrofuran or diethyl ether, is treated with magnesium metal to prepare the corresponding Grignard reagent (b). Alternatively, a solution of the bromo- or iodobenzofuran in a suitable solvent, typically diethyl ether or tetrahydrofuran, is treated with an alkyllithium, typically tert-butyllithium, to prepare the corresponding organolithium reagent (b). Either of these reagents is then reacted with an appropriately substituted, nitrogen protected, pyrrolidinone (n=0), piperidinone (n=1), or homopiperidinone (n=2) (c) to prepare the benzyl alcohol (d). Nitrogen protecting groups useful for this reaction are well known to the skilled artisan. A summary of such groups may be found in Greene's *Protective Groups in Organic Synthesis*, Second Edition, Wiley Interscience. Particularly useful protecting groups include benzyl and tert-butoxycarbonyl.

The benzyl alcohol (d) is dehydrated by treatment with an acid, typically p-toluenesulfonic acid, methanesulfonic acid, hydrochloric acid or hydrobromic acid, to provide a mixture of alkenes. When Pg is a moiety stable to acidic dehydration conditions, exemplified by compounds where Pg is benzyl, the alkenes of formula (e) and (f) are prepared. When Pg is labile to acidic conditions, exemplified by compounds where Pg is tert-butoxycarbonyl, the compounds of formula (g) and (h) are prepared directly. Either of these mixtures of alkenes may be separated into their individual isomers by chromatography or fractional crystallization. The compounds may then be nitrogen deprotected, if necessary, to provide compounds of the present invention.

An alternative to acidic dehydration of the benzyl alcohol (d) is a tin mediated deoxygenation. This deoxygenation is accomplished by first converting the benzylic alcohol to the corresponding oxalate ester by treatment with methyl chlorooxalate under standard acylation conditions. The resulting derivative is treated with tri(n-butyl)tin hydride in the presence of 2,2'-azobisisobutyronitrile to provide the compound of formula (j). This compound is then nitrogen deprotected to provide compounds of the present invention.

An alternative to the anion based coupling described above is the palladium catalyzed coupling described in the following scheme, where the variables are as previously described.

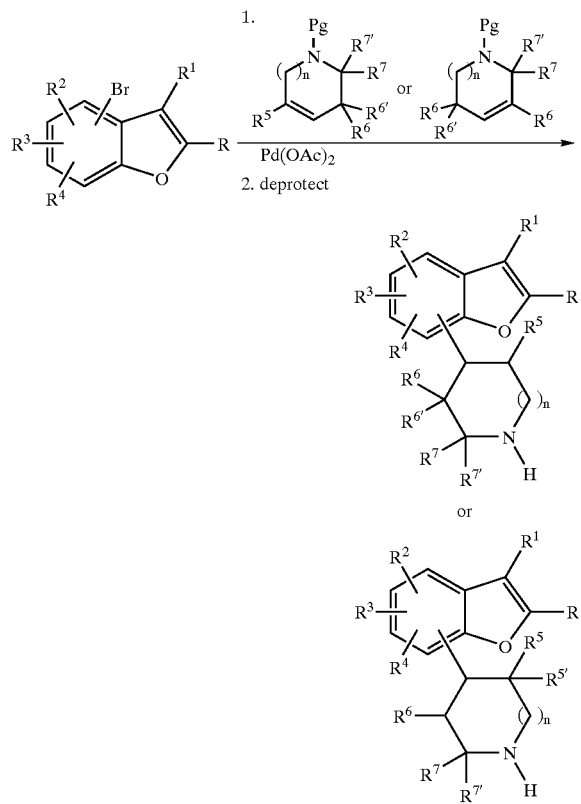

An appropriately substituted bromobenzofuran and the requisite N-protected dihydropyrrole (n=0), tetrahydropyridine (n=1) or didehydrohomopiperidine (n=2) in an appropriate solvent, typically dimethylformamide, is heated with a source of palladium, such as palladium acetate, an appropriate phosphine, such as tri(fur-2-yl)phosphine, an appropriate amine, such as diisopropylethylamine, and lithium chloride. The product of this coupling reaction is then nitrogen deprotected to provide compounds of the present invention.

Alternatively, the palladium-mediated coupling may be performed on an appropriately substituted benzofurylboronic acid derivative and an appropriate enoltriflate of the corresponding pyrrolidinone, piperidinone, or homopiperidinone. These coupling partners may be prepared from the corresponding bromobenzofurans and ketones respectively by procedures well known in the art. This type of palladium coupling reaction is well known in the art (See: N. Miyaura et al., *Journal of Organic Chemistry*, 51, 5467–5471 (1986); Y. Hoshino, et al., *Bull. Chim. Soc. Jap.*, 61, 3008–3010 (1988); N. Miyaura et al., *Journal of the American Chemical Society*, 111, 314–321 (1989); W. J. Thompson, et al., *Journal of Organic Chemistry*, 53, 2052–2055 (1983); and T. I. Wallow and B. M. Novack, *Journal of Organic Chemistry*, 59, 5034–5037 (1994)).

The skilled artisan will appreciate that the conditions for any of the nitrogen deprotection steps described above depend upon the nature of the nitrogen protecting group. For example, the benzyl group may be removed by treatment with 1-chloroethyl chloroformate or by catalytic hydrogenation. The tert-butoxycarbonyl group may be removed by treatment with acid, for example, trifluoroacetic acid or hydrogen chloride.

The requisite benzofuran intermediates are either commercially available or may be prepared from an appropriately substituted phenol by methods well known in the art as illustrated in the following scheme where variables $R^2$, $R^3$, and $R^4$ are as previously defined:

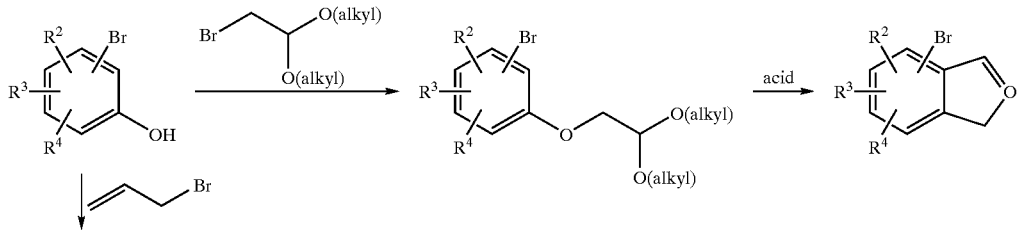

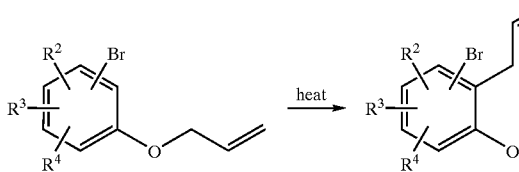

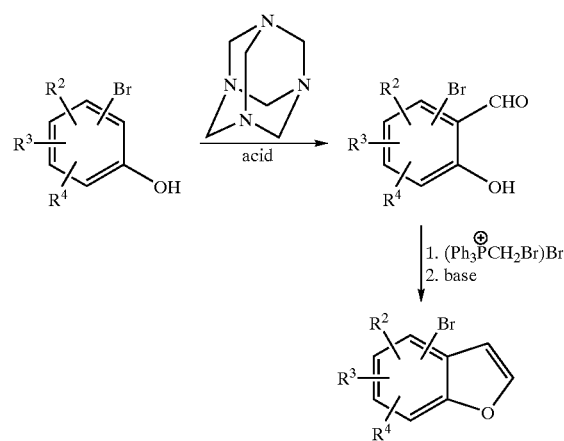

A solution of an appropriately substituted phenol in a suitable solvent, typically dimethylformamide, is treated with a base, to generate the corresponding phenoxide. Bases useful for this reaction include hydride sources, such as sodium or potassium hydride, or carbonates, such as sodium or potassium carbonate. The phenoxide solution is then reacted with a chloro- or bromoacetaldehyde which is protected as a cyclic or dialkyl acetal. Bromoacetaldehyde diethyl acetal is particularly useful for this reaction. The phenoxyacetaldehyde acetal prepared by this procedure is reacted with a source of acid in a suitable solvent to provide the desired benzofuran. Suitable solvents include aromatic solvents such as toluene, xylene, benzene, and halobenzenes such as chlorobenzene. Suitable acids include concentrated sulfuric acid, polyphosphoric acid, and acidic resins such as Amberlyst 15™.

Alternatively, the phenoxide solution is treated with an allyl bromide or allyl chloride to provide, after standard isolation and purification procedures, the corresponding allyl ether. This purified ether is heated at a temperature sufficient to effect an ortho-Claisen rearrangement to provide the corresponding o-allylphenol. It is critical that the allyl ether employed in this rearrangement is substantially free of residual dimethylformamide. The skilled artisan will appreciate that, depending upon the location and nature of the $R^2$ and $R^3$ substituents, the rearrangement can provide a mixture of two isomeric products. These isomers may be separated at this stage or later in the synthetic sequence as is convenient or desired. The separation may be effected by chromatography, distillation, or crystallization. The o-allylphenol is then treated with an excess of ozone in an appropriate solvent, dichloromethane and methanol are useful solvents for this step. The reaction mixture is then purged of ozone and the ozonide is treated under reducing conditions, typically by treatment with triphenylphosphine or dimethylsulfide, to provide the corresponding phenylacetaldehyde. The skilled artisan will appreciate that the orientation of the aldehyde with the respect to the phenolic hydroxyl group gives rise to the formation of a cyclic hemiacetal which exists in some equilibrium mixture with the free hydroxyaldehyde. A solution of this equilibrium mixture in a suitable solvent, such as toluene, is treated with a catalytic amount of an appropriate acid, such as sulfuric acid, to provide the desired benzofuran.

The skilled artisan will appreciate that benzofurans substituted in the 2- and/or 3-position may be prepared by modification of the chemistry described in Synthetic Scheme III. For example, the phenol may be alkylated with a suitable haloketone and then cyclized to provide a substituted benzofuran. Alternatively, the benzofuran moiety may be substituted in the 2- or 3-position at any convenient point in the synthesis of the compounds of the present invention by methods known to those skilled in the art.

The requisite benzofurans may also be prepared from an appropriately substituted phenol as illustrated in the following scheme where variables $R^2$, $R^3$, and $R^4$ are as previously defined:

Synthetic Scheme IV

A mixture of an appropriate phenol and hexamethylenetetramine are treated with an appropriate acid, such as trifluoroacetic acid, to provide upon aqueous workup the corresponding o-formylphenol. This o-formylphenol is then treated with (bromomethyl)triphenylphosphonium bromide followed by an appropriate base such as potassium tert-butoxide to provide the desired benzofuran.

The requisite pyrrolidinones (n=0) and piperidinones (n=1) are either commercially available or may be prepared by methods well known in the art. The requisite homopiperidinones (n=2) may be prepared from appropriately substituted piperidinones. One such approach is a modification of a synthesis described by Roglans, et al., *Synthetic Communications*, 22(9), 1249–1258 (1992). Procedures for the preparation of pyrrolidinones and homopiperidinones are described in the following scheme where the variables are as previously described.

Synthesis Scheme V

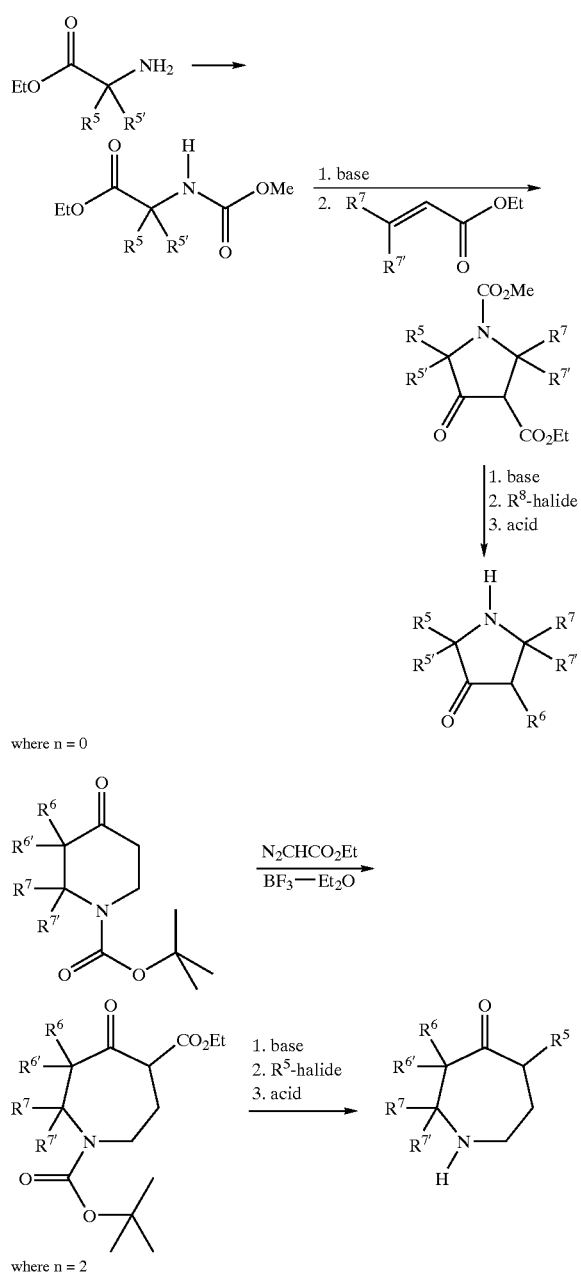

where n = 0 where n = 2

The requisite pyrrolidinones (n=0) may be prepared by reacting an ester, for example the ethyl ester, of an *-amino acid with methyl chloroformate. The resulting carbamate is treated with base and then with an appropriately substituted acrylic acid ester. The resulting *-keto ester is treated with base and an appropriate alkylating agent, such as an alkyl halide, followed by decarboxylation and deprotection in the presence of aqueous acid to provide the desired compound.

The requisite homopiperidinones may be prepared from the corresponding piperidine via standard ring expansion protocols employing ethyl diazoacetate and an appropriate Lewis acid, such as boron trifluoride. The resulting *-keto ester is treated with base and an appropriate alkylating agent, such as an alkyl halide, followed by decarboxylation and deprotection in the presence of aqueous acid to provide the desired compound. The skilled artisan will appreciate that subsequent transformations are possible, if necessary or desired, to prepare more highly substituted compounds.

The skilled artisan will appreciate that not all substituents are compatible with the reaction conditions employed to prepare the compounds of the invention. Those substituents incompatible with these conditions may be introduced at a more convenient point in the synthesis, or may be prepared by functional group transformations well known to one of ordinary skill in the art. Furthermore, many of the compounds of the present invention, while useful 5-$HT_{2C}$ agonists in their own right, are useful intermediates to prepare other compounds of the invention. Those compounds of the invention bearing an ester functionality, for example, may be hydrolyzed under standard conditions to provide the corresponding carboxylic acids. These acids may then be reacted with amines under standard peptide coupling conditions to provide the corresponding amides. Alternatively, the esters may be reduced to provide the corresponding alcohols. Furthermore, alkoxy groups may be cleaved to provide the corresponding phenols, and primary amines may be diazotized and displaced to provide the corresponding halogenated compounds.

The following Preparations and Examples are illustrative of methods useful for the synthesis of the compounds of the present invention.

Preparation I 5-fluoro-7-bromobenzofuran 2-(2-bromo-4-fluorophenoxy)acetaldehyde diethyl acetal To a solution of 20 gm (105 mMol) 2-bromo-4-fluorophenol in 211 mL dimethylformamide were added 15.8 mL (105 mMol) bromoacetaldehyde diethyl acetal followed by 14.5 gm (105 mMol) anhydrous potassium carbonate. This mixture was then heated at reflux for about 18 hours under a nitrogen atmosphere. The reaction mixture was then concentrated under reduced pressure and the resulting residue partitioned between 200 mL of ethyl acetate and 200 mL 1N sodium hydroxide. The phases were separated and the ethyl acetate phase was washed with 200 mL of water, giving rise to an emulsion. An additional 100 mL ethyl acetate and 20 mL of water were added to the emulsion. The separated ethyl acetate phase and emulsion were removed and saved. The ethyl acetate phase was washed again with 200 mL of water. This new emulsion was combined with the original emulsion and aqueous phase. The mixture was partitioned between 700 mL ethyl acetate and 780 mL of water. The emulsion and aqueous layer (1600 mL) were removed. The organic phase was dried over magnesium sulfate and concentrated under reduced pressure to provide 26.4 gm (82%) of the desired material as an amber oil. The reserved emulsion and aqueous phase was washed with 1 L of toluene. The phases were separated and organic phase was dried over magnesium sulfate and concentrated under reduced pressure to provide an additional 4.67 gm of the desired compound as an amber oil. Total recovery of desired product was 31.1 gm (96.7%).

Cyclization

A mixture of 109.4 gm Amberlyst-15 in 707 mL chlorobenzene was heated at reflux to remove water by azeotropic distillation. Distillate was removed until the volume remaining in the pot was about 500 mL. To this mixture was then added dropwise over 2 hours a solution of 109.4 gm (356 mMol) 2-(2-bromo-4-fluorophenoxy)acetaldehyde diethyl acetal in 4060 mL chlorobenzene. The mixture was stirred at reflux with constant water removal. When no more water was observed in the azeotrope distillate, the reaction mixture was cooled to room temperature. The filter cake was washed with 400 mL dichloromethane and the combined filtrates were concentrated under reduced pressure to provide 102 gm of a colorless oil. This oil was diluted with 500 mL hexane and subjected to silica gel chromatography, eluting with hexane. Fractions containing the desired product were combined and concentrated under reduced pressure to provide 39.6 gm (52%) of the title compound.

$^1$H-NMR(CDCl$_3$): δ7.75 (d, J=2.1 Hz, 1H), 7.27 (dd, JH,H=2.5 Hz, JH,F=8.8 Hz, 1H), 7.25 (dd, JH,H=2.5 Hz, JH,F=8.3 Hz, 1H), 6.85 (d, J=2.2 Hz, 1H).

Preparation II 4-methoxy-7-bromobenzofuran 2-bromo-5-methoxyphenol and 4-bromo-5-methoxyphenol A solution of 40.0 gm (322.2 mMol) 3-methoxyphenol in 1 L acetonitrile was cooled to 0° C. under a nitrogen atmosphere. To this cooled solution was added a solution of 57.35 gm (322.2 mMol) N-bromosuccinimide in 500 mL acetonitrile dropwise at a rate to maintain the temperature of the reaction mixture at 0° C. (approximately 2 hours). The reaction mixture was stirred at 0° C. for about 1 hour after the addition was complete and was then concentrated under reduced pressure. The residue was treated with carbon tetrachloride and the solid which formed was removed by filtration. The filtrate was concentrated under reduced pressure to provide a mixture of bromination isomers as a red oil.

This oil was subjected to silica gel chromatography, eluting with a gradient system of hexane containing from 0–30% ethyl acetate. Fractions containing the fastest eluting compound were combined and concentrated under reduced pressure to provide 18.1 gm (28%) of 2-bromo-5-methoxyphenol as a clear liquid.

$^1$H-NMR(CDCl$_3$): δ7.31 (d, 1H), 6.6 (d, 1H), 6.41 (dd, 1H), 5.5 (s, 1H), 3.77 (s, 3H).

Fractions containing the later eluting components were combined and concentrated under reduced pressure. This residue was subjected to silica gel chromatography, eluting with dichloromethane. Fractions containing substantially pure 4-bromo-5-methoxyphenol were combined and concentrated under reduced pressure to provide 24.1 gm (37%) of a white crystalline solid (m.p.=68–69° C.).

$^1$H-NMR(CDCl$_3$): δ7.34 (d, 1H), 6.45 (d, 1H), 6.33 (dd, 1H), 4.9 (br s, 1H), 3.85 (s, 3H).

2-(2-bromo-5-methoxyphenoxy)acetaldehyde diethyl acetal

A mixture of 16.0 gm (78.8 mMol) 2-bromo-5-methoxyphenol, 10.9 gm (78.8 mMol) potassium carbonate, and 15.5 gm (78.8 mMol) bromoacetaldehyde diethyl acetal in 300 mL dimethylformamide was heated at 142° C. for 16 hours. The reaction mixture was then cooled to room temperature and diluted with 100 mL 2N sodium hydroxide followed by 500 mL ethyl acetate. This mixture was washed twice with 1 L of water. The combined aqueous washes were extracted twice with 300 mL portions of ethyl acetate. All organic phases were combined, washed with 1 L of water, washed with 1 L of saturated aqueous sodium chloride, dried over magnesium sulfate and concentrated under reduced pressure to provide the desired compound as a dark amber oil.

Cyclization

A mixture of 17 gm polyphosphoric acid in 500 mL chlorobenzene was heated to 80° C. with stirring. To this mixture was added dropwise over 30 minutes a solution of 16 gm (50.13 mMol) 2-(2-bromo-5-methoxyphenoxy) acetaldehyde diethyl acetal in 100 mL chlorobenzene. The resulting mixture was stirred for 5 hours at 80° C. and 2 hours at 120° C. The reaction mixture was cooled to room temperature and the chlorobenzene solution was decanted from the polyphosphoric acid phase. The remaining residue was washed with five 200 mL portions of diethyl ether. All of the organic phases were combined and concentrated under reduced pressure to provide a dark amber oil. This oil was subjected to silica gel chromatography, eluting with a gradient of hexane containing from 0–5% ethyl acetate. Fractions containing product were combined and concentrated under reduced pressure to provide 11.3 gm (99%) of the title compound as a white, crystalline solid (m.p.= 60–62° C.).

EA: Calculated for C$_9$H$_7$BrO$_2$: Theory: C, 47.61; H, 3.11. Found: C, 47.40; H, 3.37.

Preparation III 5-bromo-6-methoxybenzofuran

Beginning with 23 gm (113.3 mMol) 4-bromo-5-methoxyphenol, 16.2 gm of the title compound were prepared as a white crystalline solid essentially by the procedure of Preparation II.

Preparation IV 4-bromobenzofuran and 6-bromobenzofuran 2-(3-bromophenoxy)acetaldehyde diethyl acetal A solution of 10 gm (57.8 mMol) 3-bromophenol in 25 mL dimethylformamide was added dropwise to a mixture of 2.8 gm (70 mMol) sodium hydride (60% suspension in mineral oil) in 30 mL dimethylformamide. The reaction mixture was stirred for one hour after the addition was complete. To the reaction mixture was then added 9.7 mL (64.5 mMol) bromoacetaldehyde diethyl acetal and the resulting mixture was stirred at 153° C. for 2 hours. The reaction mixture was then allowed to cool to room temperature and was diluted with 300 mL diethyl ether. This mixture was then washed with two 150 ml portions of water, washed with 50 mL saturated aqueous sodium chloride, dried over magnesium sulfate and concentrated under reduced pressure to provide about 17 gm of the desired compound.

$^1$H-NMR(CDCl$_3$): δ7.15–7.05 (m, 2H), 6.85 (dd, 1H), 4.8 (t, 1H), 3.95 (d, 2H), 3.8–3.55 (m, 4H), 1.25 (t, 6H).

Cyclization

A mixture of 17 gm (57.8 mMol) 2-(3-bromophenoxy) acetaldehyde diethyl acetal and 17.5 gm polyphosphoric acid in 400 mL chlorobenzene was heated to 80° C. for 2 hours. The reaction mixture was cooled to room temperature and the chlorobenzene was decanted from the polyphosphoric acid. The polyphosphoric acid was washed with two 150 mL portions of diethyl ether. All or the organic phases were combined and concentrated under reduced pressure. The residue was redissolved in diethyl ether and the organic phases were washed with saturated aqueous sodium bicarbonate, water, and saturated aqueous sodium chloride, dried over magnesium sulfate and concentrated under reduced pressure. The residual oil was subjected to silica gel chromatography, eluting with hexane.

Fractions containing the faster eluting isomer were combined and concentrated under reduced pressure to provide 1.7 gm (15%) 4-bromobenzofuran.

EA: Calculated for C$_8$H$_5$BrO: Theory: C, 48.77; H, 2.56. Found: C, 48.89; H, 2.72.

Fractions containing the slower eluting isomer were combined and concentrated under reduced pressure to provide 2.5 gm (22%) 6-bromobenzofuran.

EA: Calculated for C$_8$H$_5$BrO: Theory: C, 48.77; H, 2.56. Found: C, 48.89; H, 2.67.

Preparation V 5-bromobenzofuran

Beginning with 10 gm (57.8 mMol) 4-bromophenol, 4.2 gm (38%) of the title compound were prepared essentially by the procedure described in Preparation IV.

EA: Calculated for C$_8$H$_5$BrO: Theory: C, 48.77; H, 2.56. Found: C, 48.51; H, 2.46.

Preparation VI 7-bromobenzofuran

Beginning with 10 gm (57.8 mMol) 2-bromophenol, 5 gm (45%) of the title compound were prepared essentially by the procedure described in Preparation IV.

EA: Calculated for C$_8$H$_5$BrO: Theory: C, 48.77; H, 2.56. Found: C, 49.02; H, 2.82.

Preparation VII 5-methoxy-7-bromobenzofuran 2-bromo-4-methoxyphenol

A solution of 2.6 mL (100 mMol) bromine in 10 mL carbon disulfide was added dropwise over 30 minutes to a solution of 12.4 gm (100 mMol) 4-methoxyphenol in 20 mL carbon disulfide at 0° C. After 30 minutes an additional 1 mL of bromine in 10 mL carbon disulfide are added dropwise. The reaction mixture was then concentrated under reduced pressure and the residue was dissolved in diethyl ether. This solution was washed sequentially with 100 mL water and 100 mL saturated aqueous sodium chloride, dried over magnesium sulfate and concentrated under reduced pressure. The residue was subjected to silica gel chromatography, eluting with a gradient of hexane containing from 0 to 20% ethyl acetate. Fractions containing product were combined and concentrated under reduced pressure to provide 11.6 gm (57%) of the desired compound as a crystalline solid.

$^1$H-NMR(CDCl$_3$): δ7.0 (d, 1H), 6.95 (d, 1H), 6.8 (dd, 1H), 5.15 (s, 1H), 3.75 (s, 3H).

Beginning with 11.5 gm (56.9 vol) 2-bromo-4-methoxyphenol, 4.5 gm (35%) of the title compound were prepared essentially by the procedure described in Preparation IV.

EA: Calculated for C$_9$H$_7$BrO$_2$: Theory: C, 47.61; H, 3.11. Found: C, 47.79; H, 3.13.

Preparation VIII 6-methoxy-7-bromobenzofuran 2-bromo-3-methoxyphenol

A solution of 22 gm (177.4 mMol) 3-methoxyphenol in 30 mL dihydropyran was added dropwise to a solution of 100 mg (0.525 mMol) p-toluenesulfonic acid monohydrate in 10 mL dihydropyran while cooling in an ice/water bath. After stirring for 1 hour the reaction mixture was diluted with 300 mL diethyl ether and then washed sequentially with 100 mL 0.1 N sodium hydroxide and 100 mL saturated aqueous sodium chloride. The remaining organic phase was dried over magnesium sulfate and concentrated under reduced pressure. The resulting oil was distilled. The fraction distilling at 110–130° C. was collected and then partitioned between 5 N sodium hydroxide and diethyl ether. The organic phase was separated, washed sequentially with water and saturated aqueous sodium chloride, dried over magnesium sulfate and concentrated under reduced pressure to provide 27.1 gm (73%) of tetrahydropyran-2-yl 3-methoxyphenyl ether.

$^1$H-NMR(CDCl$_3$): δ7.18 (t, 1H), 6.65–6.60 (m, 2H), 6.50 (dd, 1H), 5.4 (t, 1H), 3.95–3.90 (m, 1H), 3.80 (s, 3H), 3.62–3.55 (m, 1H), 2.0–1.6 (m, 6H).

33 mL (52.8 mMol) n-butyllithium (1.6 M in hexane) were added dropwise to a solution 10 gm (48.1 mMol) tetrahydropyran-2-yl 3-methoxyphenyl ether in 100 mL tetrahydrofuran over 15 minutes. After stirring for 2.5 hours at room temperature, the reaction mixture was cooled to 0° C. and then 4.6 mL (53.2 mMol) 1,2-dibromoethane were added dropwise. The reaction mixture was then allowed to stir at room temperature for about 14 hours. The reaction mixture was then diluted with 50 mL 1 N hydrochloric acid and was stirred for 1 hour. The aqueous phase was extracted with three 100 mL portions of diethyl ether. The organic phases were combined and extracted well with 5 N sodium hydroxide. These basic aqueous extracts were combined and cooled in an ice/water bath. The pH of this aqueous solution was adjusted to about 1 with 5 N hydrochloric acid and then extracted with three 100 mL portions of diethyl ether. These ether extracts were combined and washed with saturated aqueous sodium chloride, dried over magnesium sulfate and concentrated under reduced pressure. The resulting residue was subjected to silica gel chromatography, eluting with a gradient of hexane containing from 0 to 10% ethyl acetate. Fractions containing the desired compound were combined and concentrated under reduced pressure to provide 2.91 gm (30%) of a residue which crystallized upon standing.

EA: Calculated for C$_7$H$_7$BrO$_2$: Theory: C, 41.41; H, 3.48. Found: C, 41.81; H, 3.46.

Beginning with 6.9 gm (34 mMol) 2-bromo-3-methoxyphenol, 3.2 gm (41%) of the title compound were prepared as a white fluffy solid essentially by the procedure described in Preparation IV.

High Resolution MS: Calculated for C$_9$H$_7$BrO$_2$: Theory: 225.9629. Found: 225.9626.

Preparation IX 4-fluoro-7-bromobenzofuran

Beginning with 5 gm (26 mMol) 2-bromo-5-fluorophenol and 6.5 gm (39 mMol) bromoacetaldehyde ethylene glycol acetal, 3.3 gm (59%) of the title compound were prepared essentially by the procedure described in Preparation IV.

EA: Calculated for C$_8$H$_4$BrFO: Theory: C, 44.69; H, 1.88. Found: C, 44.44; H, 1.91.

Preparation X 5-bromo-7-fluorobenzofuran

Beginning with 20.5 gm (108 mMol) 2-fluoro-4-bromophenol, 3.0 gm (13%) of the title compound were prepared essentially by the procedure described in Preparation I.

$^1$H-NMR(CDCl$_3$): δ7.65 (d, J=2.4 Hz, 1H), 7.50 (d, J=1.5 Hz, 1H), 7.19 (dd, J$_H$=1.5 Hz, J$_F$=8.3 Hz, 1H), 6.76 (m, 1H).

Preparation XI 6-fluoro-7-bromobenzofuran

Beginning with 7.5 gm (39.3 mMol) 2-bromo-3-fluorophenol, 10.83 gm (90%) 2-(2-bromo-3-fluorophenoxy)acetaldehyde diethyl acetal was prepared essentially as described in Preparation IV.

Beginning with 5.0 gm (16.3 mMol) of 2-(2-bromo-3-fluorophenoxy)acetaldehyde diethyl acetal, 2.2 gm (63%) of the title compound were prepared essentially as described in Preparation IV.

Preparation XII

5-chloro-7-bromobenzofuran

Beginning with 25 gm (120.5 mMol) 2-bromo-4-chlorophenol, 41.16 gm crude 2-(2-bromo-4-chlorophenoxy)acetaldehyde diethyl acetal was prepared essentially as described in Preparation IV. A sample of this crude material was subjected to silica gel chromatography to provide an analytical sample.

EA: Calculated for $C_{12}H_{16}BrClO_3$: Theory: C, 44.54; H, 4.98. Found: C, 44.75; H, 4.97.

Beginning with 20 gm (61.8 mMol) of 2-(2-bromo-4-chlorophenoxy)acetaldehyde diethyl acetal, 4.48 gm (31%) of the title compound were prepared as a crystalline solid essentially as described in Preparation I.

EA: Calculated for $C_8H_4BrClO$: Theory: C, 41.51; H, 1.74. Found: C, 41.67; H, 1.78.

Preparation XIII

4,5-difluoro-7-bromobenzofuran

Beginning with 5 gm (23.9 mMol) 2-bromo-4,5-difluorophenol, 7.05 gm (91%) 2-(2-bromo-4,5-difluorophenoxy)acetaldehyde diethyl acetal were prepared essentially as described in Preparation IV.

EA: Calculated for $C_{12}H_{15}BrF_2O_3$: Theory: C, 44.33; H, 4.65. Found: C, 44.34; H, 4.41.

Beginning with 6.60 gm (20.3 mMol) of 2-(2-bromo-4,5-difluorophenoxy)acetaldehyde diethyl acetal, 0.42 gm (9%) of the title compound were prepared as a crystalline solid essentially as described in Preparation I.

EA: Calculated for $C_8H_3BrF_2O$: Theory: C, 41.24; H, 1.30. Found: C, 41.20; H, 1.51.

Preparation XIV

3-methyl-5-fluoro-7-bromobenzofuran

1-(2-bromo-4-fluorophenoxy)-2-propanone

A mixture of 1.9 gm (10 mMol) 2-bromo-4-fluorophenol, 0.92 gm (10 mMol) chloroacetone, 0.1 gm potassium iodide, and 1.4 gm (10 mMol) potassium carbonate in 100 mL tetrahydrofuran was heated at reflux for 4 hours. The mixture was concentrated under reduced pressure and the residue partitioned between dichloromethane and 1 N sodium hydroxide. The phases were separated and the aqueous phase extracted well with dichloromethane. The organic phases were combined, washed with 1 N sodium hydroxide, dried over sodium sulfate and concentrated under reduced pressure. The residual was subjected to silica gel chromatography, eluting with hexane containing 20% ethyl acetate. Fractions containing product were combined and concentrated under reduced pressure to provide 2.7 gm (100%) of the desired compound as a white solid.

Cyclization

Beginning with 2.7 gm (10 mMol) 1-(2-bromo-4-fluorophenoxy)-2-propanone and 15 gm polyphosphoric acid, 2.03 gm (81%) of the title compound were prepared as a yellow crystalline solid essentially as described in Preparation II.

Preparation XV

2-methyl-5-fluoro-7-bromobenzofuran

Ethyl 2-(2-bromo-4-fluorophenoxy)propionate

A mixture of 15 gm (78.5 mMol) 2-bromo-4-fluorophenol, 11.2 mL (86.4 mMol) ethyl 2-bromopropionate, and 13 gm (94.2 mMol) potassium carbonate was heated at reflux for 3 hours. At this point 0.1 gm potassium iodide were added and reflux continued for another 2 hours. The reaction mixture was partitioned between water and ethyl acetate. The phases were separated and the aqueous phase was extracted well with ethyl acetate. The organic phases were combined, washed with saturated aqueous sodium chloride, dried over sodium sulfate, and concentrated under reduced pressure. The residue was subjected to silica gel chromatography, eluting with hexane containing 5% ethyl acetate. Fractions containing product were combined and concentrated under reduced pressure to provide 19.8 gm (87%) of the desired compound as a clear oil.

2-(2-bromo-4-fluorophenoxy)propionaldehyde

A solution of 19.4 gm (66.7 mMol) ethyl 2-(2-bromo-4-fluorophenoxy)propionate in 400 mL toluene was cooled to −78° C. at which point 100 mL (100 mMol) diisobutylaluminum hydride (1 M in toluene) were added dropwise over 35 minutes. The reaction mixture was stirred at −78° C. for an additional 20 minutes after the addition was complete and then the reaction was quenched by the addition of methanol. The reaction mixture was warmed to room temperature and then treated with saturated aqueous sodium potassium carbonate. The mixture was stirred for 30 minutes and was then extracted well with ethyl acetate. The organic phases were combined, dried over sodium sulfate, and concentrated under reduced pressure to provide 16.9 gm of crude desired compound.

Cyclization

Beginning with 16.5 gm of the crude aldehyde, 5.2 gm (34% for the reduction and cyclization) of the title compound were prepared essentially as described in Preparation II.

Preparation XVI

5-nitro-7-bromobenzofuran

Potassium 5-nitro-7-bromobenzofuran-2-carboxylate

A mixture of 11.0 gm (44.7 mMol) 2-hydroxy-3-bromo-5-nitrobenzaldehyde, 5.56 gm (40.24 mMol) potassium carbonate, and 8.0 mL (46.95 mMol) diethyl bromomalonate in 55 mL 2-butanone was heated at reflux for 5 hours. The reaction mixture was cooled to room temperature and concentrated under reduced pressure. The residue was partitioned between 450 mL diethyl ether and 250 mL water and the aqueous phase was adjusted to pH of about 1 by the addition of dilute sulfuric acid. The phases were separated and the aqueous phase was extracted with two 150 mL portions of diethyl ether. The organic phases were combined, washed with 50 mL saturated aqueous sodium chloride, dried over magnesium sulfate and concentrated under reduced pressure. The residual solid was dissolved in 200 mL ethanol to which were added 4.8 gm (85.5 mMoL) potassium hydroxide. The resulting suspension was warmed on a steam bath for 1 hour. The suspension was then cooled to room temperature. After about 18 hours the mixture was filtered and dried under reduced pressure to provide 14.1 gm (98%) of the desired compound as an orange solid.

$^{13}$C-NMR(DMSO-$d_6$): δ160.3, 159.8, 154.0, 143.9, 129.7, 122.2, 117.7, 108.0, 103.8.

5-nitro-7-bromobenzofuran-2-carboxylic acid

A mixture of 11.5 gm (35.5 mMol) potassium 5-nitro-7-bromobenzofuran-2-carboxylate and 36 gm Dowex 50WX8-200 resin in 1.6 L methanol was stirred for 1 hour at room temperature. The mixture was filtered and the filtrate concentrated under reduced pressure. The residue was diluted with about 80 mL of methanol and heated on the steam bath with stirring. The mixture was cooled to room temperature and filtered. The residual solid was dried under vacuum to provide 6.7 gm (66%) of the desired compound as a gold solid.

m.p.=257° C. (dec.)

MS(FD): m/e=285, 287 ($M^+$)

EA: Calculated for $C_9H_4NO_5Br$: Theory: C, 37.79; H, 1.41; N, 4.90. Found: C, 37.81; H, 1.55; N, 4.77.

Decarboxylation

A sonicated mixture of 0.42 gm (1.47 mMol) 5-nitro-7-bromobenzofuran-2-carboxylic acid and 0.085 gm copper powder in 10 mL freshly distilled quinoline was heated at 185° C. under nitrogen for 7 minutes. The reaction mixture was cooled to room temperature and filtered. The solid recovered was washed with two 20 mL portions of dichloromethane and these washes were combined with the filtrate. The filtrate was then diluted with 70 mL dichloromethane and was washed sequentially with two 100 mL portions of 1 N hydrochloric acid, and 50 mL 4:1 saturated aqueous sodium chloride:5 N sodium hydroxide. The remaining organics were dried over sodium sulfate and concentrated under reduced pressure. The residue was subjected to silica gel chromatography, eluting with hexane containing 10% ethyl acetate. Fractions containing product were combined and concentrated under reduced pressure. The residual solid was crystallized from hexane to provide 0.15 gm (42%) of the title compound as fine, light orange needles.

m.p.=90–92° C.

MS(FD): m/e=241, 243 ($M^+$)

EA: Calculated for $C_8H_4NO_3Br$: Theory: C, 39.70; H, 1.67; N, 5.79. Found: C, 40.05; H, 2.03; N, 5.67.

Preparation XVII 3-trifluoromethyl-5-fluoro-7-bromobenzofuran

A solution of 2.10 gm (16.7 mMol) 1-trifluoromethylprop-1-en-3-ol, 3.19 gm (16.7 mMol) 2-bromo-4-fluorophenol, and 4.81 gm (18.4 mMol) triphenylphosphine in 25 mL dichloromethane was cooled to 0° C. and then 2.9 mL (18.4 mMol) diethyl azodicarboxylate were added. The reaction mixture was stirred for 1 hour at room temperature and then the reaction mixture was directly subjected to flash silica gel chromatography, eluting with 20:1 hexane:ethyl acetate. Fractions containing product were combined and concentrated under reduced pressure to provide 6 gm of crude 1-(1-trifluoromethylprop-1-en-3-yloxy)-2-bromo-4-fluorobenzene.

1.0 gm (3.34 mMol) 1-(1-trifluoromethylprop-1-en-3-yloxy)-2-bromo-4-fluorobenzene was heated at 250° C. for 3 hours. The reaction mixture, containing primarily 2-(3-trifluoromethylprop-1-en-3-yl)-4-fluoro-6-bromophenol, was diluted with dichloromethane and the solution cooled to −78° C. This solution was then treated with excess ozone and was stirred at −78° C. until the 2-(3-trifluoromethylprop-1-en-3-yl)-4-fluoro-6-bromophenol was consumed as measured by thin layer chromatography. At this point the ozone was purged from the reaction with oxygen and then 0.88 gm (3.34 mMol) triphenylphosphine were added. The mixture was stored at −20° C. for about 64 hours. The reaction mixture was then concentrated under reduced pressure and the residue subjected to flash silica gel chromatography, eluting with hexane containing 10% ethyl acetate. Fractions containing the desired compound were combined and concentrated under reduced pressure to provide 2-hydroxy-3-trifluoromethyl-5-fluoro-7-bromo-2,3-dihydrobenzofuran. A solution of this dihydrobenzofuran in 10 mL toluene was treated with 4 drops of sulfuric acid and was stirred at reflux for 10 minutes. The reaction mixture was cooled to room temperature and was then washed with saturated aqueous sodium bicarbonate. The organic phase was separated and concentrated under reduced pressure. The residue was subjected to flash silica gel chromatography, eluting with hexane. Fractions containing product were combined and concentrated under reduced pressure to provide the title compound.

Preparation XVIII 5-methoxycarbonyl-7-bromobenzofuran

Beginning with methyl 3-bromo-4-allyloxybenzoate, the title compound was prepared essentially as described in Preparation XVII.

Preparation XIX 3-ethyl-5-fluoro-7-bromobenzofuran

Beginning with pent-2-en-1-yl 2-bromo-4-fluorophenyl ether, the title compound was prepared essentially as described in Preparation XVII, except that Amberlyst 15™ resin in refluxing toluene was used in place of sulfuric acid, and water was removed by azeotropic distillation with a Dean-Stark trap.

Preparation XX 3-isopropyl-5-fluoro-7-bromobenzofuran

Beginning with 4-methylpent-2-en-1-yl 2-bromo-4-fluorophenyl ether, the title compound was prepared essentially as described in Preparation XIX.

Preparation XXI 3,4-dimethyl-5-fluoro-7-bromobenzofuran

Beginning with but-2-en-1-yl 2-bromo-4-fluoro-5-methylphenyl ether, the title compound was prepared essentially as described in Preparation XVII.

Preparation XXII 4-chloro-5-fluoro-7-bromobenzofuran

Bromination

A mixture of 5 gm (34.1 mMol) 3-chloro-4-fluorophenol and 1.76 mL (34.1 mMol) bromine in 20 mL carbon disulfide was stirred at room temperature for 18 hours. The reaction mixture was concentrated under reduced pressure and the residue was dissolved in dichloromethane, washed with water, dried over sodium sulfate and concentrated under reduced pressure to provide a mixture of 2-bromo-4-fluoro-5-chlorophenol and 2-bromo-3-chloro-4-fluorophenol.

Ether Formation

This mixture of bromination isomers was combined with 12 gm allyl bromide and 13.6 gm potassium carbonate in 90 mL dimethylformamide. After stirring at room temperature for 2.5 hours, the mixture was partitioned between dichloromethane and water. The organic phases were combined, dried over sodium sulfate and concentrated under reduced pressure to provide 9.7 gm of a mixture of allyl ether isomers.

Rearrangement/ozonolysis/dehydration

The mixture of allyl ethers was reacted as described in Preparation XVII to provide 0.49 gm of the title compound as a white crystalline solid.

m.p.=84–85° C.

$^1$H-NMR(300 MHz, CDCl$_3$): δ7.73 (d, J=2.1 Hz, 1H); 7.29 (d, J=8.8 Hz, 1H); 6.92 (d, J=2.1 Hz, 1H).

Preparation XXIII 4-trifluoromethyl-7-bromobenzofuran and 6-trifluoromethyl-7-bromobenzofuran 4-Trifluoromethylphenol was brominated essentially as described in Preparation XXII to provide a 58:12:30 mixture of 2-bromo-5-trifluoromethylphenol:2-bromo-3-trifluoromethylphenol:4-bromo-3-trifluoromethylphenol. The 4-bromo-3-trifluoromethylphenol was separated from the other two isomers by silica gel chromatography. The remaining mixture of isomers was then alkylated to provide a mixture of 2-bromo-5-trifluorophenyl allyl ether and 2-bromo-3-trifluoromethylphenylallyl ether which was then separated by chromatography.

The 2-bromo-5-trifluoromethylphenyl allyl ether was converted to 4-trifluoromethyl-7-bromobenzofuran essentially as described in Preparation XXII.

$^1$H-NMR(300 MHz, CDCl$_3$): δ7.81 (d, J=2.0 Hz, 1H); 7.55 (d, J=8.3 Hz, 1H); 7.41 (d, J=8.3 Hz, 1H); 7.03 (m, 1H).

The 2-bromo-3-trifluoromethylphenyl allyl ether was converted to 6-trifluoromethyl-7-bromobenzofuran essentially as described in Preparation XXII.

$^1$H-NMR(300 MHZ, CDCl$_3$): δ7.83 (d, J=1.9 Hz, 1H); 7.61 (d, J=8.3 Hz, 1H); 7.57 (d, J=8.3 Hz, 1H); 6.91 (d, J=1.9 Hz, 1H).

Preparation XXIV 5-trifluoromethyl-7-bromobenzofuran

Beginning with 5-trifluoromethylphenol, the title compound was prepared essentially as described in Preparation XXII.

Preparation XXV 4,5,6-trifluoro-7-bromobenzofuran

Beginning with 3,4,5-trifluorophenol, the title compound was prepared essentially as described in Preparation XXII.

Preparation XXVI 4,6-dimethyl-5-chloro-7-bromobenzofuran

Beginning with 3,5-dimethyl-4-chlorophenol, the title compound was prepared essentially as described in Preparation XXII.

Preparation XXVII

Alternate Synthesis of 4,5-difluoro-7-bromobenzofuran 2-bromo-4,5-difluorophenyl allyl ether A mixture of 79.4 gm (0–38 mole) 2-bromo-4,5-difluorophenol and 79 gm (0.57 mole) potassium carbonate in 200 mL dimethylformamide was stirred at room temperature for 30 minutes. At this point 33 mL (0.38 mMol) allyl bromide were added and the resulting mixture was stirred for 18 hours at room temperature. The reaction mixture was then diluted with diethyl ether and washed with water followed by saturated aqueous sodium chloride. The remaining organics were dried over magnesium sulfate and concentrated under reduced pressure to provide 90 gm (96%) of the desired compound.

2-allyl-3,4-difluoro-6-bromophenol 15 gm (60.5 mMol) 2-bromo-4,5-difluorophenyl allyl ether was heated at 200° C. for 2 hours under a nitrogen atmosphere. The reaction mixture was cooled to room temperature and filtered through a pad of celite. The celite pad was washed with 500 mL hexane and the filtrate concentrated under reduced pressure. The residue was subjected to flash silica gel chromatography, eluting with hexane. Fractions containing product were combined and concentrated under reduced pressure to provide 9.7 gm (65%) of the desired compound.

(2-hydroxy-3-bromo-5,6-difluorophenyl) acetaldehyde

A solution of 7.8 gm (31.45 mMol) 2-allyl-3,4-difluoro-6-bromophenol in 100 mL dichloromethane and 20 mL methanol was cooled to −78° C. and was then saturated with ozone. After 20 minutes the reaction mixture was purged with nitrogen for 10 minutes and was then treated with 5 mL dimethylsulfide. The reaction mixture was allowed to warm gradually to room temperature. After 15 hours the reaction mixture was concentrated under reduced pressure to provide the title compound.

Cyclization

A mixture of 7.5 gm Amberlyst 15™ resin in 150 mL chlorobenzene was heated at 160° C. and the solvent distilled to remove water. The reaction mixture was cooled to 120° C. and then a solution of 31.45 mMol (2-hydroxy-3-bromo-5,6-difluorophenyl)acetaldehyde in chlorobenzene was added dropwise. The temperature was again increased to 160° C. and solvent distilled. After 1.5 hours, the reaction mixture was filtered and the filtrate concentrated under reduced pressure. The residue was subjected to silica gel chromatography, eluting with hexane. Fractions containing product were combined and concentrated under reduced pressure to provide 3.9 gm (53%) of the title compound as a white solid.

m.p.=46.5–48° C.

Preparation XXVIII 5-hydroxymethyl-7-bromobenzofuran

A solution of 0.63 gm (2.46 mMol) 5-methoxycarbonyl-7-bromobenzofuran in 10 mL toluene was cooled to −78° C. When material precipitated, 5 mL dichloromethane were added to effect solution. To this solution were then slowly added 1.5 mL (8.6 mMol) diisobutylaluminum hydride and the reaction mixture was allowed to warm gradually to room temperature. After 10 minutes the reaction was quenched by the addition of methanol followed by 1.5 gm sodium fluoride and 50 mL water and then Rochelle's salt solution. The mixture was diluted with additional dichloromethane and was stirred vigorously for about 1 hour. The phases were separated and the aqueous phase extracted well with ethyl acetate. The organic phases were combined and concentrated under reduced pressure. The residue was crystallized from hexane and dichloromethane to provide 0.46 gm (82%) of the title compound as a white crystalline solid.

Preparation XXIX 5-methoxymethyl-7-bromobenzofuran

A solution of 0.372 gm (0.40 mMol) 5-hydroxymethyl-7-bromobenzofuran in tetrahydrofuran was added to a mixture of 1.80 mMol sodium hydride (60% suspension in mineral oil) in 2 mL tetrahydrofuran. After stirring at room temperature for 1 hour, 204 μL iodomethane were added and stirring was continued for 2.5 hours. The reaction mixture was quenched by the addition of water and the resulting mixture was extracted well with ethyl acetate. The organic phase was concentrated under reduced pressure to provide a nearly quantitative yield of the title compound.

Preparation XXX

5-carboxy-7-bromobenzofuran

A solution of 0.52 gm (2.03 mMol) 5-methoxycarbonyl-7-bromobenzofuran and 0.41 gm (10.13 mMol) sodium hydroxide in 4 mL ethanol was stirred at room temperature until all of the starting material had been consumed. The reaction mixture was concentrated under reduced pressure and the residue dissolved in water. This solution was then made basic by the addition of 1N sodium hydroxide and was extracted well with ethyl acetate. The remaining aqueous phase was made acidic (pH about 2) by treatment with potassium hydrogen sulfate and the resulting solid removed by filtration. The aqueous phase was extracted well with ethyl acetate and the organics were combined and concentrated under reduced pressure to provide 0.40 gm (82%) of 5-carboxy-7-bromobenzofuran as an off-white solid.

MS(FD): m/e=240 (M−1)

Preparation XXXI

4-bromo-5-fluoro-, and 5-fluoro-6-bromobenzofuran

O-acetyl 3-bromo-4-fluorophenol

A solution of 1.09 gm (5 mMol) 3-bromo-4-fluoroacetophenone and 3.45 gm (20 mMol) m-chloroperbenzoic acid (70%) in 15 mL dichloromethane was heated at reflux for 18 hours. An additional 3.45 gm m-chloroperbenzoic acid were added and reflux continued for about 12 hours. At this point an additional 1.4 gm m-chloroperbenzoic acid were added and reflux continued for 18 hours. The reaction mixture was cooled to room temperature and was then diluted with 50 mL diethyl ether. The resulting mixture was cooled to 0° C. and was then treated with 15 mL 20% aqueous sodium thiosulfate. The resulting slurry was stirred for about 1 hour and then the phases separated. The organic phase was washed sequentially with 3×20 mL 20% aqueous sodium thiosulfate followed by 3×20 mL saturated aqueous sodium chloride. The organic phase was then dried over sodium sulfate and concentrated under reduced pressure. The residue was subjected to silica gel chromatography, eluting with 10:1 hexane:diethyl ether. Fractions containing product were combined and concentrated under reduced pressure to provide 68% of the desired compound.

3-bromo-4-fluorophenol

A solution of 0.80 gm (3.43 mMol) O-acetyl 3-bromo-4-fluorophenol in 10 mL 6% diisopropylethylamine in methanol was stirred at room temperature for 8 hours. The reaction mixture was concentrated under reduced pressure at 0° C. to provide the desired compound.

3-bromo-4-fluorophenyl allyl ether

A mixture of 0.65 gm (3.43 mMol) 3-bromo-4-fluorophenol, 0.60 mL (6.86 mMol) allyl bromide, and 0.71 gm (5.15 mMol) potassium carbonate in 6 mL acetone was stirred at reflux for 13 hours. The reaction mixture was concentrated under reduced pressure and the residue subjected to silica gel chromatography, eluting with hexane. Fractions containing product were combined and concentrated under reduced pressure to provide 61% of the desired compound.

Claisen Rearrangement 3-bromo-4-fluorophenyl allyl ether was placed in a sealed tube and was deoxygenated by bubbling nitrogen through the liquid. The tube was sealed and then heated at 230° C. for 3 hours. After cooling to room temperature, the mixture is subjected to silica gel chromatography, eluting with 8:1 hexane:diethyl ether. The faster eluting product isomer was 2-allyl-4-fluoro-5-bromophenol. The slower eluting isomer was 2-allyl-3-bromo-4-fluorophenol. The isomers were isolated in a ratio of 3:2 respectively.

4-bromo-5-fluorobenzofuran

Beginning with 3 gm (13 mMol) 2-allyl-3-bromo-4-fluorophenol, the title compound was prepared in 98% yield essentially by the procedure described in Preparation XXVII with the exception that the cyclization/dehydration step was performed using sulfuric acid in toluene.

5-fluoro-6-bromobenzofuran

Beginning with 3.5 gm (15 mMol) 2-allyl-4-fluoro-5-bromophenol, the title compound was prepared in 90% yield essentially by the procedure described in Preparation XXXI with the exception that the cyclization/dehydration step was performed using sulfuric acid in toluene.

Preparation XXXII

Alternate Synthesis of 4-chloro-5-fluoro-7-bromobenzofuran

A mixture of 90.4 gm (0.40 mole) 2-bromo-4-fluoro-5-chlorophenol (containing 10% 2-bromo-3-chloro-4-fluorophenol) and 64 gm (0.45 mole) hexamethylenetetramine was cooled in an ice bath. To this cooled mixture were added 306 mL trifluoroacetic acid. After stirring at about 0° C. for 15 minutes, the reaction mixture was heated at reflux for 1.5 hours. The reaction mixture was then cooled in an ice bath and treated with 439 mL of water followed by 220 mL 50% sulfuric acid. The reaction mixture was stirred without cooling for two hours. The reaction mixture was then diluted with 500 mL water and the resulting solid collected by filtration. The solid was washed with water until the wash was neutral (pH about 7). The solid was dried under reduced pressure and was then subjected to silica gel chromatography, eluting with a gradient of hexane containing from 0–2% ethyl acetate. Fractions containing the desired compound were combined and concentrated under reduced pressure to provide 57 gm (62%) 2-hydroxy-3-bromo-5-fluoro-6-chlorobenzaldehyde.

A suspension of 49.2 gm (0.19 mole) 2-hydroxy-3-bromo-5-fluoro-6-chlorobenzaldehyde and 127 gm (0.29 mole) (bromomethyl)triphenylphosphonium bromide in 230 mL tetrahydrofuran was cooled to 0° C. under a nitrogen atmosphere. To this were added dropwise 330 mL (0.33 mole) potassium tert-butoxide (1M in tetrahydrofuran) over 3 hours. An additional 90 mL (0.09 mole) potassium tert-butoxide (1M in tetrahydrofuran) were then added to react remaining starting material. The reaction mixture was diluted with 700 mL of hexane and the resulting precipitate removed by filtration. The recovered solid was slurried in 300 mL hexane and filtered 4 times. The combined filtrates were washed with 2×500 mL water followed by 500 mL saturated aqueous sodium chloride. The remaining organics were dried over sodium sulfate and concentrated under reduced pressure to provide a residual solid. This solid was slurried and filtered with 4×300 mL diethyl ether to remove triphenylphosphine oxide. The filtrates were concentrated and the residue subjected to silica gel chromatography, eluting with hexane. Fractions containing product were combined and concentrated under reduced pressure to provide 40 gm (83%) of the title compound as a white solid.

Preparation XXXIII

1-benzyl-3-ethyl-4-oxopiperidine

Methyl 1-tert-butoxycarbonyl-4-oxo-3-piperidinecarboxylate

A mixture of 20 gm (103.3 mMol) methyl 4-oxo-3-piperidinecarboxylate hydrochloride and 75 mL saturated aqueous sodium bicarbonate in 150 mL dichloromethane was stirred vigorously at room temperature. A solution of 24.8 gm (113.6 mMol) di-tert-butyl dicarbonate in 100 mL dichloromethane was then added dropwise over three hours. After stirring at room temperature for about 16 hours, an additional 3.0 gm di-tert-butyl dicarbonate were added and stirring continued for an additional 2 hours. The reaction mixture was then diluted with water and extracted with 2×250 mL dichloromethane. The organic phases were combined, dried over magnesium sulfate, and concentrated under reduced pressure to provide 26.2 gm (99%) of the desired compound as a yellow oil.

Methyl 1-tert-butoxycarbonyl-4-oxo-3-ethyl-3-piperidinecarboxylate

A solution of 26 gm (101 mMol) methyl 1-tert-butoxycarbonyl-4-oxo-3-piperidinecarboxylate and 11.9 gm (106 mMol) potassium tert-butoxide in 300 mL tert-butanol was heated to 70° C. under nitrogen. To this solution were then added 23.6 gm (152 mMol) iodoethane over 20 minutes, and the reaction mixture was heated at reflux for about 16 hours. The reaction mixture was then cooled to room temperature and was diluted with diethyl ether. The organics were washed with water, dried over magnesium sulfate, and concentrated under reduced pressure to provide 28.7 gm (99%) of the desired compound as a yellow oil.

3-ethyl-4-oxopiperidine hydrochloride

A mixture of 28.2 gm (98.8 mMol) methyl 1-tert-butoxycarbonyl-4-oxo-3-ethyl-3-piperidinecarboxylate and 6N hydrochloric acid was heated at reflux for about 16 hours. The reaction mixture was concentrated under reduced pressure and the residue dissolved in ethanol. This solution was concentrated under reduced pressure to azeotropically remove water. This procedure was repeated twice to provide 7.0 gm (55%) of the desired compound.

Benzylation

A mixture of 7.0 gm (54.8 mMol ) 3-ethyl-4-oxopiperidine and 22.7 gm (164.4 mMol) potassium carbonate in 100 mL tetrahydrofuran was cooled to 0° C. with vigorous stirring. A solution of 9.2 gm (53.7 mMol) benzyl bromide in 20 mL tetrahydrofuran was added dropwise over 20 minutes. The reaction mixture was then allowed to warm gradually to room temperature. After about 16 hours the reaction mixture was diluted with water and was extracted with 2×250 mL dichloromethane. The organic phases were combined, dried over magnesium sulfate and concentrated under reduced pressure. The residue was subjected to silica gel chromatography, eluting with a gradient of hexane containing from 5–15% ethyl acetate. Fractions containing product were combined and concentrated under reduced pressure to provide 9.4 gm (79%) of the title compound as a light yellow oil.

Preparation XXXIV

1-benzyl-3,3-dimethyl-4-oxopiperidine

Methyl N-[benzyl]3-aminopropionate

A solution of 55 mL (0.50 mole) benzylamine in 250 mL methanol was cooled in an ice bath. A solution of 54 mL (0.60 mole) methyl acrylate in 50 mL methanol was added dropwise over 30 minutes. The reaction mixture was then allowed to warm gradually to room temperature. After about 96 hours the reaction mixture was concentrated under reduced pressure and the residue vacuum distilled to provide 74.6 gm (77%) of the desired compound in two fractions.

Methyl N-[benzyl]-N-[methyl malonoyl]3-aminopropionate 144 mL (1.25 mole) dimethyl malonate was heated at from 165–175° C. To this heated substrate was added 48.6 gm (0.25 mole) methyl N-[benzyl]3-aminopropionate dropwise. Methanol was distilled off as the reaction proceeded. After 8.0 mL of methanol was recovered, the temperature of the reaction mixture was increased to 180–185° C. After 1 hour at this temperature, an additional 1.5 mL of methanol had been recovered. The reaction mixture was then cooled to room temperature and the excess dimethyl malonate was removed by vacuum distillation. The residue was subjected to silica gel chromatography, eluting with a gradient of hexane containing from 0–50% ethyl acetate. Fractions containing the desired product were combined and concentrated under reduced pressure to provide 55.7 gm (76%).

Methyl 1-benzyl-2,4-dioxo-3-piperidinecarboxylate

A mixture of 130 gm (0.94 mole) potassium carbonate and 5 gm (18.9 mMol) 18-crown-6 in 500 mL toluene was heated at reflux. A solution of 55 gm (188 mMol) methyl N-[benzyl]-N-[methyl malonoyl]3-aminopropionate in 150 mL toluene was added dropwise over 30 minutes. After 6 hours the reaction mixture was cooled to room temperature and then diluted with 1 L water. The toluene phase was diluted with 150 mL ethyl acetate and the phases separated. The organic phase was extracted with 2×250 mL water. The combined aqueous phases were cooled in an ice bath as 6N hydrochloric acid was added until pH<1. The aqueous phase was then extracted with 3×300 mL dichloromethane. The combined dichloromethane extracts were dried over magnesium sulfate and concentrated under reduced pressure to provide 23.4 gm (48%) of the desired compound. The toluene/ethyl acetate extract was washed with saturated aqueous sodium chloride and then concentrated under reduced pressure to provide 26.1 gm (47%) unreacted methyl N-[benzyl]-N-[methyl malonoyl]3-aminopropionate.

1-benzyl-2,4-dioxopiperidine

A mixture of 23.4 gm (89.7 mMol) methyl 1-benzyl-2,4-dioxo-3-piperidinecarboxylate in 200 mL 10% aqueous oxalic acid was stirred at reflux for 15 hours. The reaction mixture was cooled to room temperature and the solution extracted with 3×200 mL dichloromethane. The organic phases were combined, dried over magnesium sulfate, and concentrated under reduced pressure to provide 4.99 gm (27%) of the desired compound.

1-benzyl-2,4-dioxo-3,3-dimethylpiperidine

A mixture of 1.44 gm (7.1 mMol) 1-benzyl-2,4-dioxopiperidine, 4.0 gm (28.9 mMol) potassium carbonate, and 1.5 mL (24.1 mMol) iodomethane in 14 mL dimethylsulfoxide was stirred for 24 hours. The reaction mixture was diluted with ethyl acetate and water. The phases were separated and the organic phases was washed sequentially with water and saturated aqueous sodium chloride, dried over magnesium sulfate and concentrated under reduced pressure. The residue was subjected to silica gel chromatography, eluting with hexane containing 35% ethyl acetate. Fractions containing product were combined and concentrated under reduced pressure to provide 0.61 gm (37%) of the desired compound.

1-benzyl-3,3-dimethyl-4-hydroxypiperidine

A solution of 0.30 gm (1.3 mMol) 1-benzyl-2,4-dioxo-3,3-dimethylpiperidine in 5 mL tetrahydrofuran was stirred at room temperature as 2 mL (2 mMol) lithium aluminum hydride (2M in tetrahydrofuran) was added dropwise. The reaction mixture was then heated to reflux for 3 hours. The reaction mixture was then allowed to cool to room temperature. After stirring at room temperature for about 16 hours, the reaction mixture was cooled in an ice bath and treated sequentially with 0.5 mL water, 0.5 mL 5N sodium hydroxide, and 0.5 mL water with vigorous stirring. The resulting slurry was diluted with dichloromethane and anhydrous sodium sulfate was added. The slurry was filtered and the filter cake washed with dichloromethane. The combined filtrates were concentrated under reduced pressure and the residue subjected to silica gel chromatography, eluting with dichloromethane containing from 0–10% methanol containing 0.1% ammonium hydroxide. Fractions containing product were combined and concentrated under reduced pressure to provide 0.25 gm (88%) of the desired compound.

Oxidation

A solution of 0.40 mL (5.6 mMol) dimethylsulfoxide in 5 mL dichloromethane was cooled to −78° C. To this solution was added 0.35 mL (2.48 mMol) trifluoroacetic anhydride dropwise and the resulting solution stirred for 30 minutes. A solution of 0.25 gm (1.14 mMol) 1-benzyl-3,3-dimethyl-4-hydroxypiperidine in 2 mL dichloromethane was added dropwise and the reaction mixture was stirred for 1 hour. To the solution was then added 1.0 mL (7.2 mMol) triethylamine and the reaction mixture was warmed to 0° C. After stirring for 2 hours, the reaction mixture was poured into water and extracted with ethyl acetate. The organic extracts were combined, dried over sodium sulfate and concentrated under reduced pressure. The residue was subjected to silica gel chromatography, eluting with hexane containing from 0–20% ethyl acetate. Fractions containing product were combined and concentrated under reduced pressure to provide 0.20 gm (79%) of the title compound.

Preparation XXXV

Alternate Synthesis of 1-benzyl-3,3-dimethyl-4-oxopiperidine

Benzylamine (214 g, 2 mol) is combined with formaldehyde (37% in water, 375 g, 4.5 mol) in ethanol (1 L) with occasional cooling. This biphasic mixture is added over a period of 90 minutes to a refluxing solution of 2-methyl-3-butanone (182 g, 2.11 mol) in anhydrous ethanol (1 L) and hydrochloric acid (209 g of 37% solution, 2.1 mol). The brownish solution is heated at reflux for an additional 18 hours. Then triethylamine (310 mL, 223.8 g, 2.21 mol) and formaldehyde (50 g, 36%, 0.6 mol) are added sequentially and the reaction mixture is heated at reflux for 24 hours. The reaction mixture is then cooled to 5° C. and treated with potassium hydroxide (117.6 g, 2.1 mol, dissolved in 200 mL of water). The reaction mixture is then extracted with heptane (2×500 mL) and methyl tert-butyl ether (2×500 mL). The organic extracts is then combined, dried over anhydrous sodium sulfate, filtered and concentrated under vacuum to provide the title compound, (339.36 g after 18% by volume of the above combined organic extracts was removed prior to concentration). This material was purified by chromatography on silica gel (methylene chloride/ethanol, 100:1) to provide purified title compound.

$^1$H NMR (CDCl$_3$) δ1.14 (s, 6H), 2.41 (s,2H), 2.52 (t, 2H), 2.72 (t, 2H), 3.57 (s, 2H), 7.2–7.4 (m, 5H).

Preparation XXXVI

Alternate Synthesis of 1-benzyl-3,3-dimethyl-4-oxopiperidine

In a 1 liter 3-necked flask equipped with mechanical stirring, addition funnel and a calcium chloride drying tube is added a 37% weight solution of formaldehyde (168.5 mL, 2.25 mole) dissolved in 500 mL of absolute ethanol. The resulting solution is cooled in an ice-water bath to 10° C., and benzylamine (109 mL, 1mole) is added dropwise over a one hour period. In a separate 3 liter 3-necked flask equipped with mechanical stirring, addition funnel and two condensers is added 3-methyl-2-butanone (113 mL, 1.06 mole) dissolved in 500 ml of absolute ethanol and concentrated hydrogen chloride (92 mL, 1.11 mole) The resulting solution is brought to reflux and the formaldehyde/benzylamine solution is added dropwise over a 2 hour period. This solution is refluxed overnight, and then cooled to ambient temperature. Diisopropylethylamine (142.2 g, 1.1 mole) and formaldehyde (22.46 mL, 0.3mole) are added and the resulting solution is heated to reflux for six hours, and then cooled to ambient temperature. The solution is quenched with potassium hydroxide (61.6 g, 1.1 mole) in 200 mL of water, and then extracted with 500 mL ethyl acetate three times. The organics are concentrated under vacuum to give 225 g of red oil. The crude oil is dissolved in 1 liter of methylene chloride. This solution is carefully poured over 1 kg of silica gel on a sintered glass filter. The silica gel is washed with 4 L of methylene chloride. The methylene chloride is concentrated under vacuum to provide 142 g of a yellow oil which crystallizes in the freezer overnight. Yield=65.4%.

Preparation XXXVII cis-1-benzyl-3,5-dimethyl-4-oxopiperidine

A solution of 45 mL (90.4 mMol) lithium diisopropylamide (2.0 M in tetrahydrofuran) was cooled to −5° C. A solution of 18.5 gm (75.4 mMol) 1-benzyl-3-methyl-4-oxopiperidine N,N-dimethylhydrazone (prepared from 1-benzyl-3-methyl-4-oxopiperidine and N,N-dimethylhydrazine) in 100 mL tetrahydrofuran was added dropwise over 40 minutes. The reaction mixture was then cooled to −78° C. and 5.16 mL (83 mMol) iodomethane were added dropwise. The reaction mixture was stirred for about 16 hours, warming gradually to room temperature. The resulting homogeneous yellow solution was diluted with 300 mL dichloromethane and was washed first with 100 mL water and then with saturated aqueous sodium chloride. The organic phase was dried over magnesium sulfate and then concentrated under reduced pressure.

This compound (8.5 gm) was dissolved in 200 mL 2.0 M methanolic hydrogen chloride and the resulting mixture heated at reflux for about 16 hours. The reaction mixture was concentrated under reduced pressure and the residue partitioned between 80 mL 5N sodium hydroxide and 200 mL ethyl acetate. The aqueous phase was extracted 3×400 mL ethyl acetate. The organic phases were combined, dried over magnesium sulfate, and concentrated under reduced pressure. The residue was subjected to silica gel chromatography, eluting with a gradient of hexane containing from 0–20% ethyl acetate. Fractions containing the desired compound were combined and concentrated under reduced pressure to provide 5.2 gm of the title compound.

Ion Spray MS: m/e=218 (M+1)

Preparation XXXVIII 1-tert-butoxycarbonyl-3,3-dimethyl-4-trifluoromethanesulfonyloxy-1,2,3,6-tetrahydropyridine A mixture of 10.14 gm (46.66 mMol) 1-benzyl-3,3-dimethyl-4-oxopiperidine, 1.03 gm 10% palladium on carbon, and 11.09 gm (50.81 mMol) di-tert-butyl dicarbonate in 210 mL methanol was purged 3 times with nitrogen and 3 times with hydrogen. The mixture was placed under 50 psig of hydrogen and was shaken at room temperature for 16 hours. The reaction mixture was filtered through a bed of celite and glass microfiber paper. The filtrate was concentrated under reduced pressure and the residue subjected to silica gel chromatography, eluting with hexanes containing 20% ethyl acetate. Fractions containing the product were combined and concentrated under reduced pressure to provide 9.38 gm (88.5%) of 1-(tert-butoxycarbonyl)-3,3-dimethyl-4-oxopiperidine.

A solution of 13.25 mL (26.5 mMol) lithium diisopropylamide (2M in tetrahydrofuran/heptane) was cooled to −78° C. A solution of 5.24 gm (23.05 mMol) of 1-(tert-butoxycarbonyl)-3,3-dimethyl-4-oxopiperidine in 40 mL tetrahydrofuran was added dropwise over 40 minutes, maintaining the reaction temperature below −71° C. After the addition was complete, the reaction mixture was stirred at −78° C. for 90 minutes, and then a solution of 8.70 gm (24.35 mMol) N-phenyltrifluoromethanesulfonimide in 40 mL tetrahydrofuran was added over 10 minutes. The solution was allowed to warm to 0° C. and was stirred for 90 minutes. The reaction mixture was concentrated under reduced pressure and the residue was subjected to neutral alumina chromatography, eluting with 5:1 hexanes:ethyl acetate. The solvent was removed under reduced pressure and the residue was subjected to silica gel chromatography, eluting with 4:1 hexanes:ethyl acetate. Fractions containing product were combined and concentrated under reduced pressure to provide 1.72 gm (75.2%) of the title compound as a clear, colorless oil.

Alternatively, the lithium diisopropylamide was generated in situ by reacting a solution of 0.86 µL (6.14 mMol) diisopropylamine in 10 mL tetrahydrofuran with 2.2 mL (5.5 mMol) n-butyllithium (2.5 M in hexanes). After cooling this solution to −78° C., a solution of 1.076 gm (4.73 mMol) 1-(tert-butoxycarbonyl)-3,3-dimethyl-4-oxopiperidine in 12 mL tetrahydrofuran was added dropwise, maintaining the reaction temperature below −70° C. After the addition was complete, the reaction mixture was stirred at −78° C. for 1 hour, and then a solution of 1.963 gm (5.00 mMol) 2-[N,N-bis(trifluoromethylsulfonyl)amino]-5-chloropyridine in 8 mL tetrahydrofuran was added over 5 minutes. The solution was allowed to warm to 0° C. and was stirred for 90 minutes. The reaction mixture was concentrated under reduced pressure and the residue was subjected to neutral alumina chromatography, eluting with 5:1 hexanes:ethyl acetate. The solvent was removed under reduced pressure to provide 1.566 gm (92.1%) of the title compound as a slightly yellow oil.

Preparation XXXIX 1-benzyl-3-(tert-butyldimethylsilyloxy)methyl-4-oxopiperidine

A mixture of 20.0 gm (70.4 mMol) 1-benzyl-3-methoxycarbonyl-4-oxopiperidine hydrochloride in 60 mL ethylene glycol was cooled in an ice bath as 24 gm hydrogen chloride were added. The slurry was heated at 70° C. for 2 hours and was then poured into 200 mL ice water. The pH was adjusted to about 8 with 5N sodium hydroxide and the resulting mixture extracted well with diethyl ether. The organic extracts were combined, dried over sodium sulfate, and concentrated under reduced pressure to provide 21 gm 8-benzyl-8-azaspiro[4,5]decane-6-carboxylic acid methyl ester.

A solution of 11.4 gm (39.1 mMol) 8-benzyl-8-azaspiro[4,5]decane-6-carboxylic acid methyl ester in 150 mL tetrahydrofuran was treated dropwise with a solution of 58 mL (58 mMol) lithium aluminum hydride (1.0 M in tetrahydrofuran). The reaction mixture was heated at reflux for 4 hours and was then cooled in an ice bath. The mixture was then diluted with ethyl acetate and treated dropwise with 100 mL 1N hydrochloric acid. The pH of the solution was then adjusted to about 8 with 5N sodium hydroxide and the mixture was extracted well with dichloromethane. The organic phases were combined, dried over magnesium sulfate and concentrated under reduced pressure to provide 6-hydroxymethyl-8-benzyl-8-azaspiro[4,5]decane.

A solution of 3.0 gm (11.4 mMol) 6-hydroxymethyl-8-benzyl-8-azaspiro[4,5]decane in 50 mL dichloromethane was cooled to −78° C. and then treated with 2.2 mL (22.8 mMol) dimethylboron bromide dropwise. After stirring at −78° C. for 4 hours, the reaction mixture was treated with 45 mL 1N sodium hydroxide and was allowed to warm to room temperature. The phases were separated and the aqueous phase was extracted well with dichloromethane. The organic phases were combined, dried over magnesium sulfate, and concentrated under reduced pressure. The residue was subjected to silica gel chromatography, eluting with dichloromethane containing from 0–5% methanol. Fractions containing product were combined and concentrated under reduced pressure to provide 1.1 gm (44%) 1-benzyl-3-hydroxymethyl-4-oxopiperidine.

ISMS: m/e=220 (M+H)

EA: Calculated for: $C_{13}H_{17}NO_2$: C, 71.21; H, 7.81; N, 6.39. Found: C, 70.87; H, 7.70; N, 6.41.

A mixture of 0.85 gm (3.87 mMol) 1-benzyl-3-hydroxymethyl-4-oxopiperidine, 0.026 gm (0.39 mMol) imidazole, and 0.701 gm 4.65 mMol) tert-butyldimethylsilyl chloride in dimethylformamide was stirred at room temperature for 16 hours. The reaction mixture diluted with 300 mL ethyl acetate and was washed sequentially with 3×200 mL deionized water and 100 mL saturated aqueous sodium chloride. The organic phase was dried over magnesium sulfate and concentrated under reduced pressure. The residue was subjected to silica gel chromatograpy, eluting with hexanes containing from 0–25% ethyl acetate. Fractions containing product were combined and concentrated under reduced pressure to provide 0.805 gm (62%) of the title compound.

ISMS: m/e=334 (M+H).

Preparation XL (4,5-difluorobenzofur-7-yl)boronic acid

A mixture of 2.0 gm (8.58mMol) 4,5-difluoro-7-bromobenzofuran and 0.202 gm (8.58 mMol) magnesium in 10 mL tetrahydrofuran was heated at reflux for 50 minutes. The resulting mixture was then cooled to −5° C. and treated dropwise with 1.01 mL (8.93 mMol) trimethylborate over 20 minutes. The reaction mixture was stirred at room temperature for 1.5 hours and was then concentrated under reduced pressure. The residue was partitioned between 50 mL deionized water and 50 mL ethyl acetate. The mixture was treated with 0.3 mL acetic acid to adjust to a neutral pH. The phases were separated and the aqueous phase was extracted well with ethyl acetate. The organic phases were combined, dried over magnesium sulfate, and concentrated under reduced pressure to provide 2.1 gm of the title compound.

Alternatively, a mixture of 0.484 gm (2.08 mMol) 4,5-difluoro-7-bromobenzofuran and 0.065 gm (2.67 mMol) magnesium in 5 mL tetrahydrofuran was heated at reflux. Two drops of 1,2-dibromomethane were added and the mixture heated at reflux for 45 minutes. To this mixture were added 260 μL (2.29 mMol) trimethylborate and heating was continued for an additional 45 minutes. After cooling to room temperature, 2.3 mL 1N hydrochloric acid were added and the mixture stirred for 45 minutes. The mixture was then extracted well with diethyl ether. The combined organic extracts were dried over sodium sulfate and concentrated under reduced pressure. The residue was slurried in 4 mL hexanes, the solvent removed by decantation, and the residual solid dried under reduced pressure to provide 0.402 gm (97.8%) of the title compound.

Preparation XLI 1-(tert-butoxycarbonyl)-2-methyl-4-trifluoromethanesulfonyloxy-1,2,3,6-tetrahydropyridine A solution of 5 mL (49 mMol) 4-methoxypyridine in 200 mL tetrahydrofuran was cooled to −40° C., and then 6.9 mL (55 mMol) phenyl chloroformate were added dropwise. After stirring for 15 minutes, 20 mL (60 mMol) methyl magnesium chloride (3M in tetrahydrofuran) were added dropwise and the reaction mixture was allowed to warm to room temperature. After stirring for 30 minutes, the reaction mixture was cooled to −40° C. and treated with 340 mMol potassium tert-butoxide. The reaction mixture was allowed to warm to room temperature. After stirring for 1 hour, the reaction mixture was cooled to −40° C. and was treated with 200 mL saturated aqueous oxalic acid. The reaction was warmed to 20° C. and allowed to stir for 1 hour. The mixture was extracted 2×200 mL diethyl ether. The combined organic phases were washed sequentially with 4×100 mL 0.5 N sodium hydroxide, 2×100 mL saturated aqueous sodium bicarbonate, 3×100 mL deionized water, and 100 mL saturated aqueous sodium chloride. The remaining organics were dried over magnesium sulfate and concentrated under reduced pressure. The residue was subjected to silica gel chromatography, eluting with hexanes containing 40% ethylacetate. Fractions containing product were combined and concentrated under reduced pressure to provide 4.9 gm (47%) 1-(tert-butoxycarbonyl)-2-methyl-4-oxopiperidine.

EA: Calculated for: $C_{11}H_{17}NO_3$: C, 62.54; H, 8.11; N, 6.63. Found: C, 62.78; H, 8.08; N, 6.76.

A solution of 1.65 gm (7.81 mMol) 1-(tert-butoxycarbonyl)-2-methyl-4-oxopiperidine in 20 mL tetrahydrofuran was cooled to −40° C. and was then treated with 8.59 mL (8.59 mMol) lithium tri(sec-butyl)borohydride (1M in tetrahydrofuran). After stirring for 2 hours, the solution was treated with 3.37 gm (8.59 mMol) 2-[N,N-bis(trifluoromethylsulfonyl)amino]-5-chloropyridine and the solution was allowed to warm to room temperature. After stirring for 1 hour, the reaction was diluted with 250 ml diethyl ether and filtered through celite. The celite pad was rinsed with 250 mL diethyl ether and the combined filtrates concentrated under reduced pressure. The residue was subjected to silica gel chromatography, eluting with hexanes containing from 0–9% ethyl acetate. Fractions containing product were combined and concentrated under reduced pressure to provide 2.02 gm (75%) of the title compound.

ISMS: m/e=346 (M+H)

Preparation XLII 1-(tert-butoxycarbonyl)-2-methyl-4-oxopiperidine

A solution of 160.0 gm (733 mMol) di(tert-butyl) dicarbonate in 300 mL tetrahydrofuran was added dropwise to a solution of 100.0 gm (698 mMol) 1,4-dioxa-8-azaspiro-[[4,5]decane in 800 mL tetrahydrofuran over 1 hour. The reaction mixture was stirred for 30 minutes after the addition was complete and was then concentrated under reduced pressure. The residue was dissolved in 600 mL diethyl ether and was washed sequentially with 2×250 mL deionized water, 2×250 mL 5% aqueous sodium bicarbonate, and 250 mL saturated aqueous sodium chloride. The organic phase was dried over potassium carbonate and concentrated under reduced pressure to provide 173.3 gm 8-(tert-butoxycarbonyl)-1,4-dioxa-8-azaspiro[4,5]decane.

A solution of 76.0 gm (312 mMol) 8-(tert-butoxycarbonyl)-1,4-dioxa-8-azaspiro[4,5]decane in 760 mL diethyl ether was cooled to −78° C. and was treated with freshly distilled 49.5 mL (328 mMol) N,N,N',N'-tetramethylethylenediamine. One equivalent of a sec-butyllithium solution was added dropwise over 1.5 hours, maintaining the temperature of the reaction mixture below −70° C. After stirring for 4 hours at −78° C., 38.9 mL (625 mMol) iodomethane were added over 10 minutes. The reaction mixture was stirred for 10 minutes and was then allowed to warm gradually to room temperature. The reaction mixture was treated with 300 mL deionized water and the phase were separated. The aqueous phase was extracted with 300 mL diethyl ether. The organic phases were combined, washed with 4×250 mL deionized water, dried over potassium carbonate and concentrated under reduced pressure. The residue was subjected to silica gel chromatography, eluting with a gradient of hexanes containing from 7–20% ethyl acetate. Fractions containing product were combined and concentrated under reduced pressure to provide 57.1 gm (71%) 7-methyl-8-(tert-butoxycarbonyl)-1,4-dioxo-8-azaspiro[4,5]decane as a clear oil. This material was cooled to 0–5° C. and 279.2 mL trifluoroacetic acid were added. After stirring for 10 minutes, 5.2 mL deionized water were added and the reaction mixture was heated at reflux for 2.5 hours. The reaction mixture was cooled to room temperature and concentrated under reduced pressure. The residue was dissolved in 60 mL ethyl acetate and 120 mL diethyl ether were added over 30 minutes with stirring. The suspension was held in a freezer for 2 hours, filtered, and the solids washed with 30 mL cold diethyl ether to provide 23.5 gm (71.3%) 2-methyl-4-oxopiperidine as a white solid.

A mixture of 12.4 gm (55 mMol) 2-methyl-4-oxopiperidine, 6.89 gm (82 mMol) sodium bicarbonate, and 13.1 gm (60 mMol) di(tert-butoxy) dicarbonate in 40 mL water and 100 mL chloroform was stirred at room temperature for 16 hours. The mixture was diluted with 25 mL deionized water and the phases were separated. The aqueous phase was extracted with 4×25 mL chloroform. The organic phases were combined, dried over sodium sulfate, and concentrated under reduced pressure. The residue was subjected to silica gel chromatography, eluting with 3:1 hexane:ethyl acetate containing 1% triethylamine. Fractions containing product were combined and concentrated under reduced pressure to provide 12.0 gm of the title compound as a slightly yellow oil.

Preparation XLIII 1-(tert-butoxycarbonyl)-2-ethyl-4-oxopiperidine

Beginning with 1,4-dioxa-8-azaspiro-[4,5]decane and iodoethane, the title compound was prepared essentially as described in Preparation XLII.

ISMS: m/e=228 (M+1)

Preparation XLIV 7-bromo-4-chlorobenzofuran

A solution of 5.03 gm (39.1 mMol) 3-chlorophenol in 20 mL dichloromethane was cooled in an ice bath as 6.25 gm (39.1 mMol) bromine were added dropwise. The reaction mixture was allowed to warm to room temperature and was stirred for 16 hours. The reaction mixture was diluted with water, the phases separated, and the organic phase dried over magnesium sulfate. The residue was subjected to silica gel chromatography, eluting with 3:2 dichloromethane:hexanes. Fractions containing product were combined and concentrated under reduced pressure to provide 2.04 gm (25%) of 2-bromo-5-chlorophenol.

HRMS: Calculated for $C_4H_4OClBr$: 205.9134. Found: 205.9125.

EA: Calculated for $C_4H_4OClBr$: C, 34.74; H, 1.94. Found: C, 34.74; H, 1.76.

Beginning with 1.86 gm (8.97 mMol) 2-bromo-5-chlorophenol, 1.07 gm (53%) of the title compound were recovered as a white solid essentially as described in Preparation II.

HRMS: Calculated for $C_6H_4OClBr$: 229.9134. Found: 229.9128.

EA: Calculated for $C_6H_4OClBr$: C, 41.51; H, 1.74. Found: C, 41.13; H, 1.67.

Preparation XLV (4-trifluoromethylbenzofur-7-yl)boronic acid

Beginning with 0.9474 gm (3.575 mMol) 4-trifluoromethyl-7-bromobenzofuran, 0.4349 gm (53%) of the title compound was prepared essentially as described in Preparation XL.

HRMS: Calculated for $C_9H_6BO_3F_3$: 229.0398. Found: 229.0383.

Preparation XLVI 4,6-difluoro-7-bromobenzofuran

A solution of 2.6 gm (20 mMol) 3,5-difluorophenol in 20 mL carbon disulfide was cooled to 0° C. and then a solution of 1.02 mL (20 mMol) bromine in 10 mL carbon disulfide was added dropwise over 30 minutes. After stirring for an additional 30 minutes, the reaction mixture was warmed to room temperature and stirred for 1.5 hours. The reaction mixture was diluted with 200 mL diethyl ether and was washed sequentially with aqueous sodium metabisulfite and saturated aqueous sodium chloride. The organic phase was then dried over sodium sulfate and concentrated under reduced pressure. The residue was vacuum distilled to provide 2.5 gm (60%) of 2-bromo-3,5-difluorophenol (b.p.= 65° C. (5 mm Hg)).

Beginning with 2-bromo-3,5-difluorophenol, the title compound was prepared essentially as described in Preparation XXII.

HRMS: Calculated for $C_8H_3OBrF_2$: 231.9335. Found: 231.9342.

Preparation XLVII 1-(tert-butoxycarbonyl)-2-methyl-1,2,5,6-tetrahydropyridin-4-one A solution of 4.0 gm (20.28 mMol) 1-(tert-butoxycarbonyl)-1,2,3,4-tetrahydropyridin-4-one and 4.21 gm (20.48 mMol) copper(I) bromide-dimethylsulfide complex in 160 mL tetrahydrofuran was cooled to −780C. To this solution was added 7.43 mL (22.31 mMol) methyl magnesium chloride (3.0 M in tetrahydro-furan). After stirring for 1 hour at −78° C. an additional equivalent of methyl magnesium chloride was added and stirring continued for an additional 30 minutes. The reaction mixture was then treated with 10 mL hexamethylphosphoramide followed by the addition of a solution of 15.93 gm (40.56 mMol) 2-[N,N-bis(trifluoromethylsulfonyl)amino]-5-chloropyridine in 50 mL tetrahydrofuran. The reaction mixture was allowed to warm to room temperature and was stirred at room temperature overnight. The reaction mixture was then diluted with 1.5 L diethyl ether and was washed sequentially with 2×500 mL saturated aqueous oxalic acid, 500 mL water, 2×500 mL saturated aqueous sodium bicarbonate, and 500 mL saturated aqueous sodium chloride. The remaining organics were dried over magnesium sulfate and concentrated under reduced pressure. The residue was suspended in hexanes and then filtered. The filtrate was concentrated under reduced pressure and the residue subjected to silica gel chromatography, eluting with a gradient of hexane containing 0–50% ethyl acetate. Fractions containing product were combined and concentrated under reduced pressure to provide 1.92 gm of the title compound as an oil that gradually formed a crystalline mass.

Preparation XLVIII 1-(tert-butoxycarbonyl)-1,2,3,4-tetrahydropyridin-4-one

A solution of 1.0 gm (9.16 mMol) 4-methoxypyridine in 15 mL tetrahydrofuran was cooled to −41° C. To this solution was added dropwise 12.6 mL (18.32 mMol) potassium tri(isopropoxy)borohydride (1.45 M in tetrahydrofuran). The resulting mixture was stirred for 15 minutes and then 1.58 gm (10.07 mMol) phenyl chloroformate were added and the resulting mixture stirred −41° C. After 2 hours, 7.19 gm (7.0 mMol) potassium tert-butoxide were added. After stirring at −41° C. for 30 minutes, the reaction mixture was allowed to warm to room temperature. After 2 hours at room temperature, the reaction mixture was cooled again to −41° C. and was then treated with saturated aqueous oxalic acid. The resulting mixture was extracted well with diethyl ether. The organic extracts were combined and washed sequentially with saturated aqueous oxalic acid, water, saturated aqueous sodium bicarbonate, and saturated aqueous sodium chloride. The remaining organic phase was dried over magnesium sulfate and concentrated under reduced pressure. The residual oil was subjected to silica gel chromatography, eluting with a gradient of hexane containing from 10–40% ethyl acetate. Fractions containing product were combined and concentrated under reduced pressure to provide 1.07 gm of the title compound as a white solid.

MS(ES$^+$): m/e=198.2.

EXAMPLE 1

2-methyl-4-(5-fluorobenzofur-7-yl)-1,2,3,6-tetrahydropyridine fumarate and 2-methyl-4-(5-fluorobenzofur-7-yl)-1,2,5,6-tetrahydropyridine fumarate 1-tert-butoxycarbonyl-2-methyl-4-hydroxy-4-(5-fluorobenzofur-7-yl)piperidine A mixture of 0.55 gm (2.55 mMol) 5-fluoro-7-bromobenzofuran and 0.12 gm (5.14 mMol) magnesium in 5 mL diethyl ether was heated to 40° C. To this mixture were. added 0.23 mL (2.67 mMol) 1,2-dibromoethane dropwise and the mixture was stirred for 45 minutes. The mixture was cooled to room temperature and then a solution of 0.50 gm (2.35 mMol) 1-tert-butoxycarbonyl-2-methyl-4-oxopiperidine in 10 mL diethyl ether was added dropwise. The reaction mixture was stirred for 15 hours at room temperature and was then partitioned between 100 mL ethyl acetate and 20 mL 0.1N hydrochloric acid. The phases were separated and the organic phase was washed sequentially with saturated aqueous sodium bicarbonate and saturated aqueous sodium chloride, dried over magnesium sulfate, and concentrated under reduced pressure to provide 0.68 gm of a residue. This residue was dissolved in 50 mL 1:1 dichloromethane:methanol and the resulting solution cooled to 0° C. To this solution were added 0.68 gm sodium borohydride and the reaction mixture was allowed to warm gradually to room temperature. After 5 hours the reaction mixture was concentrated under reduced pressure. The residue was partitioned between water and dichloromethane. The phases were separated and the organic phase was dried over magnesium sulfate and concentrated under reduced pressure. The residue was subjected to silica gel chromatography, eluting with a gradient of hexane containing from 0–50% ethyl acetate. Fractions containing product were combined and concentrated under reduced pressure to provide 0.50 gm (62%) of the desired compound.

MS: m/e=350(M+1)

Dehydration/Salt Formation

A mixture of 0.35 gm (1 mMol) 1-tert-butoxycarbonyl-2-methyl-4-hydroxy-4-(5-fluorobenzofur-7-yl)piperidine and 0.70 gm p-toluenesulfonic acid hydrate in 15 mL toluene was heated at reflux for 3 hours. The reaction mixture was concentrated under reduced pressure and the residue subjected to ion exchange chromatography (Varian SCX, 10 gm) eluting first with methanol and then with 1N ammonia in methanol. Fractions containing product were combined and concentrated under reduced pressure to provide 0.17 gm (75%) of a mixture of 2-methyl-4-(5-fluorobenzofur-7-yl)-1,2,3,6-tetrahydropyridine and 2-methyl-4-(5-fluorobenzofur-7-yl)-1,2,5,6-tetrahydropyridine. This mixture was dissolved in 5 mL ethanol and the solution was heated to reflux. To this solution were added 0.087 gm (0.075 mMol) fumaric acid. After mixing for about 5 minutes, the reaction mixture was diluted with diethyl ether. The resulting suspension was filtered and the filter cake dried at 60° C. under vacuum for about 16 hours to provide 0.21 gm (83%) of the title compound.

EA: Calculated for $C_{14}H_{14}NOF-C_4H_4O_4$: C, 62.24; H, 5.22; N, 4.03. Found: C, 62.09; H, 5.22; N, 4.00.

EXAMPLE 2

2-methyl-4-(5-fluorobenzofur-7-yl)piperidine fumarate

A mixture of 0.045 gm (0.13 mMol) 2-methyl-4-(5-fluorobenzofur-7-yl)-1,2,3,6-tetrahydropyridine fumarate and 2-methyl-4-(5-fluorobenzofur-7-yl)-1,2,5,6-tetrahydropyridine fumarate and 0.010 gm 10% palladium on carbon in 5 mL ethanol was hydrogenated at 1 atmosphere at room temperature for 5 hours. The reaction mixture was filtered through a pad of celite. The pad was rinsed with ethanol and the filtrate was concentrated under reduced pressure. The residue was subjected to ion exchange chromatography on an SCX column, eluting with methanol followed by 0.5N ammonia in methanol. Fractions containing product were combined and concentrated under reduced pressure to provide 0.024 gm (79%) 2-methyl-4-(5-fluorobenzofur-7-yl)piperidine. This was dissolved in 5 mL ethanol and the solution was heated to reflux. To this solution were added 0.007 gm (0.06 mMol) fumaric acid. After mixing for about 5 minutes, the reaction mixture was diluted with diethyl ether. The mixture was concentrated under reduced pressure and the residue dried at 60° C. under vacuum for about 15 hours to provide 0.013 gm of the title compound.

MS: m/e=234(M+1)

High Resolution MS: Calculated for: 234.1294. Found: 234.1295.

EXAMPLE 3

3-methyl-4-(5-fluorobenzofur-7-yl)-1,2,3,6-tetrahydropyridine and 3-methyl-4-(5-fluorobenzofur-7-yl)-1,2,5,6-tetrahydropyridine 1-benzyl-3-methyl-4-hydroxy-4-(5-fluorobenzofur-7-yl)piperidine A mixture of 6.0 gm (27.9 mMol) 7-bromo-5-fluorobenzofuran and 0.70 gm (28.8 mMol) magnesium in 75 mL diethyl ether was heated at reflux for 30 minutes. To this mixture was then added a solution of 6.3 gm (31 mMol) 1-benzyl-3-methyl-4-oxopiperidine in 30 mL tetrahydrofuran dropwise over 15 minutes. The resulting mixture was heated at reflux for about 24 hours. The reaction mixture was cooled to room temperature and poured into 100 mL water. The resulting emulsion was diluted with 500 mL dichloromethane and then filtered through a bed of celite. The filter cake was washed with 2×200 mL dichloromethane. The filtrate aqueous phase was washed with 2×200 mL dichloromethane. All organic phases were combined, dried over magnesium sulfate, and concentrated under reduced pressure The residue was subjected to silica gel chromatography, eluting with a gradient of hexane containing from 0–50% ethyl acetate. Fractions containing product were combined and concentrated under reduced pressure to provide 7.3 gm (77%) of the desired compound.

1-benzyl-3-methyl-4-(5-fluorobenzofur-7-yl)-1,2,3,6-tetrahydropyridine and 1-benzyl-3-methyl-4-(5-fluorobenzofur-7-yl)-1,2,5,6-tetrahydropyridine A mixture of 5.78 gm (17 mMol) 1-benzyl-3-methyl-4-hydroxy-4-(5-fluorobenzofur-7-yl)piperidine and 10 gm (52.6 mMol) p-toluenesulfonic acid monohydrate in 100 mL toluene was heated at reflux for 24 hours. The reaction mixture was cooled to room temperature and was diluted with 200 mL ethyl acetate followed by 100 mL saturated aqueous sodium bicarbonate and 100 mL IN ammonium hydroxide. The phases were separated and the aqueous phase extracted with 2×100 mL ethyl acetate. The combined organic phases were washed with 100 mL saturated aqueous sodium chloride, dried over magnesium sulfate, and concentrated under reduced pressure. The residue was subjected to silica gel chromatography, eluting with a gradient of hexane containing from 0–50% ethyl acetate. Recovered starting material (4.38 gm) was subjected again to the dehydration conditions in 200 mL toluene. Fractions containing product from both dehydration runs were combined and concentrated under reduced pressure to provide 4.3 gm (79%) 1-benzyl-3-methyl-4-(5-fluorobenzofur-7-yl)-1,2,3,6-tetrahydropyridine and 0.45 gm (8%) 1-benzyl-3-methyl-4-(5-fluorobenzofur-7-yl)-1,2,5,6-tetrahydropyridine.

MS: m/e=322(M+1)

3-methyl-4-(5-fluorobenzofur-7-yl)-1,2,3,6-tetrahydropyridine fumarate

Beginning with 0.50 gm (1.56 mMol) 1-benzyl-3-methyl-4-(5-fluorobenzofur-7-yl)-1,2,3,6-tetrahydropyridine, the title compound was prepared-essentially as described for the following isomer.

MS: m/e=232(M+1)

3-methyl-4-(5-fluorobenzofur-7-yl)-1,2,5,6-tetrahydropyridine fumarate

A solution of 0.45 gm (1.42 mMol) 1-benzyl-3-methyl-4-(5-fluorobenzofur-7-yl)-1,2,5,6-tetrahydropyridine in 15 mL 1,2-dichloroethane was cooled to 0° C. To this solution was then added 0.40 mL (3.7 mMol) 1-chloroethyl chloroformate dropwise. The reaction was heated to reflux for 4 hours and was then concentrated under reduced pressure. The residue was dissolved in methanol and then placed on an SCX column, eluting with methanol followed by 0.5 N ammonia in methanol. Fractions containing the desired free base were combined and concentrated under reduced pressure. This residue was subjected to silica gel chromatography, eluting with a gradient of dichloromethane containing 0–6% methanol, and then with 9:1:0.1 dichloromethane:methanol:ammonium hydroxide. Fractions containing product were combined and concentrated under reduced pressure to provide 0.26 gm (81%) of 3-methyl-4-(5-fluorobenzofur-7-yl)-1,2,5,6-tetrahydropyridine. A solution of 0.21 gm (0.92 mMol) of this free amine in ethanol was heated at reflux and then 0.11 gm (0.92 mMol) fumaric acid were added. The mixture was stirred at reflux for about 5 minutes and was then concentrated under reduced pressure. The residue was treated with 10 mL diethyl ether and the resulting slurry stirred for 30 minutes at room temperature. The mixture was filtered and the solid dried under vacuum for at 60° C. for 15 hours to provide 0.28 gm (88%) of the title compound.

EA: Calculated for $C_{14}H_{14}NOF-C_4H_4O_4$: C, 62.24; H, 5.22; N, 4.03. Found: C, 61.90; H, 5.19; N, 3.90.

EXAMPLE 4 cis-3-methyl-4-(5-fluorobenzofur-7-yl)piperidine hydrochloride

A slurry of 0.80 gm 10% palladium on carbon in 100 mL ethanol was stirred under a hydrogen atmosphere. A solution of 4.23 gm (13.2 mMol) 1-benzyl-3-methyl-4-(5-fluorobenzofur-7-yl)-1,2,3,6-tetrahydropyridine in 100 mL ethanol was added and the mixture stirred under the hydrogen atmosphere for about 16 hours. The reaction mixture was filtered through a celite pad and the filter cake was washed with ethanol. The combined filtrates were concentrated under reduced pressure. The resulting residue was subjected to silica gel chromatography, eluting with a gradient of dichloromethane containing from 0–6% methanol, and then with 9:1:0.1 dichloromethane:methanol:ammonium hydroxide. Fractions containing product were combined and concentrated under reduced pressure to provide 1.0 gm (33%) cis-3-methyl-4-(5-fluorobenzofur-7-yl)piperidine and 1.75 gm (40%) 1-benzyl-3-methyl-4-(5-benzofur-7-yl)piperidine.

A solution of 0.48 gm (2.1 mMol) cis-3-methyl-4-(5-fluorobenzofur-7-yl)piperidine in 5 mL ethyl acetate was treated with 5.0 mL 1N hydrogen chloride in diethyl ether. The resulting slurry was stirred for 1.5 hours at 0° C. and was then filtered under reduced pressure. The solid was washed with diethyl ether and dried under reduced pressure to provide 0.50 gm (89%) of the title compound.

EA: Calculated for $C_{14}H_{16}NOF$—HCl: C, 62.34; H, 6.35; N, 5.19. Found: C, 62.60; H, 6.30; N, 5.29.

EXAMPLE 5

3,3-dimethyl-4-(5-fluorobenzofur-7-yl)piperidine fumarate

1-benzyl-3,3-dimethyl-4-hydroxy-4-(5-fluorobenzofur-7-yl)piperidine

Beginning with 0.28 gm (1.32 mMol) 5-fluoro-7-bromobenzofuran and 0.19 gm (0.088 mMol) 1-benzyl-3,3-dimethyl-4-oxo-piperidine, 0.17 gm (53%) of the desired compound were prepared essentially as described in EXAMPLE 3.

Dehydration

Beginning with 0.17 gm (0.47 mMol) 1-benzyl-3,3-dimethyl-4-hydroxy-4-(5-fluorobenzofur-7-yl)piperidine and 0.36 gm p-toluenesulfonic acid monohydrate, 0.11 gm (70%) of 1-benzyl-3,3-dimethyl-4-(5-fluorobenzofur-7-yl)-1,2,3,6-tetrahydropyridine were prepared essentially as described in EXAMPLE 3.

Deprotection

Beginning with 0.10 gm (0.30 mMol) 1-benzyl-3,3-methyl-4-(5-fluorobenzofur-7-yl)-1,2,3,6-tetrahydropyridine and 0.20 mL (1.8 mMol) 1-chloroethyl chloroformate, 0.053 gm (72%) 3,3-dimethyl-4-(5-fluorobenzofur-7-yl)-1,2,3,6-tetrahydropyridine were prepared essentially as described in EXAMPLE 3.

Salt Formation

Beginning with 0.053.gm (0.22 mMol) 3,3-dimethyl-4-(5-fluorobenzofur-7-yl)-1,2,3,6-tetrahydropyridine and 0.025 gm fumaric acid, 0.070 gm (91%) title compound were prepared essentially as described in EXAMPLE 3.

High Resolution MS: Calculated for $C_{15}H_{16}NOF$. Theory: 246.1294. Found: 246.1312.

EXAMPLE 6

3-methyl-4-(6-fluorobenzofur-7-yl)-1,2,3,6-tetrahydropyridine hydrochloride

1-benzyl-3-methyl-4-hydroxy-4-(6-fluorobenzofur-7-yl)piperidine

Beginning with 5.22 gm (24.3 mMol) 6-fluoro-7-bromobenzofuran and 5.19 gm (25.5 mMol) 1-benzyl-3-methyl-4-oxopiperidine, 4.89 gm (59%) of the desired compound were prepared as a mixture of cis- and trans-isomers, essentially as described in EXAMPLE 3.

Dehydration

Beginning with 4.89 gm (14.4 mMol) 1-benzyl-3-methyl-4-hydroxy-4-(6-fluorobenzofur-7-yl)piperidine and 11 gm p-toluenesulfonic acid monohydrate, 1.84 gm (40%) of 1-benzyl-3-methyl-4-(5-fluorobenzofur-7-yl)-1,2,3,6-tetrahydropyridine were prepared essentially as described in EXAMPLE 3.

Deprotection

Beginning with 1.8 gm (5.6 mMol) 1-benzyl-3-methyl-4-(6-fluorobenzofur-7-yl)-1,2,3,6-tetrahydropyridine and 1.48 mL (14 mMol) 1-chloroethyl chloroformate, 0.343 gm 3-methyl-4-(6-fluorobenzofur-7-yl)-1,2,3,6-tetrahydropyridine were prepared essentially as described in EXAMPLE 3.

Salt Formation

Beginning with about 0.12 gm 3-methyl-4-(6-fluorobenzofur-7-yl)-1,2,3,6-tetrahydropyridine, the title compound was prepared essentially as described in EXAMPLE 4.

EXAMPLE 7

Cis-3-methyl-4-(6-fluorobenzofur-7-yl)piperidine hydrochloride

Beginning with 0.78 gm (2.43 mMol) 1-benzyl-3-methyl-4-(6-fluorobenzofur-7-yl)-1,2,3,6-tetrahydropyridine, the title compound was prepared essentially as described in EXAMPLE 4.

EA: Calculated for $C_{14}H_{16}NOF$—HCl: C, 62.34; H, 6.35; N, 5.19. Found: C, 62.02; H, 6.23; N, 5.17.

EXAMPLE 8

3-methyl-4-(5-chlorobenzofur-7-yl)-1,2,3,6-tetrahydropyridine and 3-methyl-4-(5-chlorobenzofur-7-yl)-1,2,5,6-tetrahydropyridine

1-benzyl-3-methyl-4-hydroxy-4-(5-chlorobenzofur-7-yl)piperidine

Beginning with 4.0 gm (17.3 mMol) 5-chloro-7-bromobenzofuran and 3.86 gm (19.0 mMol) 1-benzyl-3-methyl-4-oxo-piperidine, 5.6 gm (92%) of the desired compound were recovered essentially as described in EXAMPLE 3.

1-benzyl-3-methyl-4-(5-chlorobenzofur-7-yl)-1,2,3,6-tetrahydropyridine and 1-benzyl-3-methyl-4-(5-chlorobenzofur-7-yl)-1,2,5,6-tetrahydropyridine Beginning with 2.19 gm (6.2 mMol) 1-benzyl-3-methyl-4-hydroxy-4-(5-chlorobenzofur-7-yl)piperidine and 4.7 gm p-toluenesulfonic acid monohydrate, 0.79 gm (38%) 1-benzyl-3-methyl-4-(5-chlorobenzofur-7-yl)-1,2,3,6-tetrahydropyridine and 0.18 gm (9%) 1-benzyl-3-methyl-4-(5-chlorobenzofur-7-yl)-1,2,5,6-tetrahydropyridine were prepared essentially as described in EXAMPLE 3.

3-methyl-4-(5-chlorobenzofur-7-yl)-1,2,3,6-tetrahydropyridine fumarate

Beginning with 0.38 gm (1.13 mMol) 1-benzyl-3-methyl-4-(5-chlorobenzofur-7-yl)-1,2,3,6-tetrahydropyridine, the title compound was prepared essentially as described for the corresponding isomer in EXAMPLE 3.

MS: m/e=249(M+1)

3-methyl-4-(5-chlorobenzofur-7-yl)-1,2,5,6-tetrahydropyridine hydrochloride Beginning with 0.074 gm (0.22 mMol) 1-benzyl-3-methyl-4-(5-chlorobenzofur-7-yl)-1,2,5,6-tetrahydropyridine, the title compound was prepared essentially as described for the corresponding isomer in EXAMPLE 3.

High Resolution MS: Calculated for $C_{14}H_{14}NOF$: 248.0842. Found: 248.0826.

EXAMPLE 9

3-methyl-4-(5-methoxybenzofur-7-yl)-1,2,3,6-tetrahydropyridine hydrochloride

1-benzyl-3-methyl-4-hydroxy-4-(5-methoxybenzofur-7-yl)piperidine

Beginning with 4.0 gm (17.6 mMol) 5-methoxy-7-bromobenzofuran and 3.94 gm (19.4 mMol) 1-benzyl-3-methyl-4-oxo-piperidine, 3.33 gm (54%) of the desired compound were recovered essentially as described in EXAMPLE 3.

EA: Calculated for $C_{22}H_{25}NO_3$: C, 75.19; H, 7.17; N, 3.99. Found: C, 74.88; H, 7.03; N, 4.17.

1-benzyl-3-methyl-4-(5-methoxybenzofur-7-yl)-1,2,3,6-tetrahydropyridine

Beginning with 3.13 gm (8.9 mMol) 1-benzyl-3-methyl-4-hydroxy-4-(5-methoxybenzofur-7-yl)piperidine and 6.8 gm p-toluenesulfonic acid monohydrate, 1-benzyl-3-methyl-4-(5-methoxybenzofur-7-yl)-1,2,3,6-tetrahydropyridine was prepared essentially as described in EXAMPLE 3.

High Resolution MS: Calculated for $C_{22}H_{23}NO_2$: 334.1807. Found: 334.1799.

3-methyl-4-(5-methoxybenzofur-7-yl)-1,2,3,6-tetrahydropyridine

Beginning with 1.22 gm (3.66 mMol) 1-benzyl-3-methyl-4-(5-methoxybenzofur-7-yl)-1,2,3,6-tetrahydropyridine, the title compound was prepared essentially as described for the corresponding isomer in EXAMPLE 3.

High Resolution MS: Calculated for $C_{15}H_{17}NO_2$: 244.1338. Found: 244.1324.

EXAMPLE 10

Cis- and trans-3-methyl-4-(5-methoxybenzofur-7-yl)piperidine

Beginning with 0.30 gm (1.23 mMol) 3-methyl-4-(5-methoxybenzofur-7-yl)-1,2,3,6-tetrahydropyridine, 0.27 gm of a mixture of cis- and trans-3-methyl-4-(5-methoxybenzofur-7-yl)piperidine were prepared essentially as described in EXAMPLE 4.

A solution of this mixture of isomers in 50 ml dichloromethane was treated with 0.26 gm (1.21 mMol) di-tert-butyldicarbonate and 0.29 gm (2.20 mMol) diisopropylethylamine. After stirring at room temperature for about 16 hours, the reaction mixture was concentrated under reduced pressure. The residue was subjected to silica gel chromatography, eluting with hexane containing 5% ethyl acetate.

Fractions containing the first eluting isomer were concentrated under reduced pressure to provide 0.034 gm trans-1-(tert-butoxycarbonyl)-3-methyl-4-(5-methoxybenzofur-7-yl)piperidine. Fractions containing the later eluting isomer were concentrated under reduced pressure to provide 0.30 gm cis-1-(tert-butoxycarbonyl)-3-methyl-4-(5-methoxybenzofur-7-yl)piperidine.

cis-3-methyl-4-(5-methoxybenzofur-7-yl)piperidine hydrochloride

A mixture of 0.30 gm cis-1-(tert-butoxycarbonyl)-3-methyl-4-(5-methoxybenzofur-7-yl)piperidine in 10 mL 4N hydrochloric acid in dioxane is stirred at room temperature for 1 hour. The reaction mixture is concentrated under reduced pressure and the white solid residue is dried under reduced pressure at 60° C. for about 16 hours to provide 0.16 gm (96%) of the title compound.

trans-3-methyl-4-(5-methoxybenzofur-1-yl)piperidine hydrochloride

Beginning with 0.045 gm trans-1-(tert-butoxycarbonyl)-3-methyl-4-(5-methoxybenzofur-7-yl)piperidine, 0.034 gm (93%) of the title compound was prepared essentially as described for the cis-isomer.

High Resolution MS: Calculated for: 248.1450. Found: 248.1443.

EXAMPLE 11

3-methyl-4-(4-trifluoromethylbenzofur-7-yl)-1,2,3,6-tetrahydropyridine fumarate 1-benzyl-3-methyl-4-hydroxy-4-(4-trifluoromethylbenzofur-7-yl)piperidine Beginning with 1.5 gm (5.7 mMol) 4-trifluoromethyl-7-bromobenzofuran and 1.26 gm (6.2 mMol) 1-benzyl-3-methyl-4-oxopiperidine, 0.85 gm (39%) of the desired compound were recovered essentially as described in EXAMPLE 3.

MS(FD): m/e=390(M+1)

1-benzyl-3-methyl-4-(4-trifluoromethylbenzofur-7-yl)-1,2,3,6-tetrahydropyridine

Beginning with 0.84 gm (2.2 mMol) 1-benzyl-3-methyl-4-hydroxy-4-(4-trifluoromethylbenzofur-7-yl)piperidine and 1.6 gm p-toluenesulfonic acid monohydrate, 0.18 gm of the desired compound were prepared essentially as described in EXAMPLE 3.

MS(FD): m/e=390(M+1)

3-methyl-4-(4-trifluoromethylbenzofur-7-yl)-1,2,3,6-tetrahydropyridine fumarate

Beginning with 0.15 gm (0.41 mMol) 1-benzyl-3-methyl-4-(4-trifluoromethylbenzofur-7-yl)-1,2,3,6-tetrahydropyridine, the title compound was prepared essentially as described for the corresponding isomer in EXAMPLE 3.

MS(FD): m/e=282(M+1)

EXAMPLE 12

Cis-3-methyl-4-(5-trifluoromethylbenzofur-7-yl)piperidine hydrochloride 1-tert-butoxycarbonyl-3-methyl-4-hydroxy-4-(5-trifluoromethylbenzofur-7-yl)piperidine Beginning with 4.36 gm (16.5 mMol) 5-trifluoromethyl-7-bromobenzofuran and 3.50 gm (16.4 mMol) 1-tert-butoxycarbonyl-2-methyl-4-oxopiperidine, 3.00 gm of the desired compound were recovered as a waxy solid essentially as described in EXAMPLE 1.

m.p.=133–136° C.

MS: m/e=400(M+1)

EA: Calculated for $C_{20}H_{24}NO_4F_3$: C, 60.14; H, 6.06; N, 3.51. Found: C, 60.11; H, 6.11; N, 3.51.

Dehydration

Beginning with 0.75 gm (1.9 mMol) 1-tert-butoxycarbonyl-2-methyl-4-hydroxy-4-(5-trifluoromethylbenzofur-7-yl)piperidine and 1.40 gm p-toluenesulfonic acid monohydrate, 0.47 gm of a mixture of 3-methyl-4-(5-trifluoromethylbenzofur-7-yl)-1,2,3,6-tetrahydropyridine and 3-methyl-4-(5-trifluoromethylbenzofur-7-yl)-1,2,5,6-tetrahydropyridine essentially as described in EXAMPLE 1.

Reduction

Beginning with 0.47 gm (1.67 mMol) of a mixture of 3-methyl-4-(5-trifluoromethylbenzofur-7-yl)-1,2,3,6-tetrahydropyridine and 3-methyl-4-(5-trifluoromethylbenzofur-7-yl)-1,2,5,6-tetrahydropyridine, 0.15 gm of the title compound were recovered essentially as described in EXAMPLE 10.

High Resolution MS: Calculated for: 281.1262. Found: 284.1269.

EA: Calculated for $C_{15}H_{16}NOF_3$—HCl-0.2 $H_2O$: C, 55.72; H, 5.30; N, 4.33. Found: C, 55.78; H, 5.18; N, 4.63.

EXAMPLE 13

3-methyl-4-(5-trifluoromethylbenzofur-7-yl)-1,2,3,6-tetrahydropyridine hydrochloride 1-benzyl-3-methyl-4-hydroxy-4-(5-trifluoromethylbenzofur-7-yl)piperidine Beginning with 1.1 gm (4.15 mMol) 5-trifluoromethyl-7-bromobenzofuran and 0.93 gm (4.57 mMol) 1-benzyl-3-methyl-4-oxopiperidine, 0.70 gm (43%) of the desired compound were recovered as a yellow solid essentially as described in EXAMPLE 3.

1-benzyl-3-methyl-4-(5-trifluoromethylbenzofur-7-yl)-1,2,3,6-tetrahydropyridine

Beginning with 0.67 gm (1.72 mMol) 1-benzyl-3-methyl-4-hydroxy-4-(5-trifluoromethylbenzofur-7-yl)piperidine and 1.3 gm p-toluenesulfonic acid monohydrate, 0.29 gm (46%) of the desired compound were prepared essentially as described in EXAMPLE 3.

MS(FD): m/e=390(M+1)

3-methyl-4-(5-trifluoromethylbenzofur-7-yl)-1,2,3,6-tetrahydropyridine hydrochloride Beginning with 0.16 gm (0.43 mMol) 1-benzyl-3-methyl-4-(5-trifluoromethylbenzofur-7-yl)-1,2,3,6-tetrahydropyridine, the title compound was prepared essentially as described for the corresponding isomer in EXAMPLE 3.

EA: Calculated for $C_{15}H_{14}NOF_3$—HCl: C, 56.70; H, 4.76; N, 4.41. Found: C, 56.59; H, 4.66; N, 4.32.

EXAMPLE 14

3-methyl-4-(4,5-difluorobenzofur-7-yl)-1,2,3,6-tetrahydropyridine hydrochloride 1-benzyl-3-methyl-4-hydroxy-4-(4,5-difluorobenzofur-7-yl)piperidine Beginning with 4.0 gm (17.17 mMol) 4,5-difluoro-7-bromobenzofuran and 3.8 gm (18.88 mMol) 1-benzyl-3-methyl-4-oxopiperidine, 2.6 gm (43%) of the desired compound were recovered as a yellow oil essentially as described in EXAMPLE 3.

EA: Calculated for $C_{21}H_{21}NO_2F_2$: C, 70.57; H, 5.92; N, 3.92. Found: C, 70.41; H, 5.62; N, 3.92.

1-benzyl-3-methyl-4-(4,5-difluorobenzofur-7-yl)-1,2,3,6-tetrahydropyridine

Beginning with 2.30 gm (6.44 mMol) 1-benzyl-3-methyl-4-hydroxy-4-(4,5-difluorobenzofur-7-yl)piperidine and 4.90 gm p-toluenesulfonic acid monohydrate, the desired compound was prepared essentially as described in EXAMPLE 3.

High Resolution MS: Calculated for $C_{21}H_{19}NOF_2$: 340.1513. Found: 340.1503.

EA: Calculated for $C_{21}H_{19}NOF_2$: C, 74.32; H, 5.64; N, 4.13. Found: C, 74.57; H, 5.85; N, 4.05.

3-methyl-4-(4,5-difluorobenzofur-7-yl)-1,2,3,6-tetrahydropyridine hydrochloride

Beginning with 1.12 gm 3.36 mMol) 1-benzyl-3-methyl-4-(4,5-difluorobenzofur-7-yl)-1,2,3,6-tetrahydropyridine, 0.70 gm (83.5%) of 3-methyl-4-(4,5-difluorobenzofur-7-yl)-1,2,3,6-tetrahydropyridine were prepared essentially as described in EXAMPLE 3.

The title compound was prepared from a portion of this material essentially as described for the corresponding isomer in EXAMPLE 3.

EA: Calculated for $C_{14}H_{13}NOF_2$—HCl: C, 58.85; H, 4.94; N, 4.90. Found: C, 58.95; H, 4.91; N, 4.86.

EXAMPLE 15

Cis- and trans-3-methyl-4-(4,5-difluorobenzofur-7-yl)piperidine

Beginning with 1.12 gm (3.36 mMol) 3-methyl-4-(4,5-difluorobenzofur-7-yl)-1,2,3,6-tetrahydropyridine, a mixture of cis- and trans-3-methyl-4-(4,5-difluorobenzofur-7-yl)piperidine was prepared as a brown foam essentially as described in EXAMPLE 4.

A solution of this mixture of isomers was treated with di-tert-butyldicarbonate and the isomers separated essentially as described in EXAMPLE 10. Fractions containing the first eluting isomer were concentrated under reduced pressure to provide 0.15 gm trans-1-(tert-butoxycarbonyl)-3-methyl-4-(4,5-difluorobenzofur-7-yl)piperidine. Fractions containing the later eluting isomer were concentrated under reduced pressure to provide 0.54 gm cis-1-(tert-butoxycarbonyl)-3-methyl-4-(4,5-difluorobenzofur-7-yl)piperidine.

cis-3-methyl-4-(4,5-difluorobenzofur-7-yl)piperidine hydrochloride

The title compound was prepared by treating cis-1-(tert-butoxycarbonyl)-3-methyl-4-(4,5-difluorobenzofur-7-yl)piperidine with 4N hydrochloric acid in dioxane essentially as described in EXAMPLE 10.

High Resolution MS: Calculated for: 252.1200. Found: 252.1181.

trans-3-methyl-4-(4,5-difluorobenzofur-7-yl)piperidine hydrochloride

The title compound was prepared by treating trans-1-(tert-butoxycarbonyl)-3-methyl-4-(4,5-difluorobenzofur-7-yl)piperidine with 4N hydrochloric acid in dioxane essentially as described for the cis-isomer.

High Resolution MS: Calculated for: 252.1200. Found: 252.1188.

EXAMPLE 16 cis-3-methyl-4-(4-trifluoromethylbenzofur-7-yl)piperidine hydrochloride cis-1-benzyl-3-methyl-4-hydroxy-4-(4-trifluoromethylbenzofur-7-yl)piperidine Beginning with 4.36 gm (16.46 mMol) 4-trifluoromethyl-7-bromobenzofuran and 3.30 gm (16.40 mMol) 1-benzyl-3-methyl-4-oxopiperidine, 7.5 gm of cis- and trans-1-benzyl-3-methyl-4-hydroxy-4-(4-trifluoromethylbenzofur-7-yl)piperidine were prepared as an orange oil, essentially as described in EXAMPLE 3. This oil was subjected to silica gel chromatography, eluting with a gradient of dichloromethane containing from 0–5% 2N ammonia in methanol. Fractions containing the desired compound were combined and concentrated under reduced pressure to provide 1.04 gm (16.3%) as a yellow foam.

cis-1-benzyl-3-methyl-4-(methyl oxoacetoxy)-4-(4-trifluoromethylbenzofur-7-yl)piperidine A solution of 1.02 gm (2.62 mMol) cis-1-benzyl-3-methyl-4-hydroxy-4-(4-trifluoromethylbenzofur-7-yl)piperidine and 0.98 gm (8.00 mMol) 4-(dimethylamino)pyridine in 12 mL dichloromethane was cooled in an ice water bath. To this mixture were added 0.71 mL (7.73 mMol) methyl chlorooxoacetate and the resulting mixture was stirred for about 18 hours at room temperature. The reaction mixture was diluted with 15 mL dichloromethane and then poured into 25 mL water. The phases were separated and the organic phase washed with water. The organic phase was then washed with 50 mL saturated aqueous sodium bicarbonate, dried over magnesium sulfate and concentrated under reduced pressure to provide 1.05 gm (84%) of the desired compound as a yellow-orange foam.

Ion Spray MS: m/e=476 (M+1)

cis-1-benzyl-3-methyl-4-(4-trifluoromethylbenzofur-7-yl)piperidine

A solution of 1.04 gm (2.19 mMol) cis-1-benzyl-3-methyl-4-(methyl oxoacetoxy)-4-(4-trifluoromethylbenzofur-7-yl)piperidine, 3.77 mL (14 mMol) tri(n-butyl)tin hydride, and 0.19 gm (1.16 mMol) 2,21-azobisisobutyronitrile in 20 mL of toluene was stirred at reflux for about 18 hours. The reaction mixture was concentrated under reduced pressure and the residue subjected to ion exchange (Varian SCX) chromatography, eluting sequentially with 40 mL 1:1 dichloromethane:methanol, 50 mL methanol, and then 50 mL 2M ammonia in methanol. Fractions containing product were combined and concentrated under reduced pressure to give a yellow oil. This oil was subjected to silica gel chromatography, eluting first with dichloromethane containing 0.5% 2M ammonia in methanol and then with dichloromethane containing 1% 2M ammonia in methanol. Fractions containing product were combined and concentrated under reduced pressure to provide 0.66 gm (81%) of the desired compound as a colorless oil in two fractions.

Deprotection/salt Formation

Beginning with 0.41 gm (4.39 mMol) cis-1-benzyl-3-methyl-4-(4-trifluoromethylbenzofur-7-yl)piperidine, the title compound was recovered as a colorless solid essentially as described in EXAMPLE 3.

High Resolution MS: Calculated for: 284.1262. Found: 284.1272.

EA: Calculated for $C_{15}H_{17}NOF_3$—HCl: C, 56.35; H, 5.36. Found: C, 56.07; H, 5.34.

EXAMPLE 17 cis-3-methyl-4-(5-chlorobenzofur-7-yl)piperidine hydrochloride 1-benzyl-3-methyl-4-hydroxy-4-(5-chlorobenzofur-7-yl)piperidine Beginning with 10.0 gm (46.5 mMol) 5-chloro-7-bromobenzofuran, 12.3 gm (74%) of cis- and trans-1-benzyl-3-methyl-4-hydroxy-4-(5-chlorobenzofur-7-yl)piperidine were prepared essentially as described in EXAMPLE 3.

1-benzyl-3-methyl-4-(methyl oxoacetoxy)-4-(5-chlorobenzofur-7-yl)piperidine

Beginning with 3.0 gm (8.84 mMol) 1-benzyl-3-methyl-4-hydroxy-4-(4-chlorobenzofur-7-yl)piperidine, 3.28 gm (84%) of the desired compound were recovered essentially as described in EXAMPLE 16.

cis-1-benzyl-3-methyl-4-(5-chlorobenzofur-7-yl)piperidine

Beginning with 3.28 gm (7.4 mMol) 1-benzyl-3-methyl-4-(methyl oxoacetoxy)-4-(5-chlorobenzofur-7-yl)piperidine, 1.58 gm (62%) of the desired compound were prepared essentially as described in EXAMPLE 16.

Deprotection/salt Formation

Beginning with 0.11 gm (0.32 mMol) cis-1-benzyl-3-methyl-4-(5-chlorobenzofur-7-yl)piperidine, 0.044 gm (48%) the title compound was recovered as a colorless solid essentially as described in EXAMPLE 3.

EXAMPLE 18 cis-3-methyl-4-(4-chloro-5-fluorobenzofur-7-yl)piperidine hydrochloride

1-benzyl-3-methyl-4-hydroxy-4-(4-chloro-5-fluorobenzofur-7-yl)piperidine

Beginning with 1.2 gm (4.81 mMol) 4-chloro-5-fluoro-7-bromobenzofuran, 0.47 gm (26%) of cis- and trans-1-benzyl-3-methyl-4-hydroxy-4-(4-chloro-5-fluorobenzofur-7-yl)piperidine were prepared essentially as described in EXAMPLE 3.

cis-1-benzyl-3-methyl-4-(4-chloro-5-fluorobenzofur-7-yl)piperidine

Beginning with 0.56 gm (1.49 mMol) 1-benzyl-3-methyl-4-hydroxy-4-(4-chloro-5-fluorobenzofur-7-yl)piperidine, 1-benzyl-3-methyl-4-(methyl oxoacetoxy)-4-(4-chloro-5-fluorobenzofur-7-yl)piperidine was recovered essentially as described in EXAMPLE 16. This material was treated with tri(n-butyl)tin hydride essentially as described in EXAMPLE 16 to provide the desired compound.

Deprotection/salt Formation

Beginning with 0.12 gm (0.34 mMol) cis-1-benzyl-3methyl-4-(4-chloro-5-fluorobenzofur-7-yl)piperidine, the title compound was recovered as a colorless solid essentially as described in EXAMPLE 3.

High Resolution MS: Calculated for: 268.0904. Found: 268.0899.

EA: Calculated for $C_{14}H_{15}NOClF$—HCl-0.35 $H_2O$: C, 54.16; H, 5.42. Found: C, 53.87; H, 5.42.

EXAMPLE 19 cis-3-ethyl-4-(6-fluorobenzofur-7-yl)piperidine hydrochloride cis- and trans-1-benzyl-3-ethyl-4-hydroxy-4-(6-fluorobenzofur-7-yl)piperidine A solution of 3.74 gm (17.4 mMol) 6-fluoro-7-bromobenzofuran in 100 mL tetrahydrofuran was cooled to −78° C. A solution of 20.5 mL (34.8 mMol) tert-butyllithium (1.7 M in pentane) was added dropwise at a rate to maintain the temperature of the reaction mixture below −60° C. Once the addition was complete, the reaction mixture was stirred for 15 minutes and then a solution of 3.78 gm (17.4 mMol) 1-benzyl-3-ethyl-4-oxopiperidine in 50 mL tetrahydrofuran was added dropwise at a rate to maintain the temperature of the reaction mixture below −70° C. The cooling bath was removed and the reaction mixture was stirred for about 18 hours, gradually warming to room temperature. The reaction mixture was then diluted with water and extracted with 2×200 mL ethyl acetate. The organic extracts were combined, dried over magnesium sulfate and concentrated under reduced pressure. The residue was subjected to silica gel chromatography, eluting with hexane containing 25% ethyl acetate. Fractions containing product were combined and concentrated under reduced pressure to provide 5.6 gm (91%) of the desired compound as a light yellow oil.

cis-1-benzyl-3-ethyl-4-(6-fluorobenzofur-7-yl)piperidine

Beginning with 5.4 gm (15.3 mMol) 1-benzyl-3-ethyl-4-hydroxy-4-(6-fluorobenzofur-7-yl)piperidine, 5.91 gm (88%) 1-benzyl-3-ethyl-4-(methyl oxoacetoxy)-4-(6-fluorobenzofur-7-yl)piperidine was recovered as an orange oil, essentially as described in EXAMPLE 16. This material was treated with tri(n-butyl)tin hydride essentially as described in EXAMPLE 16 to provide 4.91 gm of the desired compound.

Deprotection/salt Formation

Beginning with 4.5 gm (13.34 mMol) cis-1-benzyl-3-ethyl-4-(6-fluorobenzofur-7-yl)piperidine, 0.43 gm of the title compound was recovered as an off-white solid essentially as described in EXAMPLE 3.

Ion Spray MS: m/e=248 (M+H)

EXAMPLE 20 cis-3-methyl-4-(6-trifluoromethylbenzofur-7-yl)piperidine hydrochloride cis- and trans-1-benzyl-3-methyl-4-hydroxy-4-(6-trifluoromethylbenzofur-7-yl)piperidine Beginning with 0.53 gm (2.00 mMol) 6-trifluoromethyl-7-bromobenzofuran and 0.41 gm (2.00 mMol) 1-benzyl-3-methyl-4-oxopiperidine, the desired compound was prepared essentially as described in EXAMPLE 19.

cis-1-benzyl-3-methyl-4-(6-trifluoromethylbenzofur-7-yl)piperidine

The reaction mixture containing a mixture of cis- and trans-1-benzyl-3-methyl-4-hydroxy-4-(6-trifluoromethylbenzofur-7-yl)piperidine from the previous reaction was treated with 0.20 mL (2.2 mMol) methyl chlorooxalate essentially as described in EXAMPLE 16 to provide 0.77 gm 1-benzyl-3-methyl-4-(methyl oxoacetoxy)-4-(6-trifluoromethylbenzofur-7-yl)piperidine as an oil.

Ion Spray MS: m/e=476 (M+1)

This material was treated with tri(n-butyl)tin hydride essentially as described in EXAMPLE 16 to provide 0.43 gm of the desired compound.

Ion Spray MS: m/e=374 (M+1)

Deprotection/salt Formation

Beginning with 0.43 gm cis-1-benzyl-3-methyl-4-(6-trifluoromethylbenzofur-7-yl)piperidine, 0.052 gm of the title compound were recovered as described in EXAMPLE 3.

High Resolution MS: Calculated for $C_{15}H_{17}NOF_3$: 284.1262. Found: 284.1266.

EA: Calculated for $C_{15}H_{16}NOF_3$—HCl-1.5 $H_2O$: C, 51.96; H, 5.52; N, 4.04. Found: C, 51.98; H, 5.22; N, 4.17.

EXAMPLE 21 cis-3-methyl-4-(6-chloro-7-fluorobenzofur-7-yl)piperidine hydrochloride cis-1-benzyl-3-methyl-4-hydroxy-4-(6-chloro-7-fluorobenzofur-7-yl)piperidine Beginning with 4.00 gm (16.03 mMol) 6-chloro-7-fluoro-7-bromobenzofuran and 3.26 gm (16.03 mMol) 1-benzyl-3-methyl-4-oxopiperidine, 1.50 gm of the desired compound was prepared as an orange oil essentially as described in EXAMPLE 19.

cis-1-benzyl-3-methyl-4-(5-chloro-6-fluorobenzofur-7-yl)piperidine

Beginning with 1.32 gm (3.53 mMol) cis-1-benzyl-3-methyl-4-hydroxy-4-(5-chloro-6-fluorobenzofur-7-yl)piperidine, 1.55 gm 1-benzyl-3-methyl-4-(methyl oxoacetoxy)-4-(5-chloro-6-fluorobenzofur-7-yl piperidine was prepared essentially as described in EXAMPLE 16.

Ion Spray MS: m/e=460 (M$^+$)

Beginning with 1.07 gm (2.33 mMol) 1-benzyl-3-methyl-4-(methyl oxoacetoxy)-4-(5-chloro-6-fluorobenzofur-7-yl)piperidine, this material was treated with tri(n-butyl)tin hydride essentially as described in EXAMPLE 16 to provide 0.39 gm of the desired compound.

Ion Spray MS: m/e=358 (M$^+$)

Deprotection/salt Formation

Beginning with 0.20 gm cis-1-benzyl-3-methyl-4-(5-chloro-6-fluorobenzofur-7-yl)piperidine, 0.049 gm of the title compound were recovered as an off-white solid essentially as described in EXAMPLE 3.

m.p.=242–245° C. (dec.)

High Resolution MS: Calculated for $C_{14}H_{16}NOClF$: 268.0904. Found: 268.0906.

EA: Calculated for $C_{14}H_{15}NOClF$—HCl-0.1H$_2$O: C, 54.95; H, 5.01; N, 4.57. Found: C, 54.87; H, 5.21; N, 4.78.

EXAMPLE 22 cis-3-methyl-4-(2-methylbenzofur-7-yl)piperidine hydrochloride

1-benzyl-3-methyl-4-hydroxy-4-(2-methylbenzofur-7-yl)piperidine

Beginning with 1.0 gm (4.74 mMol) 2-methyl-7-bromobenzofuran and 1.01 gm (4.98 mMol) 1-benzyl-3-methyl-4-oxopiperidine, 1.06 gm of the desired compound was prepared as an orange oil essentially as described in EXAMPLE 19.

cis-1-benzyl-3-methyl-4-(2-methylbenzofur-7-yl)piperidine

Beginning with 1.06 gm (3.16 mMol) cis-1-benzyl-3-methyl-4-hydroxy-4-(2-methylbenzofur-7-yl)piperidine, 1-benzyl-3-methyl-4-(methyl oxoacetoxy)-4-(2-methylbenzofur-7-yl)piperidine was prepared essentially as described in EXAMPLE 16. This material was treated with tri(n-butyl)tin hydride essentially as described in EXAMPLE 16 to provide the desired compound.

Deprotection/salt Formation

Beginning with 3.16 mMol cis-1-benzyl-3-methyl-4-(2-methylbenzofur-7-yl)piperidine, 0.41 gm of the title compound were recovered as an off-white solid essentially as described in EXAMPLE 3.

Ion Spray MS: m/e=230 (M+H).

EA: Calculated for $C_{15}H_{19}NO$—HCl: C, 67.78; H, 7.58; N, 5.26. Found: C, 67.35; H, 7.61; N, 4.96.

EXAMPLE 23 trans-3-methyl-4-(6-fluorobenzofur-7-yl)piperidine hydrochloride

1-benzyl-3-methyl-4-hydroxy-4-(6-fluorobenzofur-7-yl)piperidine

Beginning with 12.7 gm (59 mMol) 6-fluoro-7-bromobenzofuran and 13.2 gm (65 mMol) 1-benzyl-3-methyl-4-oxopiperidine, 18 gm of the desired compound was prepared as an orange oil essentially as described in EXAMPLE 19.

Ion Spray MS: m/e=340 (M+1)

trans-1-benzyl-3-methyl-4-(2-methylbenzofur-7-yl)piperidine

Beginning with 17.5 gm (51.6 mMol) 1-benzyl-3-methyl-4-hydroxy-4-(6-fluorobenzofur-7-yl)piperidine, 19.3 gm 1-benzyl-3-methyl-4-(methyl oxoacetoxy)-4-(6-fluorobenzofur-7-yl)piperidine were prepared essentially as described in EXAMPLE 16.

Ion Spray MS: m/e=426 (M+1)

Beginning with 38 gm (89 mMol) 1-benzyl-3-methyl-4-(methyl oxoacetoxy)-4-(6-fluorobenzofur-7-yl)piperidine, 1.4 gm of the desired compound were prepared by treatment with tri(n-butyl)tin hydride essentially as described in EXAMPLE 16.

Deprotection/salt Formation

Beginning with 1.4 gm (4.3 mMol) trans-1-benzyl-3-methyl-4-(6-fluorobenzofur-7-yl)piperidine, the title compound was recovered essentially as described in EXAMPLE 3.

Ion Spray MS: m/e=234 (M+1)

EXAMPLE 24 cis-3-methyl-4-(benzofur-4-yl)piperidine hydrochloride

1-benzyl-3-methyl-4-hydroxy-4-(benzofur-4-yl)piperidine

Beginning with 2.0 gm (10.2 mMol) 4-bromobenzofuran and 2.06 gm (10.2 mMol) 1-benzyl-3-methyl-4-oxopiperidine, 2.24 gm (69%) of the desired compound were prepared essentially as described in EXAMPLE 19.

Ion Spray MS: m/e=340 (M+1)

cis-1-benzyl-3-methyl-4-(benzofur-4-yl)piperidine

Beginning with 2.1 gm (6.53 mMol) 1-benzyl-3-methyl-4-hydroxy-4-(benzofur-4-yl)piperidine, 2.23 gm 1-benzyl-3-methyl-4-(methyl oxoacetoxy)-4-(benzofur-4-yl)piperidine were prepared essentially as described in EXAMPLE 16.

Beginning with 2.23 gm (5.47 mMol) 1-benzyl-3-methyl-4-(methyl oxoacetoxy)-4-(benzofur-4-yl)piperidine, 0.67 gm of the desired compound were prepared by treatment with tri(n-butyl)tin hydride essentially as described in EXAMPLE 16.

Deprotection/salt Formation

Beginning with 0.67 gm (2.2 mMol) cis-1-benzyl-3-methyl-4-(benzofur-4-yl)piperidine, 0.32 gm of the title compound were recovered essentially as described in EXAMPLE 3.

High Resolution MS: Calculated for $C_{14}H_{18}NO$: 216.1388. Found: 216.1389.

EXAMPLE 25 cis-3-methyl-4-(4,6-difluorobenzofur-7-yl)piperidine hydrochloride 1-benzyl-3-methyl-4-hydroxy-4-(4,6-difluorobenzofur-7-yl)piperidine Beginning with 1.27 gm (5.45 mMol) 4,6-difluoro-7-bromobenzofuran and 1.16 gm (5.72 mMol) 1-benzyl-3-methyl-4-oxopiperidine, 1.51 gm (78%) of the desired compound were prepared essentially as described in EXAMPLE 19.

cis-1-benzyl-3-methyl-4-(4,6-difluorobenzofur-7-yl)piperidine

Beginning with 1.24 gm (3.48 mMol) 1-benzyl-3-methyl-4-hydroxy-4-(4,6-difluorobenzofur-7-yl)piperidine, 1-benzyl-3-methyl-4-(methyl oxoacetoxy)-4-(4,6-difluorobenzofur-7-yl)piperidine were prepared essentially as described in EXAMPLE 16. This material was treated with tri(n-butyl)tin hydride essentially as described in EXAMPLE 16 to prepare 0.91 gm (77%) of the desired compound.

Deprotection/salt Formation

Beginning with 0.60 gm (1.76 mMol) cis-1-benzyl-3-methyl-4-(4,6-difluorobenzofur-7-yl)piperidine, the title compound was recovered essentially as described in EXAMPLE 3.

High Resolution MS: Calculated for $C_{14}H_{16}NOF_2$: 252.1200. Found: 252.1210.

EXAMPLE 26 cis-3-methyl-4-(5-fluorobenzofur-4-yl)piperidine hydrochloride 1-benzyl-3-methyl-4-hydroxy-4-(5-fluorobenzofur-4-yl)piperidine Beginning with 1.13 gm (5.26 mMol) 4-bromo-5-fluorobenzofuran and 1.18 gm (6.2 mMol) 1-benzyl-3-methyl-4-oxopiperidine, 1.21 gm (68%) of the desired compound were prepared essentially as described in EXAMPLE 19.

cis-1-benzyl-3-methyl-4-(5-fluorobenzofur-4-yl)piperidine

Beginning with 0.50 gm (1.47 mMol) 1-benzyl-3-methyl-4-hydroxy-4-(5-fluorobenzofur-4-yl)piperidine, 1-benzyl-3-methyl-4-(methyl oxoacetoxy)-4-(5-fluorobenzofur-4-yl)piperidine was prepared essentially as described in EXAMPLE 16. This material was treated with tri(n-butyl)tin hydride essentially as described in EXAMPLE 16 to prepare 0.43 gm (80%) of the desired compound.

Deprotection/salt Formation

Beginning with 0.42 gm (1.32 mMol) cis-1-benzyl-3-methyl-4-(5-fluorobenzofur-4-yl)piperidine, the title compound was recovered essentially as described in EXAMPLE 3.

Ion Spray MS: m/e=234 (M+1)

EXAMPLE 27

3,3-dimethyl-4-(4,6-difluorobenzofur-7-yl)piperidine hydrochloride 1-benzyl-3,3-dimethyl-4-hydroxy-4-(4,6-difluorobenzofur-7-yl)piperidine Beginning with 1.17 gm (5.01 mMol) 4,6-difluoro-7-bromobenzofuran and 1.14 gm (5.26 mMol) 1-benzyl-3,3-dimethyl-4-oxopiperidine, 0.97 gm (52%) of the desired compound were prepared essentially as described in EXAMPLE 19.

1-benzyl-3,3-dimethyl-4-(4,6-difluorobenzofur-7-yl)piperidine

Beginning with 0.84 gm (2.26 mMol) 1-benzyl-3,3-dimethyl-4-hydroxy-4-(4,6-difluorobenzofur-7-yl)piperidine, 0.84 gm (81%) 1-benzyl-3,3-dimethyl-4-(methyl oxoacetoxy)-4-(4,6-difluorobenzofur-7-yl)piperidine were prepared essentially as described in EXAMPLE 16. This material (0.57 gm, 1.25 mMol) was treated with tri(n-butyl)tin hydride essentially as described in EXAMPLE 16 to prepare 0.35 gm (79%) of the desired compound.

Deprotection/salt Formation

Beginning with 0.48 gm (1.35 mMol) 1-benzyl-3,3-dimethyl-4-(4,6-difluorobenzofur-7-yl)piperidine, the title compound was recovered essentially as described in EXAMPLE 3.

Ion Spray MS: m/e=266 (M+1)

EXAMPLE 28 cis-3-methyl-4-(5,6-difluorobenzofur-7-yl)piperidine hydrochloride 1-benzyl-3-methyl-4-hydroxy-4-(5,6-difluorobenzofur-7-yl)piperidine Beginning with 0.22 gm (0.94 mMol) 5,6-difluoro-7-bromobenzofuran and 0.21 gm (1.04 mMol) 1-benzyl-3-methyl-4-oxopiperidine, 0.13 gm (38%) of the desired compound were prepared essentially as described in EXAMPLE 19.

cis-1-benzyl-3-methyl-4-(5,6-difluorobenzofur-7-yl)piperidine

Beginning with 0.75 gm (2.08 mMol) 1-benzyl-3-methyl-4-hydroxy-4-(5,6-difluorobenzofur-7-yl)piperidine, 1-benzyl-3-methyl-4-(methyl oxoacetoxy)-4-(5,6-difluorobenzofur-7-yl)piperidine was prepared essentially as described in EXAMPLE 16. This material was treated with tri(n-butyl)tin hydride essentially as described in EXAMPLE 16 to prepare 0.23 gm (32%) of the desired compound.

Ion Spray MS: m/e=342 (M+1)

Deprotection/salt Formation

Beginning with 1-benzyl-3-methyl-4-(5,6-difluorobenzofur-7-yl)piperidine, the title compound was recovered essentially as described in EXAMPLE 3.

Ion Spray MS: m/e=252 (M+H).

EA: Calculated for $C_{14}H_{15}NOF_2$—HCl: C, 58.44; H, 5.60; N, 4.87. Found: C, 58.51; H, 5.35; N, 4.83.

EXAMPLE 29

3-methyl-4-(4,5,6-trifluorobenzofur-7-yl)piperidine hydrochloride 1-benzyl-3-methyl-4-hydroxy-4-(4,5,6-trifluorobenzofur-7-yl piperidine Beginning with 1.02 gm (4.06 mMol) 4,5,6-trifluoro-7-bromobenzofuran and 0.91 gm (4.47 mMol) 1-benzyl-3-methyl-4-oxopiperidine, 1.5 gm (100%) of the desired compound were prepared essentially as described in EXAMPLE 19.

Ion Spray MS: m/e=376 (M+1)

1-benzyl-3-methyl-4-(4,5,6-trifluorobenzofur-7-yl)-1,2,3,6-tetrahydropyridine Beginning with 1.3 gm (3.46 mMol) 1-benzyl-3-methyl-4-hydroxy-4-(4,5,6-trifluorobenzofur-7-yl)piperidine and 6.6 gm p-toluenesulfonic acid monohydrate, the desired compound was prepared essentially as described in EXAMPLE 3.

Ion Spray MS: m/e=358 (M+1)

3-methyl-4-(4,5,6-trifluorobenzofur-7-yl)-1,2,3,6-tetrahydropyridine

Beginning with 0.48 gm (1.35 mMol) 1-benzyl-3-methyl-4-(4,5,6-trifluoroben-zofur-7-yl)-1,2,3,6-tetrahydropyridine, 0.31 gm (89%) of the desired compound were prepared essentially as described in EXAMPLE 3.

Ion Spray MS: m/e=268 (M+1)

Reduction

Beginning with 0.30 gm (1.10 mMol) 3-methyl-4-(4,5,6-trifluorobenzofur-7-yl)-1,2,3,6-tetrahydropyridine, 0.16 gm of the title compound were prepared essentially as described in EXAMPLE 15.

Ion Spray MS: m/e=271 (M+1)

EXAMPLE 30 cis-3-methyl-4-(3,5-dichloro-6-fluorobenzofur-7-yl) piperidine hydrochloride and cis-3-methyl-4-(3-chloro-6-fluorobenzofur-7-yl)piperidine hydrochloride Chlorine was bubbled into a solution of 0.25 gm (0.93 mMol) cis-3-methyl-4-(6-fluorobenzofur-7-yl)piperidine hydrochloride in 75 mL dichloromethane for 1 minute. The reaction vessel was sealed and the mixture was stirred at room temperature for 2 hours and then the reaction mixture was concentrated under reduced pressure.

The resulting residue was dissolved in 50 mL 0.5 N ethanolic potassium hydroxide. The resulting solution was stirred for 2 hours at room temperature and was then acidified by the addition of 5N hydrochloric acid. This solution was run through an ion exchange column (Varian SCX, 10 gm), eluting with methanol. Fractions containing the desired compound were combined and concentrated under reduced pressure.

This residue was dissolved in dichloromethane and was then treated with 0.22 gm di-tert-butyl dicarbonate and 0.48 mL diisopropylethylamine. The resulting solution was stirred for 1 hour a room temperature. The reaction mixture was concentrated under reduced pressure and the residue dissolved in 100 mL ethyl acetate. This solution was washed sequentially with water and saturated aqueous sodium chloride, dried over magnesium sulfate, and concentrated under reduced pressure. The residue was subjected to silica gel chromatography, eluting with a gradient of hexane containing from 0–5% ethyl acetate.

Fractions containing cis-1-(tert-butoxycarbonyl)-3-methyl-4-(3,5-dichloro-6-fluorobenzofur-7-yl)piperidine were combined and concentrated under reduced pressure to provide 0.107 gm. (Ion Spray MS: m/e=403 (M+1)). A solution of this material in 3.5 mL 4N hydrogen chloride in dioxane was stirred at room temperature for 2 hours. The reaction mixture was concentrated under reduced pressure and the residue was dissolved in methanol. This solution was subjected to ion exchange chromatography (Varian SCX) and the column was eluted sequentially with methanol followed by 2N ammonia in methanol. Fractions containing cis-3-methyl-4-(3,5-dichloro-6-fluorobenzofur-7-yl) piperidine were combined and concentrated under reduced pressure. This residue was dissolved in diethyl ether and treated with hydrogen chloride in diethyl ether. The suspension was concentrated under reduced pressure and the residue suspended in diethyl ether. This suspension was filtered and to provide 0.066 gm of cis-3-methyl-4-(3,5-dichloro-6-fluorobenzofur-7-yl)piperidine hydrochloride as a white solid.

High Resolution MS: Calculated for: 302.0514. Found: 302.0503.

Fractions containing cis-1-(tert-butoxycarbonyl)-3-methyl-4-(3-chloro-6-fluorobenzofur-7-yl)piperidine were combined and concentrated under reduced pressure to provide 0.075 gm. This material was treated as described in the previous paragraph to provide 0.034 gm cis-3-methyl-4-(3-chloro-6-fluorobenzofur-7-yl)piperidine hydrochloride as a white solid.

High Resolution MS: Calculated for: 268.0904. Found: 268.0901.

EXAMPLE 31 cis-3-methyl-4-(3-chloro-5-fluorobenzofur-7-yl) piperidine hydrochloride cis-3-methyl-3-(2,3-dichloro-2,3-dihydro-5-fluorobenzofur-7-yl)piperidine hydrochloride A solution of 1.00 gm (2.22 mMol) cis-3-methyl-3-(5-fluorobenzofur-7-yl)piperidine hydrochloride in 125 mL carbon disulfide was cooled to 0° C. A solution of 0.91 gm (5.55 mMol) iodine monochloride in 10 mL carbon disulfide was added and the resulting mixture stirred for 2 hours. The reaction mixture was then concentrated under reduced pressure and the residue dissolved in 100 mL dichloromethane and the resulting solution was concentrated under reduced pressure. This dilution/concentration sequence was repeated 3 times to provide the desired compound as an orange foam.

Dehydrohalogenation

The material recovered from the previous step was dissolved in 200 mL 0.5 N sodium hydroxide in ethanol at 0° C. The mixture was allowed to warm gradually to room temperature. The reaction mixture was adjusted to about pH=1 by the addition of 1N hydrochloric acid. The reaction mixture was concentrated under reduced pressure. The residue was subjected to reverse phase chromatography (Vydac Column), eluting with a gradient of 9:1 to 1:1 1% aqueous hydrochloric acid/acetonitrile. Fractions containing product were combined and concentrated under reduced pressure. This residue was subjected to ion exchange chromatography (Varian SCX column), eluting first with methanol and then with 1 N ammonia in methanol. Fractions containing product were combined and concentrated under reduced pressure to provide 0.29 gm (49%) cis-3-methyl-4-(3-chloro-5-fluorobenzofur-7-yl)piperidine as a waxy white solid. This solid was dissolved in 10 mL ethyl acetate and the resulting solution treated with 3.3 mL 1 N ethanolic hydrogen chloride. The suspension was diluted with 150 mL diethyl ether and was stirred about 16 hours at room temperature. The solid was filtered and dried under vacuum at 60° C. to provide 0.32 gm (96%) of the title compound as a white solid.

High Resolution MS: Calculated for: 268.0904. Found: 268.0911.

EXAMPLE 32

Resolution of cis-3-methyl-4-(6-fluorobenzofur-7-yl)piperidine hydrochloride

One equivalent of racemic cis-3-methyl-4-(6-fluorobenzofur-7-yl)piperidine and one equivalent of S-(−)-

3-bromocamphor-8-sulfonic acid were dissolved in ethanol at reflux. The mixture was allowed to cool to room temperature. The salt which formed was recrystallized from ethanol/ethyl acetate to provide material of 90–95% enantiomeric excess (e.e.). A portion of this material was crystallized from ethyl acetate to provide crystals suitable for X-ray crystallography. The X-ray crystallography experiment was performed as follows:

| Crystal data and structure refinement | |
|---|---|
| Empirical formula | C24 H30 Br F N O5 S |
| Formula weight | 543.46 |
| Temperature | 293(2) K |
| Wavelength | 0.64300 A |
| Crystal system | Monoclinic |
| Space group | P2(1)/n |
| Unit cell dimensions | a = 7.099(2) A |
| | alpha = 90 deg |
| | b = 13.405(4) A |
| | beta = 90 deg |
| from ? reflns with | |
| | c = 26.763(7) A |
| | gamma = 90 deg |
| ?<=theta<=? | |
| | V = 2546.7(13) A^3 Z = 4 |
| Density (calculated) | 1.417 Mg/m^3 |
| Absorption coefficient | 1.737 mm^−1 |
| Crystal size | 0.010 × 0.015 × 0.2 mm |
| Theta range for data collection | 1.38 to 25.33 deg |
| Index ranges | −9<=h<=5, −14<=k<=9, −22<=l<=32 |
| Collection method | /w scans |
| Reflections collected | 5962 [R(int) = 0.1152] |

The X-ray data collected demonstrated that the diastereomer, cis-3-methyl-4-(6-fluorobenzofur-7-yl)piperidine, of this salt was in the 3(R), 4(R) absolute configuration.

This salt (0.80 gm) was treated with 40 mL 1N sodium hydroxide and was extracted well with methyl tert-butyl ether. The combined organic phases were washed sequentially with 50 mL of water and 50 mL saturated aqueous sodium chloride, dried over magnesium sulfate and concentrated under reduced pressure. The residue was dissolved in 5 mL ethyl acetate and this solution was treated with 2 mL 1N hydrogen chloride in diethyl ether. The resulting slurry was diluted with diethyl ether, filtered and the solid dried at 60° C. to provide 0.33 gm (+)-cis-3(R)-methyl-4(R)-(6-fluorobenzofur-7-yl)piperidine hydrochloride.

$[\cdot]_D^{20}$(Methanol, c=10 mg/mL)=61.85°

EA: Calculated for $C_{14}H_{16}NOF$—HCl: C, 62.34; H, 6.35; N, 5.19. Found: C, 61.97; H, 6.24; N, 5.18.

The mother liquor from the original salt crystallization was diluted with aqueous sodium hydroxide and extracted well with methyl tert-butyl ether. The residue was treated with R-(+)-3-bromocamphor-8-sulfonic acid in 1:1 ethanol/ethyl acetate. The salt recovered was recrystallized from 1:1 ethanol/ethyl acetate to provide material of greater than 98% e.e. This salt (0.76 gm ) was converted to the corresponding hydrochloride as previously described to provide 0.19 gm (−)-cis-3(S)-methyl-4(S)-(6-fluorobenzofur-7-yl)piperidine hydrochloride.

$[\cdot]_D^{20}$(Methanol, c=6.49 mg/mL)=−64.71°

Enantiomeric excess was determined by chiral HPLC chromatography employing a ChiralPak AD column, eluting with 99:1:0.1 hexane/ethanol/diethylamine at 1 mL/min at room temperature with the detector 280 nm.

EXAMPLE 33

(−)-cis-3-methyl-4-(5-fluorobenzofur-7-yl)piperidine hydrochloride

A solution of 18 gm (71 mMol) racemic cis-3-methyl-4-(5-fluorobenzofur-7-yl)piperidine in 200 mL 2-butanone was treated with 14 gm (71 mMol) of a mixture of (S)-p-methyl- and (S)-p-bromomandelic acids. The recovered salt was collected by filtration. The salt and mother liquors were combined and concentrated under reduced pressure. The residue was dissolved in 750 mL 2-butanone at reflux and then allowed to stand at room temperature for 3 hours. The recovered salt was recrystallized from 325 mL 2-butanone to provide 8 gm of 99% e.e. material. This salt was converted to the corresponding hydrochloride essentially as described in EXAMPLE 31 to provide (−)-cis-3-methyl-4-(5-fluorobenzofur-7-yl)piperidine hydrochloride.

$[\cdot]_D^{20}$(methanol, c=10.82 mg/mL)=−103.5°

EA: Calculated for $C_{14}H_{16}NOF$—HCl: C, 62.34; H, 6.35; N 5.19. Found: C, 62.25; H, 6.20; N, 5.20.

The opposite diasteromer was separated by preparing the free base of the mother liquor from the first crystallization, and treating this free base with of a mixture of (R)-p-methyl- and (R)-p-bromomandelic acids. The recovered salts were treated as described above to provide (+)-cis-3-methyl-4-(5-fluorobenzofur-7-yl)piperidine hydrochloride.

EXAMPLE 34

3,3-dimethyl-4-(benzofur-7-yl)-1,2,3,6-tetrahydropyridine hydrochloride

Beginning with 7-bromobenzofuran and 1-benzyl-3,3-dimethyl-4-oxopiperidine, 0.34 gm of the title compound were prepared as a yellow solid essentially as described in EXAMPLE 5.

Ion Spray MS: m/e=228 (M+1)

EXAMPLE 35

3,3-dimethyl-4-(6-fluorobenzofur-7-yl)-1,2,3,6-tetrahydropyridine hydrochloride

Beginning with 6-fluoro-7-bromobenzofuran and 1-benzyl-3,3-dimethyl-4-oxopiperidine, 0.15 gm of the title compound were prepared as a tan solid essentially as described in EXAMPLE 5.

Ion Spray MS: m/e=246 (M+1)

EXAMPLE 36

3,3-dimethyl-4-(5-chlorobenzofur-7-yl)-1,2,3,6-tetrahydropyridine hydrochloride

Beginning with 5-chloro-7-bromobenzofuran and 1-benzyl-3,3-dimethyl-4-oxopiperidine, 0.29 gm of the title compound were prepared essentially as described in EXAMPLE 5.

Ion Spray MS: m/e=262 (M+1)

EXAMPLE 37

3,3-dimethyl-4-(5-chlorobenzofur-7-yl)piperidine hydrochloride

Beginning with 5-chloro-7-bromobenzofuran and 1-benzyl-3,3-dimethyl-4-oxopiperidine, 0.23 gm of the title compound were prepared as an off-white solid essentially as described in EXAMPLE 27.

EA: Calculated for $C_{15}H_{18}NOCl$—HCl: C, 60.01; H, 6.38; N, 4.62. Found: C, 59.85; H, 6.43; N, 4.65.

EXAMPLE 38

3,3-dimethyl-4-(5-fluorobenzofur-7-yl)piperidine hydrochloride

Beginning with 0.20 gm (0.82 mMol) 3,3-dimethyl-4-(5-fluorobenzofur-7-yl)-1,2,3,6-tetrahydropyridine, 0.063 gm of the title compound were prepared essentially as described in EXAMPLE 4.

Ion Spray MS: m/e=248 (M+1)

EXAMPLE 39 cis-3-ethyl-4-(5-fluorobenzofur-7-yl)piperidine hydrochloride

Beginning with 5-fluoro-7-bromobenzofuran and 1-benzyl-3-ethyl-4-oxopiperidine, the title compound was prepared as a light tan solid essentially as described in EXAMPLE 16.

High Resolution MS: Calculated for: 248.1450. Found: 248.1443.

EXAMPLE 40

(−)-cis-3-methyl-4-(5,6-difluorobenzofur-7-yl) piperidine hydrochloride

A solution of 5.3 gm racemic cis-3-methyl-4-(5,6-difluorobenzofur-7-yl)piperidine in 117 Ml 0.18 M L-tartaric acid mixture in ethanol was heated at reflux. (The L-tartaric acid mixture was prepared by dissolving 15 mMol of each of di-p-anisoyl-L-tartaric acid, dibenzoyl-L-tartaric acid, and di-p-toluoyl-L-tartaric acid in 250 Ml ethanol.) The solution was allowed to cool to room temperature and the solid was collected by filtration. This solid was recrystallized from 370 Ml 4:1 ethanol/water, and the recovered solid recrystallized from 250 Ml 1:1 ethanol/water to provide 2 gm of salt of about 96% e.e. This salt was partitioned between 10% sodium hydroxide and methyl tert-butyl ether. The organic phase was concentrated under reduced pressure and the residue converted to the hydrochloride salt to provide the title compound.

$[\cdot]_D^{20}$(methanol, c=10.5 mg/Ml)=−58.88°

EA: Calculated for $C_{14}H_{15}NOF_2$—HCl: C, 58.44; H, 5.60; N, 4.86. Found: C, 58.40; H, 5.60; N, 4.88.

EXAMPLE 41

3,3-dimethyl-4-(4,5-difluorobenzofur-7-yl)-1,2,3,6-tetrahydropyridine hydrochloride Beginning with 4,5-difluoro-7-bromobenzofuran and 1-benzyl-3,3-dimethyl-4-oxopiperidine, the title compound was prepared essentially as described in EXAMPLE 5.

EXAMPLE 42 trans-3-methyl-4-(5-fluorobenzofur-7-yl)piperidine hydrochloride

A mixture of cis- and trans-1-benzyl-3-methyl-4-(5-fluorobenzofur-7-yl)piperidine was prepared essentially as described in EXAMPLE 16. This mixture was dissolved in hexane and was subjected to silica gel chromatography, eluting with a gradient of 100% hexane/0% ethyl acetate to 0% hexane/100% ethyl acetate. Fractions containing trans-1-benzyl-3-methyl-4-(5-fluorobenzofur-7-yl)piperidine were combined and concentrated under reduced pressure to provide 0.84 gm of the desired compound. The benzyl group was cleaved and the salt formed essentially as described in EXAMPLE 3 to provide 0.60 gm (86%) of the title compound as an off-white solid.

High Resolution MS: Calculated for: 234.1294. Found: 234.1280.

EXAMPLE 43 cis-3-methyl-4-(benzofur-7-yl)piperidine hydrochloride

Beginning with 7 gm (35.5 mMol) 7-bromobenzofuran and 7.9 gm (39 mMol) 1-benzyl-3-methyl-4-oxopiperidine, 1.92 gm (21%) of the title compound were prepared as a white powder essentially as described in EXAMPLE 19.

EA: Calculated for $C_{14}H_{17}NO$—HCl: C, 66.79; H, 7.21; N, 5.56. Found: C, 66.41; H, 7.02; N, 5.70.

EXAMPLE 44 cis-3-methyl-4-(3-chlorobenzofur-7-yl)piperidine hydrochloride

Beginning with 0.50 gm (2.0 mMol) cis-3-methyl-4-(benzofur-7-yl)piperidine hydrochloride, 0.62 gm (31%) of the title compound were prepared as an off-white solid, essentially as described in EXAMPLE 31.

High Resolution MS: Calculated for: 250.0998. Found: 250.1016.

EXAMPLE 45

Resolution of cis-3-methyl-4-(4,5,6-trifluorobenzofur-7-yl)piperidine

Beginning with 1.65 gm cis-3-methyl-4-(4,5,6-trifluorobenzofur-7-yl)piperidine, the individual diastereomers were prepared essentially as described in EXAMPLE 33, except that successive crystallizations of the respective 3-bromocamphor-8-sulfonic acid salts were performed in isopropanol.

EXAMPLE 46

3,5-dimethyl-4-(5-fluorobenzofur-7-yl)piperidine hydrochloride

Beginning with 5-fluoro-7-bromobenzofuran and 1-benzyl-3,5-dimethyl-4-oxopiperidine, the title compound was prepared as a yellowish solid essentially as described in EXAMPLE 18.

EXAMPLE 47 cis-3-methyl-4-(6-fluorobenzofur-4-yl)piperidine hydrochloride 1-benzyl-3-methyl-4-hydroxy-4-(6-fluorobenzofur-4-yl)piperidine and 1-benzyl-3-methyl-4-hydroxy-4-(4-fluorobenzofur-6-yl)piperidine Beginning with 1.45 gm (6.74 mMol) of a mixture of 4-bromo-6-fluorobenzofuran and 4-fluoro-6-bromobenzofuran and 2.0 gm (13.5 mMol) 1-benzyl-3-methyl-4-oxopiperidine, 0.77 gm of the desired mixture were prepared essentially as described in EXAMPLE 18.

Ion Spray MS: m/e=340 (M+1)

cis-1-benzyl-3-methyl-4-(6-fluorobenzofur-4-yl) piperidine and cis-1-benzyl-3-methyl-4-(4-fluorobenzofur-6-yl)piperidine Beginning with 0.77 gm (2.3 mMol) of a mixture of 1-benzyl-3-methyl-4-hydroxy-4-(6-fluorobenzofur-4-yl) piperidine and 1-benzyl-3-methyl-4-hydroxy-4-(4-fluorobenzofur-6-yl)piperidine, 0.42 gm of the desired mixture were prepared essentially as described in EXAMPLE 18.

Ion Spray MS: m/e=324 (M+1)

cis-3-methyl-4-(6-fluorobenzofur-4-yl)piperidine and cis-3-methyl-4-(4-fluorobenzofur-6-yl) piperidine Beginning with 0.40 gm (1.2 mMol) of a mixture of cis-1-benzyl-3-methyl-4-(6-fluorobenzofur-4-yl)piperidine and cis-1-benzyl-3-methyl-4-(4-fluorobenzofur-6-yl)piperidine, 0.12 gm of the desired mixture were prepared essentially as described in EXAMPLE 3.

Separation of Isomers

A suspension of 0.12 gm (0.51 mMol) of a mixture of cis-3-methyl-4-(6-fluorobenzofur-4-yl)piperidine and cis-3-methyl-4-(4-fluorobenzofur-6-yl)piperidine and 0.077 gm (0.56 mMol) potassium carbonate in 2 mL tetrahydrofuran and 2 mL water was cooled to 0° C. To this suspension was added a solution of 0.12 gm (0.54 mMol) di-tert-butyl dicarbonate in 2 mL tetrahydrofuran. The reaction mixture was allowed to warm to room temperature. After 2 hours the reaction mixture was partitioned between ethyl acetate and water. The organic phase was dried over magnesium sulfate and concentrated under reduced pressure to provide 0.15 gm of a mixture of cis-1-tert-butoxycarbonyl-3-methyl-4-(6-fluorobenzofur-4-yl)piperidine and cis-1-tert-butoxycarbonyl-3-methyl-4-(4-fluorobenzofur-6-yl)piperidine. This residue was subjected to silica gel chromatography, eluting with hexane containing 10% ethyl acetate. Fractions containing the second eluting isomer were combined and concentrated under reduced pressure to provide 0.042 gm cis-1-tert-butoxycarbonyl-3-methyl-4-(6-fluorobenzofur-4-yl)piperidine. A solution of this residue in i mL tetrahydrofuran was treated with 3 mL 1M hydrogen chloride in diethyl ether. The mixture was diluted with diethyl ether and was stored in a refrigerator. After about 72 hours, the mixture was filtered to provide 0.006 gm of the title compound as a white solid.

Ion Spray MS: 234 (M+1).

EXAMPLE 48

2-methyl-4-(4-trifluoromethylbenzofur-7-yl)-1,2,3,6-tetrahydropyridine hydrochloride and 2-methyl-4-(4-trifluoromethylbenzofur-7-yl)-1,2,5,6-tetrahydropyridine hydrochloride Beginning with 0.60 gm (2.28 mMol) 4-trifluoromethyl-7-bromobenzofuran and 1-(tert-butoxycarbonyl)-2-methyl-4-oxopiperidine, 0.070 gm of a mixture of the title compounds was prepared essentially as described in EXAMPLE 1.

MS(ES+): m/e=282 (M+1)

$^1$H-NMR(MeOH-d$_4$): δ8.02 (s, 1H), 7.60 (d, J=7.50 Hz, 1H), 7.50 (d, J=7.30 Hz, 1H), 7.05 (s,1H), 6.70 (s, 0.6H), 6.59 (s, 0.4H), 4.25–4.10 (m, 0.4H), 4.05–3.85 (m), 3.46–3.36 (m), 3.10–2.82 (m), 2.82–2.60(m), 1.58–1.35 (m, 3H).

EXAMPLE 49

2-methyl-4-(465-difluorobenzofur-7-yl)-1,2,3,6-tetrahydropyridine hydrochloride and 2-methyl-4-(4,5-difluorobenzofur-7-yl)-1,2,5,6-tetrahydropyridine hydrochloride Beginning with 4,5-difluoro-7-bromobenzofuran and 1-(tert-butoxycarbonyl)-2-methyl-4-oxo-piperidine, 0.078 gm of a mixture of the title compounds was prepared essentially as described in EXAMPLE 1.

MS(IS): m/e=250 (M+1)

EXAMPLE 50

2-methyl-4-(4-chloro-5-fluorobenzofur-7-yl)-1,2,3,6-tetrahydropyridine hydrochloride and 2-methyl-4-(4-chloro-5-fluorobenzofur-7-yl)-1,2,5,6-tetrahydropyridine hydrochloride Beginning with 4-chloro-5-fluoro-7-bromobenzofuran and 1-(tert-butoxycarbonyl)-2-methyl-4-oxo-piperidine, 0.035 gm of a mixture of the title compounds was prepared essentially as described in EXAMPLE 1.

MS(IS): m/e=266 (M+1)

EXAMPLE 51

2-methyl-4-(5,6-difluorobenzofur-7-yl)-1,2,3,6-tetrahydropyridine hydrochloride and 2-methyl-4-(5,6-difluorobenzofur-7-yl)-1,2,5,6-tetrahydropyridine hydrochloride A solution of 2.28 gm (9.8 mMol) 5,6-difluoro-7-bromobenzofuran in 30 mL tetrahydrofuran was cooled to −78° C. and then 9.8 mL (19.6 mMol) tert-butyllithium (1.7M in tetrahydrofuran) were added. After stirring for 30 minutes, a solution of 1.9 gm (8.9 mMol) 1-(tert-butoxycarbonyl)-2-methyl-4-oxo-piperidine in 20 mL tetrahydrofuran was added dropwise over 30 minutes. The reaction mixture was allowed to warm to room temperature over 16 hours and was then concentrated under reduced pressure. The residue was dissolved in 200 mL ethyl acetate and extracted sequentially with 50 mL 1N hydrochloric acid, saturated aqueous sodium bicarbonate, and saturated aqueous sodium chloride. The remaining organic phase was dried over magnesium sulfate and concentrated under reduced pressure to provide 1-(tert-butoxycarbonyl)-2-methyl-4-hydroxy-4-(5,6-difluorobenzofur-7-yl)piperidine. This alcohol was converted to a mixture of the title compounds essentially as described in EXAMPLE 1.

MS(IS): m/e=250 (M+1)

EXAMPLE 52

2-ethyl-4-(5-fluorobenzofur-7-yl)-1,2,3,6-tetrahydropyridine hydrochloride and 2-ethyl-4-(5-fluorobenzofur-7-yl)-1,2,5,6-tetrahydropyridine fumarate Beginning with 5-fluoro-7-bromobenzofuran and 1-(tert-butoxycarbonyl)-2-ethyl-4-oxo-piperidine, a mixture of the title compounds was prepared essentially as described in EXAMPLE 1.

ISMS: m/e=246

EXAMPLE 53

2-ethyl-4-(4-trifluoromethylbenzofur-7-yl)-1,2,3,6-tetrahydropyridine hydrochloride and 2-ethyl-4-(4-trifluoromethylbenzofur-7-yl)-1,2,5,6-tetrahydropyridine Beginning with 4-trifluoromethyl-7-bromobenzofuran and 1-(tert-butoxycarbonyl)-2-ethyl-4-oxo-piperidine, a mixture of the title compounds was prepared essentially as described in EXAMPLE 1.

ISMS: m/e 296

EXAMPLE 54

Cis- and trans-2-methyl-4-(4-trifluoromethylbenzofur-7-yl)piperidine hydrochloride Beginning with 1.5 gm (7.11 mMol) 4-trifluoromethyl-7-bromobenzofuran and 1-benzyl-2-methyl-4-oxopiperidine, 0.171 gm of a mixture comprising cis- and trans-2-methyl-4-(4-trifluoromethylbenzofur-7-yl)piperidine essentially was prepared essentially as described in EXAMPLE 16. This mixture was subjected to silica gel chromatography to provide the individual isomers. Cis-2-methyl-4-(4-trifluoromethylbenzofur-7-yl)piperidine was treated with hydrogen chloride in diethyl ether to provide 0.052 gm (26%) of the corresponding hydrochloride salt.

$^1$H-NMR(DMSO-$d_6$): δ9.39 (br. d. 1H), 8.28 (d, J=2.2 Hz, 1H), 7.64 (d, J=7.9 Hz, 1H), 7.35 (d, J=7.8 Hz, 1H) 7.09 (m,1H), 3.51 (dddd appearing as tt, J=12.1 Hz, 12.1 Hz, 3.5 Hz, 3.5 Hz, 1H), 3.47–3.32 (m, 2H), 3.18–3.05 (m, 1H), 2.18–1.95(m, 3H), 1.89 (ddd appearing as q, J=12.2 Hz, 1H).

MS(ES+): m/e=284 (M+1)

Trans-2-methyl-4-(4-trifluoromethylbenzofur-7-yl)piperidine was similarly treated with hydrogen chloride in diethyl ether to provide 0.015 gm (8%) of the corresponding hydrochloride salt.

$^1$H-NMR(DMSO-$d_6$): δ9.20 (br. s. 1H), 9.00 (br. s. 1H), 8.28 (d, J=2.2 Hz, 1H), 7.64 (d, J=7.8 Hz, 1H), 7.39 (d, J=7.8 Hz, 1H) 7.09 (m,1H), 3.78–3.64 (m, 2H), 3.35–3.22 (m, 1H), 3.16 (ddd, J=13.1 Hz, 4.1 Hz, 4.1 Hz, 1H), 2.27 (ddd, J=14.2 Hz, 11.4 Hz, 4.7 Hz, 1H), 2.20–2.02 (m, 2H), 1.91 (ddd, J=13.9 Hz, 3.3 Hz, 3.3 Hz, 1H), 1.43 (d, J=6.9 Hz, 3H).

MS(ES+): m/e=284 (M+1)

EXAMPLE 55

3,3-dimethyl-4-(4-chlorobenzofur-7-yl)-1,2,3,6-tetrahydropyridine hydrochloride

Beginning with 7-bromo-4-chlorobenzofuran, the title compound was prepared essentially as described in EXAMPLE 5.

HRMS: Calculated for $C_{15}H_{17}NOCl$: 262.0999. Found: 262.1015.

EA: Calculated for $C_{15}H_{17}NOCl—HCl$: C, 60.61; H, 5.74; N, 4.69. Found: C, 60.08; H, 5.53; N, 4.40.

EXAMPLE 56

3,3-dimethyl-4-(5-methoxybenzofur-7-yl)-1,2,3,6-tetrahydropyridine hydrochloride Beginning with 7-bromo-5-methoxybenzofuran, the title compound was prepared essentially as described in EXAMPLE 5.

HRMS: Calculated for $C_{16}H_{20}NO_2$: 258.1494. Found: 258.1505.

EXAMPLE 57

3,3-dimethyl-4-(4-fluorobenzofur-7-yl)-1,2,3,6-tetrahydropyridine hydrochloride

Beginning with 7-bromo-4-fluorobenzofuran, the title compound was prepared essentially as described in EXAMPLE 5.

HRMS: Calculated for $C_{15}H_{17}NOF$: 246.1294. Found: 246.1290.

EXAMPLE 58

3,3-dimethyl-4-(5,6-difluorobenzofur-7-yl)-1,2,3,6-tetrahydropyridine hydrochloride Beginning with 3.38 gm (14.5 mMol) 7-bromo-5,6-difluorobenzofuran and 3.0 gm (13.8 mMol) 1-benzyl-3,3-dimethyl-4-oxopiperidine, 3.7 gm (68%) 1-benzyl-3,3-dimethyl-4-hydroxy-4-(5,6-difluorobenzofur-7-yl)piperidine were prepared essentially as described in EXAMPLE 51.

ISMS: m/e=372 (M+1)

This tertiary alcohol was converted to 0.12 gm of the title compound essentially as described in EXAMPLE 5.

HRMS: Calculated for $C_{15}H_{16}NOF_2$: 264.1200. Found: 264.1188.

EXAMPLE 59 cis-3-hydroxymethyl-4-(5-fluorobenzofur-7-yl)piperidine hydrochloride

Beginning with 7-bromo-5-fluorobenzofuran and 1-benzyl-3-(tert-butyldimethylsilyloxy)methyl-4-oxopiperidine, the title compound was prepared essentially as described in EXAMPLE 16.

ISMS: m/e=250 (M+1)

EXAMPLE 60

Alternate Synthesis of 3,3-dimethyl-4-(4,5-difluorobenzofur-7-yl)-1,2,3,6-tetrahydropyridine hydrochloride A solution of 0.483 gm (1.34 mMol) 1-(tert-butoxycarbonyl)-3,3-dimethyl-4-trifluoromethanesulfonyloxy-1,2,3,6-tetrahydropyridine in 5 mL previously deoxygenated 9:1 toluene:n-propanol was placed under vacuum and pressurized with nitrogen three times to exclude oxygen. To this solution were added 0.008 gm (0.036 mMol) palladium acetate and 0.024 gm (0.092 mMol) triphenylphosphine and the resulting mixture was stirred for 15 minutes. Then 0.28 gm (1.41 mMol) 4,5-difluorobenzofur-7-ylboronic acid, 0.085 gm (2.0 mMol) lithium chloride, and 0.74 mL (1.48 mMol) of previously deoxygenated 2.0 M aqueous sodium carbonate were added to the reaction mixture. The mixture was deoxygenated by subjecting it three times to a vacuum/nitrogen cycle, was heated to reflux for 4 hours, and was stirred at room temperature for 16 hours. The reaction mixture was then partitioned between water and diethyl ether. The aqueous phase was extracted well with diethyl ether and all of the organic phases were combined, dried over sodium sulfate and concentrated under reduced pressure. The residue was subjected to silica gel chromatography, eluting with 20% ethyl acetate in hexanes. Fractions containing product were combined and concentrated under reduced pressure to provide 0.374 gm (76.6%) 1-(tert-butoxycarbonyl)-3,3-dimethyl-4-(4,5-difluorobenzofur-7-yl)-1,2,3,6-tetrahydropyridine as a crystalline white solid. A solution of 0.246 gm (0.68 mMol) 1-(tert-butoxycarbonyl)-3,3-dimethyl-4-(4,5-difluorobenzofur-7-yl)-1,2,3,6-tetrahydropyridine in 3 mL 2 M hydrogen chloride in ethyl acetate was stirred at room temperature for 3 hours. The reaction mixture was concentrated under reduced pressure to provide 0.202 gm of the title compound as an off-white solid.

EXAMPLE 61

3,3-dimethyl-4-(4-trifluoromethylbenzofur-7-yl)-1,2,3,6-tetrahydropyridine fumarate Beginning with (4-trifluoromethylbenzofur-7-yl)boronic acid, the title compound was prepared essentially as described in EXAMPLE 60.

m.p.=179.6–180.9° C.

EA: Calculated for $C_{16}H_{16}NOF_3—C_4H_4O_4$: C, 58.39; H, 4.90; N, 3.40. Found: C, 58.09; H, 4.78; N, 3.43.

EXAMPLE 62

Alternate Synthesis of 2-methyl-4-(4,5-difluorobenzofur-7-yl)-1,2,3,6-tetrahydropyridine hydrochloride A mixture of 0.5 gm (2.53 mMol) 4,5-difluorobenzofur-7-ylboronic acid, 0.872 gm (2.53 mMol) 1-(tert-butoxycarbonyl)-2-methyl-4-trifluoromethanesulfonyloxy-1,2,3,6-tetrahydropyridine, 0.806 gm (3.8 mMol) potassium phosphate, and 0.146 gm (0.127 mMol) tetrakis(triphenylphosphino)palladium in 10 mL tetrahydrofuran was placed under vacuum and pressurized with nitrogen three times to exclude oxygen. The reaction mixture was heated at reflux for 3 hours and was then poured into 250 mL diethyl ether and filtered through a pad of celite. The filter pad was washed with 200 mL diethyl ether and the combined filtrates were concentrated under reduced pressure. The residue was subjected to silica gel chromatography, eluting with hexane followed by 9% ethyl acetate in hexane. Fractions containing the desired product were combined and concentrated under reduced pressure to provide 0.65 gm (74%) 1-(tert-butoxycarbonyl)-2-methyl-4-(4,5-difluorobenzofur-7-yl)-1,2,3,6-tetrahydropyridine. A solution of 0.62 gm (1.77 mMol) 1-(tert-butoxycarbonyl)-2-methyl-4-(4,5-difluorobenzofur-7-yl)-1,2,3,6-tetrahydropyridine in 10 mL 4 M hydrogen chloride in dioxane was stirred at room temperature for 2 hours. The reaction mixture was concentrated under reduced pressure and the residue slurried in diethyl ether to provide 0.44 gm (86%) of the title compound.

EXAMPLE 63

Alternate Synthesis of 2-methyl-4-(5-fluorobenzofur-7-yl)-1,2,3,6-tetrahydropyridine hydrochloride Beginning with 7-bromo-5-fluorobenzofuran and 1-benzyl-2-methyl-4-oxopiperidine, the title compound was prepared essentially as described in EXAMPLE 3.

HRMS: Calculated for $C_{14}H_{15}NOF$: 232.1134. Found: 232.1138.

EXAMPLE 64

Resolution of racemic cis-3-methyl-4-(benzofur-7-yl)piperidine

A mixture of 0.7 gm (3.2 mMol) racemic cis-3-methyl-4-(benzofur-7-yl)piperidine and 1.4 gm (3.1 mMol) (+)-ortho-, meta-, and para-chlorobenzoyltartaric acids were dissolved in 5 mL 2-butanone at reflux. The mixture was cooled to 20° C. and the precipitate collected by filtration. This solid was dissolved in 140 mL 2-butanone and was stirred at room temperature for 3 days. During this time, 40 mL of the solvent evaporated. The precipitate that formed was collected by filtration to provide 0.050 gm of salt (e.e.=92%). This salt was dissolved in 20 mL 2-butanone and was stirred at room temperature for 2 days. During this time, 5 mL of the solvent evaporated. The precipitated that formed was collected by filtration to provide 0.020 gm of salt (e.e.=97.7%).

Enantiomeric purities were determined by HPLC using a Chiralcel OD column, eluting with 99:1:0.1 hexane:ethanol:diethylamine. Flow rate=1.0 mL/min. The retention time of the two enantiomers were 13.2 and 15.8 minutes.

EXAMPLE 65

(−)-cis-3-methyl-4-(2-methyl-5-fluorobenzofur-7-yl)piperidine hydrochloride (−)-cis-1-(tert-butoxycarbonyl)-3-methyl-4-(5-fluorobenzofur-7-yl)piperidine A solution of 1.0 gm (3.7 mMol) (−)-cis-3-methyl-4-(5-fluorobenzofur-7-yl)piperidine in 80 mL dichloromethane was cooled in an ice bath and then treated with 25 mL saturated aqueous sodium bicarbonate followed by the dropwise addition of a solution of 1.21 gm (5.56 mMol) di-tert-butyl dicarbonate in 20 mL dichloromethane. The reaction mixture was stirred for 11 hours and the phases were separated. The aqueous phase was extracted well with dichloromethane. All of the organic phases were combined, dried over magnesium sulfate and concentrated under reduced pressure. The residue was subjected to silica gel chromatography, eluting with hexane containing from 0–25% ethyl acetate. Fractions containing the desired product were combined and concentrated under reduced pressure to provide 1.15 gm (−)-cis-1-(tert-butoxycarbonyl)-3-methyl-4-(5-fluorobenzofur-7-yl)piperidine.

Alkylation

A solution of 0.100 gm (0.3 mMol) (−)-cis-1-(tert-butoxycarbonyl)-3-methyl-4-(5-fluorobenzofur-7-yl)piperidine in 2 mL tetrahydrofuran was cooled to −78° C. To this solution were added 0.38 mL (0.6 mMol) n-butyllithium (1.6 M in hexane) dropwise. After stirring for 5 minutes, 0.02 mL (0.33 mMol) iodomethane were added and the reaction mixture was stirred at −78° C. for 3 hours. The solution was treated with an additional 0.06 mL (0.1 mMol) n-butyllithium (1.6 M in hexane) followed by 0.02 mL (0.33 mMol) iodomethane. After stirring for 1 hour at −78° C., an additional 0.06 mL (0.1 mMol) n-butyllithium (1.6 M in hexane) followed by 0.02 mL (0.33 mMol) iodomethane were added to the reaction mixture. The mixture was then stirred at room temperature for 14 hours and was then partitioned between 5 mL deionized water and 40 mL ethyl acetate. The organic phase was washed sequentially with 20 mL portions of saturated aqueous sodium bicarbonate and saturated aqueous sodium chloride. The organic phase was then dried over magnesium sulfate and concentrated under reduced pressure to provide (−)-cis-1-(tert-butoxycarbonyl)-3-methyl-4-(2-methyl-5-fluorobenzofur-7-yl)piperidine.

Deprotection/Salt Formation

A solution of 0.104 gm (0.3 mMol) (−)-cis-1-(tert-butoxycarbonyl)-3-methyl-4-(2-methyl-5-fluorobenzofur-7-yl)piperidine in 2 mL dichloromethane was treated with 2.0 mL (8 mMol) hydrogen chloride (4N in dioxane). The mixture was stirred at room temperature for 2 hours and was then concentrated under reduced pressure. The residue was subjected to chromatography on a preparative Vydac C-18 column, eluting with a gradient of 90% deionized water containing 0.1% hydrochloric acid:10% acetonitrile to 50% deionized water containing 0.1% hydrochloric acid:50% acetonitrile over 100 minutes, and then maintaining the final solvent concentration for an additional 30 minutes. Fractions containing product were combined and concentrated under reduced pressure. The residue was lyophilized to provide 0.023 gm (27%) of the title compound.

HRMS: Calculated for $C_{15}H_{19}NOF$: 248.1450. Found: 248.1456.

EXAMPLE 66

3-(5-Fluorobenzofur-7-yl)pyrrolidine hydrochloride

A mixture of 0.675 g (3.14 mMol) 7-bromo-5-fluorobenzofuran, 5.0 g (31.40 mMol)1-benzyl-3-pyrroline, 2.19 mL (12.56 mMol), N,N-diisopropylethylamine, 0.399 g (9.42 mMol) LiCl, 0.154 g (0.66 mMol) tri-2-furylphosphine, and 0.070 g (0.314 mMol) palladium diacetate in 10 mL N,N-dimethylformamide was heated under nitrogen at 100° C. for 48 hours. The mixture was diluted with 10 mL diethyl ether and filtered through celite. The filtrate was concentrated under reduced pressure and the oily residue was submitted to kugelrohr distillation to remove most of the pyrrole and pyrrolidine side-products. Flash chromatography of the residue (Et$_3$N/Et$_2$O/hexane 1:39:60) yielded 1-benzyl-3-(5-fluorobenzofur-7-yl)pyrrolidine (173 mg, 19%) as a colorless oil.

HRMS calculated for C$_{19}$H$_{19}$FNO: 296.1450; found: 296.1437.

1-Benzyl-3-(5-fluorobenzofur-7-yl)pyrrolidine was debenzylated with 1-chloroethyl chloroformate and converted to the free amine, essentially as described in EXAMPLE 3.

The hydrochloride salt was prepared as described in EXAMPLE 4.

HRMS calculated for C$_{12}$H$_{13}$FNO: 206.0981; found: 206.0985.

EXAMPLE 67

2-methyl-4-(5-fluorobenzofur-7-yl)-1,2,5,6-tetrahydropyridine hydrochloride 1-(tert-butoxycarbonyl)-2-methyl-4-(5-fluorobenzofur-7-yl)-1,2,5,6-tetrahydropyridine A flask purged of oxygen and under a nitrogen atmosphere was charged with 0.104 gm (0.482 mMol) 5-fluoro-7-bromobenzofuran, 0.184 gm (0.723 mMol) bis(pinacolato) di-boron, 0.0043 gm (0.0024 mMol) palladium(II) chloride, 0.016 gm (0.0029 mMol) 1,1'-bis(diphenylphosphino)ferrocene, 0.142 gm (1.45 mMol) potassium acetate, and 3 mL toluene. This mixture was heated at 90° C. for 5 hours and was then poured into 150 mL diethyl ether and filtered through a bed of celite. The filtrate was concentrated under reduced pressure to provide a dark residue. This material was dissolved in 3 mL tetrahydrofuran and the resulting solution purged of oxygen and placed under a nitrogen atmosphere. To this solution were added 0.028 gm (0.0024 mMol) tetrakis(triphenylphosphino)palladium(0), 0.153 gm (0.723 mMol) potassium phosphate, and 0.15 gm (0.434 mMol) 1-(tert-butoxycarbonyl)-2-methyl-4-trifluoromethylsulfonyloxy-1,2,5,6-tetrahydropyridine. The resulting mixture was stirred at reflux for 3.5 hours and was then charged with an additional 0.5 equivalents of 1-(tert-butoxycarbonyl)-2-methyl-4-trifluoromethylsulfonyloxy-1,2,5,6-tetrahydropyridine. The mixture was stirred at reflux for an additional 1.5 hours and was then poured into 150 mL diethyl ether. The mixture was filtered through a bed of celite and the filtrate concentrated under reduced pressure. The residue was dissolved in 2 mL dichloromethane and the solution was subjected to silica gel chromatography, eluting with a gradient of hexane containing 0–5% ethyl acetate. Fractions containing product were combined and concentrated under reduced pressure to provide 0.10 gm (62%) of the desired compound.

M.S.(ES$^+$): m/e=331.9 (M+1)

HRMS calculated for C$_{19}$H$_{22}$FNO$_3$: 332.1662; found: 332.1657.

Deprotection/salt Formation

A mixture of 0.09 gm (0.272 mMol) 1-(tert-butoxycarbonyl)-2-methyl-4-(5-fluorobenzofur-7-yl)-1,2,5,6-tetrahydropyridine in 10 mL 4N hydrogen chloride in dioxane was stirred at room temperature for 2 hours. The reaction mixture was concentrated under reduced pressure and the residue suspended in diethyl ether. The suspension was filtered and the solid dried under reduced pressure to provide 0.051 gm (70%) of the title compound as a white solid.

HRMS calculated for C$_{14}$H$_{13}$FNO: 232.1138; found: 232.1152.

EXAMPLE 68

2-methyl-4-(4-chlorobenzofur-7-yl)-1,2,5,6-tetrahydropyridine hydrochloride

Beginning with 0.112 gm (0.482 mMol) 4-chloro-7-bromobenzofuran and 0.150 gm (0.434 mMol) 1-(tert-butoxycarbonyl)-2-methyl-4-trifluoromethylsulfonyloxy-1,2,5,6-tetrahydropyridine, 0.093 gm (56%) 1-(tert-butoxycarbonyl)-2-methyl-4-(4-chlorobenzofur-7-yl)-1,2,5,6-tetrahydropyridine was prepared essentially as described in EXAMPLE 67.

M.S.(ES$^+$): m/e=347.9

This material was treated essentially as described in EXAMPLE 67 to provide 0.072 gm (98%) of the title compound.

HRMS calculated for C$_{14}$H$_{13}$ClNO: 248.0842; found: 248.0875.

EXAMPLE 69

2-methyl-4-(4-chlorobenzofur-7-yl)-1,2,3,6-tetrahydropyridine hydrochloride

Beginning with 0.112 gm (0.482 mMol) 4-chloro-7-bromobenzofuran and 0.150 gm (0.434 mMol) 1-(tert-butoxycarbonyl)-2-methyl-4-trifluoromethylsulfonyloxy-1,2,3,6-tetrahydropyridine, 0.117 gm (70%) 1-(tert-butoxycarbonyl)-2-methyl-4-(4-chlorobenzofur-7-yl)-1,2,3,6-tetrahydropyridine was prepared essentially as described in EXAMPLE 67.

M.S.(ES$^+$): m/e=347.9

This material was treated essentially as described in EXAMPLE 67 to provide 0.089 gm of the title compound.

HRMS calculated for C$_{14}$H$_{13}$ClNO: 248.0842; found: 248.0837.

EXAMPLE 70

2-methyl-4-(4,5-difluorobenzofur-7-yl)-1,2,5,6-tetrahydropyridine hydrochloride

Beginning with 0.112 gm (0.482 mMol) 4,5-difluoro-7-bromobenzofuran and 0.150 gm (0.434 mMol) 1-(tert-butoxycarbonyl)-2-methyl-4-trifluoromethylsulfonyloxy-1,2,5,6-tetrahydropyridine, 0.106 gm (63%) 1-(tert-butoxycarbonyl)-2-methyl-4-(4,5-difluorobenzofur-7-yl)-1,2,5,6-tetrahydropyridine was prepared essentially as described in EXAMPLE 67.

M.S.(ES$^+$): m/e=349.9

HRMS calculated for C$_{19}$H$_{21}$F$_2$NO$_3$: 350.1568; found: 350.1560.

This material was treated essentially as described in EXAMPLE 67 to provide 0.054 gm of the title compound.

HRMS calculated for C$_{14}$H$_{12}$F$_2$NO: 250.1043; found: 250.1063.

EXAMPLE 71

2-methyl-4-(4,5-difluorobenzofur-7-yl)-1,2,3,6-tetrahydropyridine hydrochloride

Beginning with 0.112 gm (0.482 mMol) 4,5-difluoro-7-bromobenzofuran and 0.150 gm (0.434 mMol) 1-(tert-butoxycarbonyl)-2-methyl-4-trifluoromethylsulfonyloxy-1, 2,3,6-tetrahydropyridine, 0.089 gm 1-(tert-butoxycarbonyl)-2-methyl-4-(4,5-difluorobenzofur-7-yl)-1,2,3,6-tetrahydropyridine was prepared essentially as described in EXAMPLE 67.

M.S.(ES$^+$): m/e=349.9

This material was treated essentially as described in EXAMPLE 67 to provide the title compound.

HRMS calculated for $C_{14}H_{12}F_2NO$: 250.1043; found: 250.1041.

EXAMPLE 72

2-methyl-4-(5,6-difluorobenzofur-7-yl)-1,2,5,6-tetrahydropyridine hydrochloride

Beginning with 0.112 gm (0.482 mMol) 5,6-difluoro-7-bromobenzofuran and 0.150 gm (0.434 mMol) 1-(tert-butoxycarbonyl)-2-methyl-4-trifluoromethylsulfonyloxy-1,2,5,6-tetrahydropyridine, 0.086 gm (51%) 1-(tert-butoxycarbonyl)-2-methyl-4-(5,6-difluorobenzofur-7-yl)-1,2,5,6-tetrahydropyridine was prepared essentially as described in EXAMPLE 67.

M.S.(ES$^+$): m/e=349.9

HRMS calculated for $C_{19}H_{21}F_2NO_3$: 350.1568; found: 350.1570.

This material was treated essentially as described in EXAMPLE 67 to provide 0.063 gm (93%) of the title compound.

HRMS calculated for $C_{14}H_{12}F_2NO$: 250.1043; found: 250.1051.

EXAMPLE 73

2-methyl-4-(4-chloro-5-fluorobenzofur-7-yl)-1,2,5,6-tetrahydropyridine hydrochloride Beginning with 0.120 gm (0.482 mMol) 4-chloro-5-fluoro-7-bromobenzofuran and 0.150 gm (0.434 mMol) 1-(tert-butoxycarbonyl)-2-methyl-4-trifluoromethylsulfonyloxy-1,2,5,6-tetrahydropyridine, 0.096 gm (55%) 1-(tert-butoxycarbonyl)-2-methyl-4-(4-chloro-5-fluorobenzofur-7-yl)-1,2,5,6-tetrahydropyridine was prepared essentially as described in EXAMPLE 67.

M.S.(ES$^+$): m/e=365.9

HRMS calculated for $C_{19}H_{21}ClFNO_3$: 366.1272; found: 366.1263.

This material was treated essentially as described in EXAMPLE 67 to provide 0.063 gm of the title compound. HRMS calculated for $C_{14}H_{12}ClFNO$: 266.0748; found: 266.0742.

EXAMPLE 74

2-methyl-4-(4-chloro-5-fluorobenzofur-7-yl)-1,2,3,6-tetrahydropyridine hydrochloride Beginning with 0.120 gm (0.482 mMol) 4-chloro-5-fluoro-7-bromobenzofuran and 0.150 gm (0.434 mMol) 1-(tert-butoxycarbonyl)-2-methyl-4-trifluoromethylsulfonyloxy-1,2,3,6-tetrahydropyridine, 0.082 gm (55%) 1-(tert-butoxycarbonyl)-2-methyl-4-(4-chloro-5-fluorobenzofur-7-yl)-1,2,3,6-tetrahydropyridine was prepared essentially as described in EXAMPLE 67.

M.S. (ES$^+$): m/e=366.9

This material was treated essentially as described in EXAMPLE 67 to provide 0.051 gm of the title compound. HRMS calculated for $C_{14}H_{12}ClFNO$: 266.0748; found: 266.0744.

EXAMPLE 75

2-methyl-4-(4-trifluoromethylbenzofur-7-yl)-1,2,3,6-tetrahydropyridine

Beginning with 2.0 gm (7.54 mMol) 4-trifluoromethyl-7-bromobenzofuran and 2.37 gm (6.86 mMol) 1-(tert-butoxycarbonyl)-2-methyl-4-trifluoromethylsulfonyloxy-1,2,3,6-tetrahydropyridine, 1.85 gm (70%) 1-(tert-butoxycarbonyl)-2-methyl-4-(4-trifluoromethylbenzofur-7-yl)-1,2,3,6-tetrahydropyridine was prepared essentially as described in EXAMPLE 67.

M.S.(ES$^+$): m/e=381.9

This material was treated essentially as described in EXAMPLE 67 to provide the title compound as a tan powder.

EA: Calculated for $C_{15}H_{13}F_3NO$—HCl: C, 56.70; H, 4.76; N, 4.41. Found: C, 56.51; H, 4.58; N, 4.52.

HRMS calculated for $C_{15}H_{13}F_3NO$: 282.1106; found: 282.1105.

EXAMPLE 76

Resolution of 2-methyl-4-(4-trifluoromethylbenzofur-7-yl)-1,2,3,6-tetrahydropyridine A mixture of 2 gm racemic 2-methyl-4-(4-trifluoromethylbenzofur-7-yl)-1,2,3,6-tetrahydropyridine and 2.75 gm (−)-tartaric acid mix (1:1:1 O-benzoyl:O-toluyl:O-anisoyltartaric acids) was dissolved in 50 mL isopropanol and 1 mL water. The mixture was seeded with 79% e.e. material resulting in rapid crystallization. The suspension was stirred at room temperature overnight and then filtered. The recovered solid was washed with 30 mL isopropanol and dried to provide 1.13 gm of a 100% e.e. salt containing approximately equimolar amounts of all three (−)-tartaric acids. This solid was dissolved in 5 mL 1N sodium hydroxide and was then extracted with 3×50 mL tert-butyl methyl ether. The organic phases were combined, washed with saturated aqueous sodium chloride, dried over sodium sulfate, and concentrated under reduced pressure. The residual oil was dissolved in 2 mL tetrahydrofuran and 5 mL diethyl ether. To this solution was added 1.8 mL 1M hydrogen chloride in diethyl ether with stirring. After 20 minutes the suspension was filtered. The solid was washed with diethyl ether and dried under vacuum at 60° C. to provide 0.63 gm of the hydrochloride salt.

MS(ES$^+$): m/e=282

The filtrate from the isolation of the (−)-tartaric salt was concentrated under reduced pressure and the residue was partitioned with dilute sodium hydroxide and ethyl acetate. The aqueous phase was extracted well with ethyl acetate. The organic extracts were combined, dried over sodium sulfate, and concentrated under reduced pressure to provide 1.5 gm of a residue. This residue was combined with 2.06 gm of the (+)-tartaric acid mixture in 40 mL isopropanol and 1 mL water. The mixture was stirred overnight and the resulting solid isolated by filtration to provide 0.92 gm of a salt with 96.5% e.e. This salt was converted to 0.50 gm of the corresponding hydrochloride essentially as described in the previous paragraph.

MS(ES$^+$): m/e=282

The ability of the compounds of this invention to bind to the 5-HT$_{2c}$ receptor subtype was measure essentially as described by Wainscott (Wainscott, et al., *Journal of Pharmacology and Experimental Therapeutics*, 276, 720–727 (1996)).

Membrane Preparation

AV12 cells stably transfected with the human 5-HT$_{2c}$ receptors were grown in suspension and harvested by centrifugation, resuspended in 50 mM tris-HCl, pH 7.4, and frozen at −70° C. On the day of assay, an aliquot of cells was thawed, resuspended in 40 mL of 50 ml tris-HCl, pH 7.4, and centrifuged at 39,800×g for 10 minutes at 4° C. The resulting pellet was resuspended, incubated at 37° C. for 10 minutes to remove endogenous serotonin, then centrifuged twice more.

[$^{125}$I]-DOI Binding for Determination of 5-HT$_{2c}$ Receptor Affinity

Briefly, prepared cell membranes were added to dilutions of compounds in a final solution containing 50 mM tris-HCl, pH 7.4, 9.75 mM MgCl$_2$, 0.5 mM EDTA, 10 μM pargyline, 0.1% sodium ascorbate, and 0.1 nM ($^{125}$I]-DOI, with 10 μM mianserin for defining non-specific binding. All incubations (800 μL) were performed at 37° C. for 30 minutes before harvesting onto GF/C filters prewet with 0.5% polyethyleneimine, with four 1 mL washes of ice-cold 50 mM tris-HCl, pH 7.4, and counting in a gamma counter. Nonlinear regression analysis was performed on the concentration response curves using a four parameter logistic equation described by DeLean (DeLean, et al., *Molecular Pharmacology*, 21, 5–16 (1982)). IC$_{50}$ values were converted to K$_i$ values using the Cheng-Prusoff equation (Cheng, et al., *Biochem. Pharmacol.*, 22, 3099–3108 (1973)).

Representative compounds of the present invention were found to have affinity for the 5-HT$_{2c}$ receptor as measured essentially by the procedure described supra.

The 5-HT$_{2C}$ receptor is functionally coupled to specific G-proteins. Agonist activation of 5-HT$_{2C}$ G-protein-coupled receptors results in the release of GDP from the *-subunit (G alpha q or G alpha i) of the G-protein and the subsequent binding of GTP. The binding of the stable analog [$^{35}$S]-GTPγS is an indicator of this receptor's activation.

[$^{35}$S]-GTPγS Binding

The immunoadsorption scintillation proximity assay (ISPA) in microtiter plates of [$^{35}$S]-GTPγS binding to G alpha q or G alpha i was modified from published conditions (DeLapp et al, JPET 289 (1999) 946–955). Test compounds were dissolved in DMSO and diluted in assay buffer consisting of 50 mM Tris-HCl (pH 7.4), 10 mM MgCl$_2$, 100 mM NaCl, and 0.2 mM EGTA. Incubations were performed over 12 test concentrations; volume was 200 μl. The incubation also contained 0.1 μM GDP and 0.25 nM [$^{35}$S]-GTPγS. Membrane homogenates from AV12 cells stably transfected with the human 5-HT$_{2C}$ receptor were added and the microtiter plates were incubated for 30 minutes at room temperature. The incubation was terminated by the addition of Nonidet P-40 (final concentration of 0.27%), followed by addition of rabbit polyclonal anti-G alpha q/11 antibody (0.2 μg per well), and anti-rabbit scintillation proximity assay beads (Amersham; 1.25 mg per well; final volume was 290 μl). The mixture was incubated for 3 hours at room temperature to complete the immunoadsorption of [$^{35}$S]-GTPγS bound to G alpha q/11. Microtiter plates were centrifuged briefly to pellet beads. [$^{35}$S]-GTPγS binding was quantitated by microtiter plate scintillation spectrometry (Wallac). Data analysis was performed by nonlinear regression analysis with GraphPad Prism software running on a personal computer, using 5-HT control concentration-response curves to define maximal stimulation of [$^{35}$S]-GTPγS binding.

Representative compounds of the present invention were tested in the [$^{35}$S]-GTPγS assay and were found to be agonists of the 5-HT$_{2c}$ receptor.

The ability of agonists of the 5-HT$_{2c}$ receptor in general, and the compounds of the present invention in particular, to treat obesity is demonstrated by testing in a feeding assay.

Fasted Feeding Assay

Male rats were fasted for 18 hours prior to testing. Rats were first assigned to either a treatment or control group (N=8), then weighed, administered drug or vehicle orally, and returned to their home cage. Thirty minutes later, food was made available to the animals. The the food and the food hopper was weighed before, one hour, two hours, and four hours after food was made available to the test animals. Weight of food consumed plus spillage by the treatment animals was compared to food consumed plus spillage by control animals using a one-way ANOVA, with a Dunnett's post-hoc test.

Representative compounds of the present invention were tested in the feeding assay and were found to reduce food consumed by fasting rats.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., Remington's Pharmaceutical Sciences, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Compound of Example 10 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Compound of Example 11 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Compound of Example 12 | 5 |
| Lactose | 95 |

The active mixture is mixed with the lactose and the mixture is added to a dry powder inhaling appliance.

Formulation Example 4

Tablets each containing 30 mg of active ingredient, are prepared as follows:

| Ingredient | Quantity (mg/tablet) |
|---|---|
| Compound of Example 26 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Compound of Example 38 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Compound of Example 33 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Compound of Example 31 | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Compound of Example 17 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Compound of Example 25 | 250.0 mg |
| Isotonic saline | 1000 ml |

Formulation Example 10

A topical formulation may be prepared as follows:

| Ingredient | Quantity |
|---|---|
| Compound of Example 22 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Compound of Example 7 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compounds, and the state of the patient.

We claim:

1. The compounds of Formula I:

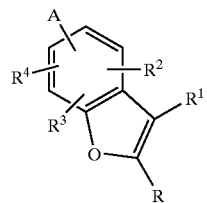

I where:

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, trifluoromethyl, cyano, $C_1$–$C_4$ alkoxy, $C_1$–$C_4$ alkoxycarbonyl, $C_1$–$C_6$ alkyl, $C_1$–$C_6$ alkyl substituted with a substituent selected from the group consisting of $C_1$–$C_4$ alkoxy and hydroxy, or —C(O)NHR$_9$;

$R^9$ is $C_1$–$C_8$ alkyl where the alkyl chain is optionally substituted with a substituent selected from the group consisting of phenyl and pyridyl;

A is attached at either the 4- or 7-position of the benzofuran nucleus and is an amine of formula:

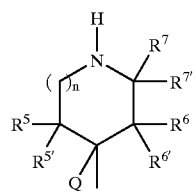

(i)

n is 0, 1, or 2;

$R^5$, $R^6$, and $R^7$ are independently hydrogen or $C_1$–$C_4$ alkyl;

Q is hydrogen;

$R^{5'}$ is hydrogen or methyl, provided that $R^{5'}$ may be methyl only when $R^5$ is other than hydrogen, or $R^{5'}$ and Q taken together with the carbon atoms to which they are attached form a double bond;

$R^{6'}$ is hydrogen or methyl, provided that $R^{6'}$ may be methyl only when $R^6$ is other than hydrogen, or $R^{6'}$ and Q taken together with the carbon atoms to which they are attached form a double bond;

$R^{7'}$ is hydrogen or methyl, provided that $R^{7'}$ may be methyl only when $R^7$ is other than hydrogen;

or pharmaceutically acceptable acid addition salts thereof subject to the following provisos:

a) when n is 1 or 2, at least one of $R^5$, $R^6$, and $R^7$, must be other than hydrogen; and b) no more than two of $R^5$, $R^{5'}$, $R^6$, $R^{6'}$, $R^7$, and $R^{7'}$ may be other than hydrogen.

2. A compound of claim 1 where A is attached at the 7-position of the benzofuran nucleus.

3. A compound according to claim 2 where Q is hydrogen.

4. A compound according to claim 3 where $R^6$ is $C_1$–$C_4$ alkyl and $R^5$, $R^{5'}$, $R^7$ and $R^{7'}$ are each hydrogen.

5. A compound according to claim 4 where $R^{6'}$ is hydrogen, and $R^6$ and the benzofuran core are in the cis configuration with regard to each other.

6. A compound according to claim 4 where $R^6$ is methyl.

7. A compound according to claim 4 where $R^6$ is methyl.

8. A compound according to claim 6 which is 3-methyl-4-(benzofur-7-yl)-piperidine, 3-methyl-4-(5-fluorobenzofur-7-yl)-piperidine, 3-methyl-1-(6-fluorobenzofur-7-yl)-piperidine, or 3-methyl-4-(5,6-difluorobenzofur-7-yl)-piperidine.

9. A compound according to claim 2 where one of $R^{5'}$ and Q, or $R^{6'}$ and Q, taken together with the carbon atoms to which they are attached form a double bond.

10. A compound according to claim 9 where of $R^{5'}$ and Q, taken together with the carbon atoms to which they are attached form a double bond, $R^6$ is $C_1$–$C_4$ alkyl, and $R^{6'}$ is methyl.

11. A compound according to claim 9 which is 2-methyl-4-(4-trifluoromethylbenzofur-7-yl)-1,2,3,6-tetrahydropyridine.

12. A pharmaceutical formulation which comprises, in association with a pharmaceutically acceptable carrier, diluent or excipient, a compound of Formula I:

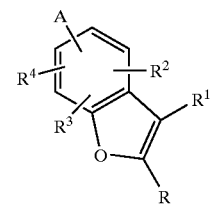

I where:

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, trifluoromethyl, cyano, $C_1$–$C_4$ alkoxy, $C_1$–$C_4$ alkoxycarbonyl, $C_1$–$C_6$ alkyl, $C_1$–$C_6$ alkyl substituted with a substituent selected from the group consisting of $C_1$–$C_4$ alkoxy and hydroxy, or —C(O)NHR$^9$;

$R^9$ is $C_1$–$C_8$ alkyl where the alkyl chain is optionally substituted with a substituent selected from the group consisting of phenyl and pyridyl;

A is attached at either the 4- or 7-position of the benzofuran nucleus and is an amine of formula:

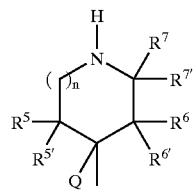

(i)

n is 0, 1, or 2;

$R^5$, $R^6$, and $R^7$ are independently hydrogen or $C_1$–$C_4$ alkyl;

Q is hydrogen;

$R^{5'}$ is hydrogen or methyl, provided that $R^{5'}$ may be methyl only when $R^5$ is other than hydrogen, or $R^{5'}$ and Q taken together with the carbon atoms to which they are attached form a double bond;

$R^{6'}$ is hydrogen or methyl, provided that $R^{6'}$ may be methyl only when $R^6$ is other than hydrogen, or $R^{6'}$ and Q taken together with the carbon atoms to which they are attached form a double bond;

$R^{7'}$ is hydrogen or methyl, provided that $R^{7'}$ may be methyl only when $R^7$ is other than hydrogen;

or pharmaceutically acceptable acid addition salts thereof subject to the following provisos:

a) when n is 1 or 2, at least one of $R^5$, $R^6$, and $R^7$, must be other than hydrogen; and b) no more than two of $R^5$, $R^{5'}$, $R^6$, $R^{6'}$, $R^7$, and $R^{7'}$ may be other than hydrogen.

13. A method for the treatment of obesity in mammals, comprising administering to a mammal in need of such activation a pharmaceutically effective amount of a compound of Formula I:

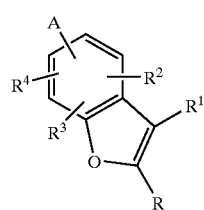

I where:

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, trifluoromethyl, cyano, $C_1$–$C_4$ alkoxy, $C_1$–$C_4$ alkoxycarbonyl, $C_1$–$C_6$ alkyl, $C_1$–$C_6$ alkyl substituted with a substituent selected from the group consisting of $C_1$–$C_4$ alkoxy and hydroxy, or —C(O)NHR$^9$;

$R^9$ is $C_1$–$C_8$ alkyl where the alkyl chain is optionally substituted with a substituent selected from the group consisting of phenyl and pyridyl;

A is attached at either the 4- or 7-position of the benzofuran nucleus and is an amine of formula:

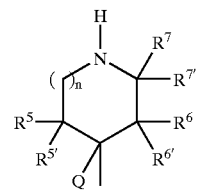

(i)

n is 0, 1, or 2;

$R^5$, $R^6$, and $R^7$ are independently hydrogen or $C_1$–$C_4$ alkyl;

Q is hydrogen;

$R^{5'}$ is hydrogen or methyl, provided that $R^{5'}$ may be methyl only when $R^5$ is other than hydrogen, or $R^{5'}$ and Q taken together with the carbon atoms to which they are attached form a double bond;

$R^{6'}$ is hydrogen or methyl, provided that $R^{6'}$ may be methyl only when $R^6$ is other than hydrogen, or $R^{6'}$ and Q taken together with the carbon atoms to which they are attached form a double bond;

$R^{7'}$ is hydrogen or methyl, provided that $R^{7'}$ may be methyl only when $R^7$ is other than hydrogen;

or pharmaceutically acceptable acid addition salts thereof subject to the following provisos:

a) when n is 1 or 2, at least one of $R^5$, $R^6$, and $R^7$, must be other than hydrogen; and b) no more than two of $R^5$, $R^{5'}$, $R^6$, $R^{6'}$, $R^7$, and $R^{7'}$ may be other than hydrogen.

14. The method of claim 13 where the mammal is human.

15. A method for the treatment of depression in mammals, comprising administering to a mammal in need of such activation a pharmaceutically effective amount of a compound of Formula I:

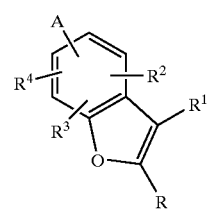

I where:

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, trifluoromethyl, cyano, $C_1$–$C_4$ alkoxy, $C_1$–$C_4$ alkoxycarbonyl, $C_1$–$C_6$ alkyl, $C_1$–$C_6$ all substituted with a substituent selected from the group consisting of $C_1$–$C_4$ alkoxy and hydroxy, or —C(O)NHR$^9$;

$R^9$ is $C_1$–$C_8$ alkyl where the alkyl chain is optionally substituted with a substituent selected from the group consisting of phenyl and pyridyl;

A is attached at either the 4- or 7-position of the benzofuran nucleus and is an amine of formula:

(i)

$$\begin{array}{c} H \\ | \\ N-R^7 \\ (\ )_n \quad -R^{7'} \\ R^5- \quad -R^6 \\ R^{5'} \quad R^{6'} \\ Q \end{array}$$

n is 0, 1, or 2;

$R^5$, $R^6$, and $R^7$ are independently hydrogen or $C_1$–$C_4$ alkyl;

Q is hydrogen;

$R^{5'}$ is hydrogen or methyl, provided that $R^{5'}$ may be methyl only when $R^5$ is other than hydrogen, or $R^{5'}$ and Q taken together with the carbon atoms to which they are attached form a double bond;

$R^{6'}$ is hydrogen or methyl, provided that $R^{6'}$ may be methyl only when $R^6$ is other than hydrogen, or $R^{6'}$ and Q taken together with the carbon atoms to which they are attached form a double bond;

$R^{7'}$ is hydrogen or methyl, provided that $R^{7'}$ may be methyl only when $R^7$ is other than hydrogen;

or pharmaceutically acceptable acid addition salts thereof subject to the following provisos:

a) when n is 1 or 2, at least one of $R^5$, $R^6$, and $R^7$, must be other than hydrogen; and b) no more than two of $R^5$, $R^{5'}$, $R^6$, $R^{6'}$, $R^7$, and $R^{7'}$ may be other than hydrogen.

16. The method of claim 15 where the mammal is human.

17. A method for the treatment of obsessive compulsive disorder in mammals, comprising administering to a mammal in need of such treatment an effective amount of a compound of Formula I:

I $$\begin{array}{c} A \\ R^4- \quad -R^2 \\ R^3 \quad R^1 \\ O \\ R \end{array}$$

where:

R is hydrogen, halo, trifluoromethyl or $C_1$–$C_6$ alkyl;

$R^1$ is hydrogen, halo, trifluoromethyl, phenyl, or $C_1$–$C_6$ alkyl;

$R^2$, $R^3$, and $R^4$ are independently hydrogen, halo, trifluoromethyl, cyano, $C_1$–$C_4$ alkoxy, $C_1$–$C_4$ alkoxycarbonyl, $C_1$–$C_6$ alkyl, $C_1$–$C_6$ alkyl substituted with a substituent selected from the group consisting of $C_1$–$C_4$ alkoxy and hydroxy, or —C(O)NHR$^9$;

$R^9$ is $C_1$–$C_8$ alkyl where the alkyl chain is optionally substituted with a substituent selected from the group consisting of phenyl and pyridyl;

A is attached at either the 4- or 7-position of the benzofuran nucleus and is an amine of formula:

(i)

$$\begin{array}{c} H \\ | \\ N-R^7 \\ (\ )_n \quad -R^{7'} \\ R^5- \quad -R^6 \\ R^{5'} \quad R^{6'} \\ Q \end{array}$$

n is 0, 1, or 2;

$R^5$, $R^6$, and $R^7$ are independently hydrogen or $C_1$–$C_4$ alkyl;

Q is hydrogen;

$R^{5'}$ is hydrogen or methyl, provided that $R^{5'}$ may be methyl only when $R^5$ is other than hydrogen, or $R^{5'}$ and Q taken together with the carbon atoms to which they are attached form a double bond;

$R^{6'}$ is hydrogen or methyl, provided that $R^{6'}$ may be methyl only when $R^6$ is other than hydrogen, or $R^{6'}$ and Q taken together with the carbon atoms to which they are attached form a double bond;

$R^{7'}$ is hydrogen or methyl, provided that $R^{7'}$ may be methyl only when $R^7$ is other than hydrogen;

or pharmaceutically acceptable acid addition salts thereof subject to the following provisos:

a) when n is 1 or 2, at least one of $R^5$, $R^6$, and $R^7$, must be other than hydrogen; and b) no more than two of $R^5$, $R^{5'}$, $R^6$, $R^{6'}$, $R^7$, and $R^{7'}$ may be other than hydrogen.

18. The method of claim 17 where the mammal is human.

* * * * *

UNITED STATES PATENT AND TRADEMARK OFFICE
CERTIFICATE OF CORRECTION

PATENT NO. : 6,881,733 B1
DATED : April 19, 2005
INVENTOR(S) : Karin Briner et al.

Page 1 of 1

It is certified that error appears in the above-identified patent and that said Letters Patent is hereby corrected as shown below:

Column 75,
Line 35, reads "...or —C(O)NHR$_9$," should read -- "...or —C(O)NHR$^9$,"— --

Column 76,
Line 20, reads "...3-methyl-1-(6-..." should read -- "...3-methyl-4-(6-..."— --

Column 78,
Line 62, reads, "...$C_1$-$C_6$ all substituted..." should read -- "...$C_1$-$C_6$ alkyl substituted..."--
Line 64, reads, "...or —C(O)NHR$_9$," should read -- "...C(O)NHR$^9$," --

Signed and Sealed this

Twenty-eighth Day of June, 2005

JON W. DUDAS
*Director of the United States Patent and Trademark Office*